(12) United States Patent
Lafferty et al.

(10) Patent No.: US 6,866,824 B2
(45) Date of Patent: Mar. 15, 2005

(54) CAPILLARY ARRAY-BASED SAMPLE SCREENING

(75) Inventors: William Michael Lafferty, Encinitas, CA (US); Jay M. Short, Rancho Santa Fe, CA (US); Martin Keller, San Diego, CA (US)

(73) Assignee: Diversa Corporation, San Diego, CA (US)

( * ) Notice: Subject to any disclaimer, the term of this patent is extended or adjusted under 35 U.S.C. 154(b) by 363 days.

(21) Appl. No.: 10/157,653

(22) Filed: May 28, 2002

(65) Prior Publication Data

US 2003/0044968 A1 Mar. 6, 2003

Related U.S. Application Data

(60) Division of application No. 09/687,219, filed on Oct. 12, 2000, now Pat. No. 6,794,127, and a continuation-in-part of application No. 09/636,778, filed on Aug. 11, 2000, now abandoned, which is a continuation-in-part of application No. 09/444,112, filed on Nov. 22, 1999, which is a continuation of application No. 09/098,206, filed on Jun. 16, 1998, now Pat. No. 6,174,673, which is a continuation-in-part of application No. 08/876,276, filed on Sep. 16, 1997.

(51) Int. Cl.[7] .............................................. G01N 21/00
(52) U.S. Cl. ............................... 422/82.05; 422/82.09; 422/82.11; 436/165
(58) Field of Search ............................. 422/58, 59, 69, 422/70, 82.05, 82.08, 82.09, 82.11; 436/164, 165, 174

(56) References Cited

U.S. PATENT DOCUMENTS

| | | |
|---|---|---|
| 4,276,048 A | 6/1981 | Leaback |
| 4,621,059 A | 11/1986 | Rokugawa |
| 5,274,240 A | 12/1993 | Mathies et al. |
| 5,439,578 A * | 8/1995 | Dovichi et al. ............. 204/603 |
| 5,584,982 A | 12/1996 | Dovichi et al. |
| 5,670,113 A | 9/1997 | Akong et al. |
| 5,675,155 A | 10/1997 | Pentoney, Jr. et al. |
| 5,716,825 A * | 2/1998 | Hancock et al. ......... 435/286.5 |
| 5,741,411 A | 4/1998 | Yeung et al. |
| 5,759,779 A * | 6/1998 | Dehlinger ..................... 435/6 |
| 5,763,263 A | 6/1998 | Dehlinger |
| 5,790,727 A | 8/1998 | Dhadwal et al. |
| 5,833,827 A | 11/1998 | Anazawa et al. |
| 5,843,767 A | 12/1998 | Beattie |
| 5,872,010 A * | 2/1999 | Karger et al. ............... 436/173 |
| 5,938,908 A * | 8/1999 | Anazawa et al. ........... 204/603 |
| 5,958,672 A | 9/1999 | Short |
| 6,027,873 A | 2/2000 | Schellenberger et al. |
| 6,039,925 A * | 3/2000 | Nemoto ................... 422/82.08 |
| 6,048,444 A | 4/2000 | Takahashi et al. |
| 6,054,032 A | 4/2000 | Haddad et al. |
| 6,083,763 A | 7/2000 | Balch |
| 6,086,740 A | 7/2000 | Kennedy |
| 6,086,825 A | 7/2000 | Sundberg et al. |
| 6,090,251 A | 7/2000 | Sundberg et al. |
| 6,306,578 B1 | 10/2001 | Schellenberger et al. |
| 6,387,331 B1 | 5/2002 | Hunter |
| 6,653,151 B2 * | 11/2003 | Anderson et al. ........... 436/518 |
| 6,713,309 B1 * | 3/2004 | Anderson et al. ........... 436/518 |

FOREIGN PATENT DOCUMENTS

| | | |
|---|---|---|
| WO | WO 90/14590 | 11/1990 |
| WO | WO 97 45730 A1 | 12/1997 |
| WO | WO 98/04920 | 2/1998 |
| WO | WO 98 28075 A1 | 7/1998 |

(List continued on next page.)

*Primary Examiner*—Jeffrey R. Snay
(74) *Attorney, Agent, or Firm*—Dla Piper Rudnick Gray Cary US LLP

(57) ABSTRACT

Provided are methods of screening and identification of bioactivities and bioactive molecules of interest using a capillary array system. More specifically, disclosed are methods of using optical detection and capillary array-based techniques for screening libraries and recovering bioactive molecules having a desired activity or a nucleic acid sequence encoding such bioactive molecules.

2 Claims, 17 Drawing Sheets

FOREIGN PATENT DOCUMENTS

| | | |
|---|---|---|
| WO | WO 98 38490 A1 | 9/1998 |
| WO | WO 99/34920 | 7/1999 |
| WO | WO 99 39191 A1 | 9/1999 |
| WO | WO 99 49294 A2 | 9/1999 |

\* cited by examiner

Recovery System Accuracy 8 hours:

24 hours:

48 hours:

8 hr:

24 hr:

Array 2: 1 cell/capillary  95 % negative/5 % positive 24 hr:

48 hr:

48 hr:

Imaging & Recovery System

US 6,866,824 B2

CAPILLARY ARRAY-BASED SAMPLE SCREENING

CROSS REFERENCE TO RELATED APPLICATIONS

This application is a divisional of U.S. application Ser. No. 09/687,219, filed Oct. 12, 2000, now U.S. Pat. No. 6,794,127 which is a continuation-in-part of U.S. patent application Ser. No. 09/444,112, filed Nov. 22, 1999, which is a continuation-in-part of U.S. patent application Ser. No. 08/876,276, filed Jun. 16, 1997, and is a continuation-in-part of U.S. patent application Ser. No. 09/636,778, filed Aug. 11, 2000, which application is a continuation and claims the benefit of priority under 35 U.S.C. §120 of U.S. patent application Ser. No. 09/098,206, filed Jun. 16, 1998, now U.S. Pat. No. 6,174,673, which is a continuation-in-part of U.S. patent application Ser. No. 08/876,276, filed Jun. 16, 1997, all of the contents of which are incorporated by reference in their entirety herein.

FIELD OF THE INVENTION

The present invention relates generally to screening and identification of new bioactive molecules. More specifically, the present invention relates to methods of using optical detection and capillary array-based techniques for screening samples or libraries and recovering bioactive molecules having a desired activity or nucleic acid sequences encoding bioactive molecules.

BACKGROUND

There has been a dramatic increase in the need for bioactive compounds with novel activities. This demand has arisen largely from changes in worldwide demographics coupled with the clear and increasing trend in the number of pathogenic organisms that are resistant to currently available antibiotics as well as the need for new industrial processes for synthesis of compounds. For example, while there has been a surge in demand for antibacterial drugs in emerging nations with young populations, countries with aging populations, such as the U.S., require a growing repertoire of drugs against cancer, diabetes, arthritis and other debilitating conditions. The death rate from infectious diseases has increased 58% between 1980 and 1992 and it has been estimated that the emergence of antibiotic resistant microbes has added in excess of $30 billion annually to the cost of health care in the U.S. alone. (Adams et al., *Chemical and Engineering News*, 1995; Amann et al., *Microbiological Reviews*, 59, 1995). As a response to this trend pharmaceutical companies have significantly increased their screening of microbial diversity for compounds with unique activities or specificities.

The majority of bioactive compounds currently in use are derived from soil microorganisms. Many microbes inhabiting soils and other complex ecological communities produce a variety of compounds that increase their ability to survive and proliferate. These compounds are generally thought to be nonessential for growth of the organism and are synthesized with the aid of genes involved in intermediary metabolism. Such secondary metabolites that influence the growth or survival of other organisms are known as ≈bioactive? compounds and serve as key components of the chemical defense arsenal of both micro- and macroorganisms. Humans have exploited these compounds for use as antibiotics, antiinfectives and other bioactive compounds with activity against a broad range of prokaryotic and eukaryotic pathogens (Barnes et al., *Proc. Nat. Acad. Sci. U.S.A.*, 91, 1994).

The approach currently used to screen microbes for new bioactive compounds has been largely unchanged since the inception of the field. New isolates of bacteria, particularly gram positive strains from soil environments, are collected and their metabolites tested for pharmacological activity.

There is still tremendous biodiversity that remains untapped as the source of lead compounds. However, the currently available methods for screening and producing lead compounds cannot be applied efficiently to these under-explored resources. For instance, it is estimated that at least 99% of marine bacteria species do not survive on laboratory media, and commercially available fermentation equipment is not optimal for use in the conditions under which these species will grow, hence these organisms are difficult or impossible to culture for screening or re-supply. Recollection, growth, strain improvement, media improvement and scale-up production of the drug-producing organisms often pose problems for synthesis and development of lead compounds. Furthermore, the need for the interaction of specific organisms to synthesize some compounds makes their use in discovery extremely difficult. New methods to harness the genetic resources and chemical diversity of these untapped sources of compounds for use in drug discovery are very valuable.

A central core of modem biology is that genetic information resides in a nucleic acid genome, and that the information embodied in such a genome (i.e., the genotype) directs cell function. This occurs through the expression of various genes in the genome of an organism and regulation of the expression of such genes. The expression of genes in a cell or organism defines the cell or organism's physical characteristics (i.e., its phenotype). This is accomplished through the translation of genes into proteins. Determining the biological activity of a protein obtained from an environmental sample can provide valuable information about the role of proteins in the environments. In addition, such information can help in the development of biologics, diagnostics, therapeutics, and compositions for industrial applications.

Accordingly, the present invention provides methods to access this untapped biodiversity and to rapidly screen for sequences and activities of interest utilizing recombinant DNA technology. This invention combines the benefits associated with the ability to rapidly screen natural compounds with the flexibility and reproducibility afforded with working with the genetic material of organisms.

SUMMARY OF THE INVENTION

The invention provides a rapid and efficient method for identifying a bioactivity or biomolecule of interest. In one embodiment, the method includes introducing a recombinant clone into a capillary tube of a capillary array, wherein each capillary tube of the capillary array has at least one wall defining a lumen for retaining the recombinant clone, and wherein the at least one wall is made of a material having a low refractive index. The recombinant clone is exposed to conditions which induce a detectable signal, and detecting the detectable signal in the capillary tube to identify one or more capillaries containing the detectable signal thereby identifying the bioactivity or biomolecule of interest.

In another embodiment, the invention provides a method for identifying a bioactivity or biomolecule of interest by introducing a recombinant clone into a capillary tube of a capillary array, wherein each capillary tube of the capillary array has at least one wall defining a lumen for retaining the recombinant clone, and the at least one wall is made of a material having a low refractive index, and wherein the recombinant clone contains a substrate. The recombinant clone is exposed to conditions which causes the substrate to produce a detectable signal, and detecting the detectable signal in the capillary tube to identify one or more capillaries containing the detectable signal thereby identifying the bioactivity or biomolecule of interest.

In yet another embodiment, the invention provides a method for identifying a bioactivity or biomolecule of interest, by introducing a recombinant clone into a capillary tube of a capillary array, wherein each capillary tube of the capillary array has at least one wall defining a lumen for retaining the recombinant clone, and wherein the recombinant clone contains a substrate, exposing and the recombinant clone to conditions which causes the substrate to produce a detectable signal, and detecting the detectable signal in the capillary tube to identify one or more capillaries containing the detectable signal thereby identifying the bioactivity or biomolecule of interest.

In one embodiment, the invention provides a method for identifying a bioactivity or biomolecule of interest. The method includes introducing a substrate labeled with a detectable molecule and a recombinant clone into a capillary tube of a capillary array. Each capillary tube of the capillary array has at least one wall defining a lumen for retaining the substrate and the recombinant clone, and wherein the at least one wall is made of a material having a low refractive index. The method further includes culturing the capillary tube containing the substrate and the recombinant clone under conditions which allow interaction of the substrate and the recombinant clone to produce a detectable signal and detecting the detectable signal in the capillary tube to identify one or more capillaries containing the detectable signal thereby identifying the bioactivity or biomolecule of interest.

In another embodiment, the invention provides a method for identifying a bioactivity or biomolecule of interest by introducing a substrate labeled with a detectable molecule and a recombinant clone into a capillary tube of a capillary array, wherein each capillary tube of the capillary array has at least one wall defining a lumen for retaining the substrate and the recombinant clone and wherein each capillary tube in the array is separated from one another by an outer wall having a material with a low refractive index. The capillary tube containing the substrate and the recombinant clone are cultured under conditions which allow interaction of the substrate and the recombinant clone to produce a detectable signal and detecting the detectable signal in the capillary tube to identify one or more capillary tubes containing the detectable signal thereby identifying the bioactivity or biomolecule of interest.

In yet another embodiment, the invention provides a method for identifying a bioactivity or biomolecule of interest by introducing a substrate labeled with a detectable molecule and a recombinant clone into a capillary tube of a capillary array, wherein each capillary tube of the capillary array has at least a first wall and a second wall wherein the first wall defines a lumen for retaining the substrate and the recombinant clone and is made of a material having a high refractive index and the second wall surrounds the first wall and is made of a material having a low refractive index, wherein the second wall is in contact with at least one other capillary tube second wall. The capillary tube containing the substrate and the recombinant clone are cultured under conditions which allow interaction of the substrate and the recombinant clone to produce a detectable signal and detecting the detectable signal in the capillary tube to identify one or more capillary tubes containing the detectable signal thereby identifying the bioactivity or biomolecule of interest.

In another embodiment, the invention provides an automated capillary array system. The system includes a plurality of capillaries defining a capillary array, wherein each of the plurality of capillaries is separated from each other capillary in the array by at least one material having a low refractive index and wherein each capillary has openings at each end of the capillary. The system further includes at least one magnetic field apparatus in magnetic communication with the capillary array to cause movement of paramagnetic beads, an optical array in optical communication with at least one end of the capillary array that detects an optical signal produced from a sample in at least one capillary of the capillary array and a computer system in communication with the magnetic field apparatus and the optical array, wherein the computer system controls the magnetic field surrounding the capillary array and processes data detected by the optical array.

In another embodiment, the invention provides a method for identifying a compound of interest, by introducing a sample containing a plurality of compounds into a capillary tube of a capillary array, wherein each capillary tube of the capillary array has at least one wall defining a lumen for retaining the sample, and the at least one wall is made of a material having a low refractive index, and wherein the recombinant clone contains a substrate, exposing and the sample in the capillary tube to conditions which causes the compound of interest to produce a detectable signal, and detecting the detectable signal in the capillary tube to identify one or more capillaries containing the detectable signal thereby identifying the compound of interest.

DETAILED DESCRIPTION OF THE INVENTION

Figure 1:
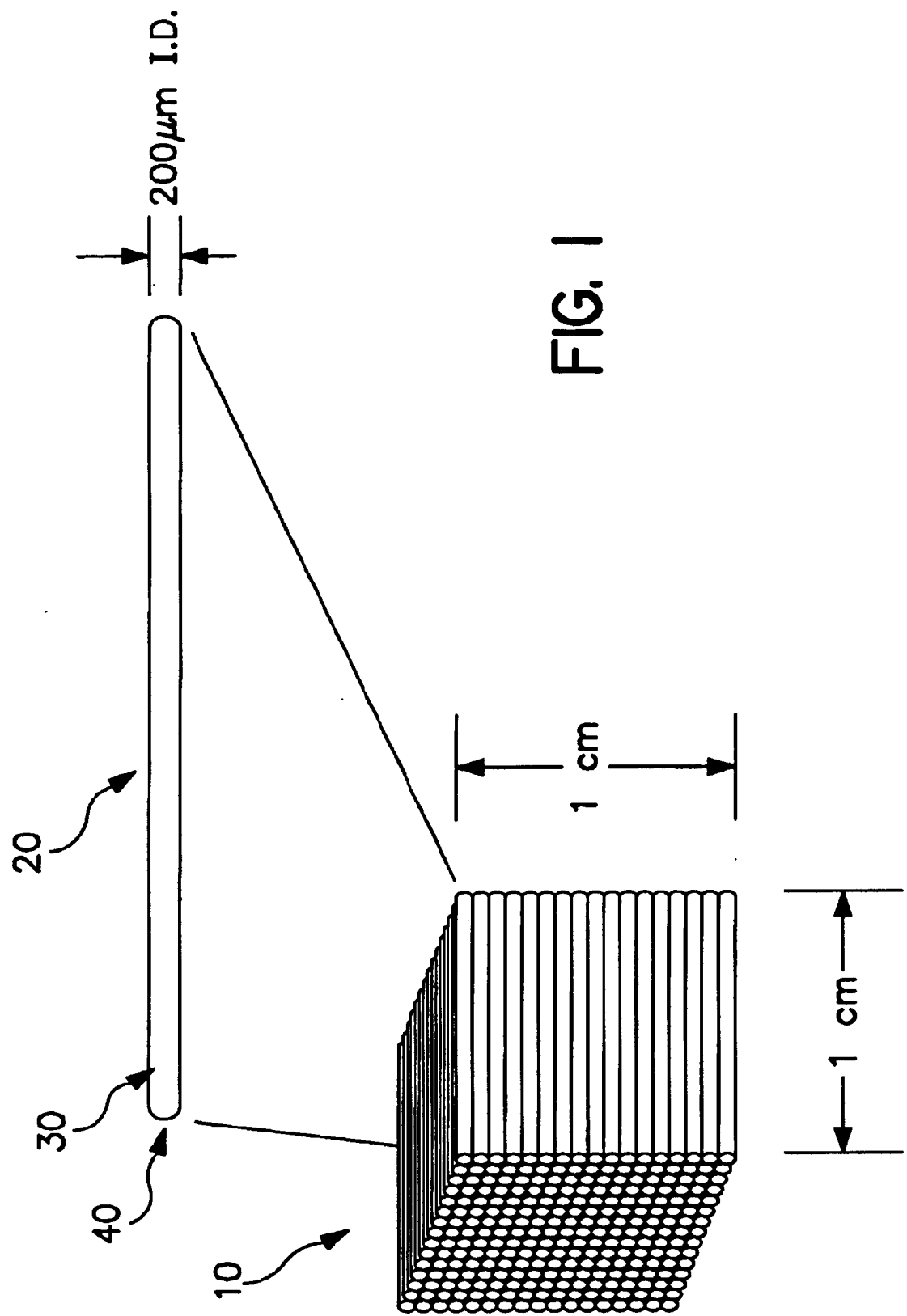
FIG. 1 shows an example of dimensions of a capillary array of the invention.

The present invention provides a rapid high-throughput method of assaying a sample for a biomolecule or bioactivity of interest. The methods, systems, and automated techniques of the invention are based upon microcapillary tubes capable of holding a liquid sample and techniques for detecting a detectable signal in one or more capillary tubes in a capillary array. The method and system further include techniques for recovery of samples from the capillary tubes.

The present invention provides rapid screening of libraries derived from a mixed population of organisms from, for example, an environmental sample or an uncultivated population of organisms. In one embodiment, gene libraries are generated, clones are either exposed to a substrate or substrate(s) of interest, or hybridized to a fluorescence labeled probe having a sequence corresponding to a sequence of interest and positive clones are identified by fluorescence emission.

In one embodiment, libraries generated from a mixed population of organisms are screened for a bioactivity or biomolecule of interest. For example, in one embodiment, expression libraries are generated, clones are exposed to a substrate or substrate(s) of interest, and positive clones are identified and isolated. The present invention does not require cell viability. The cells only need to be viable long enough to produce the molecule to be detected, and can thereafter be either viable or non-viable cells, so long as the biomolecule, or the nucleic acid remain active and/or intact.

In certain embodiments, the invention provides an approach that combines direct cloning of genes encoding novel or desired bioactivities from environmental samples with an extremely high-throughput screening system designed for the rapid discovery of new molecules, for example enzymes. The approach is based on the construction of environmental "expression libraries" which can represent the collective genomes of numerous naturally occurring microorganisms archived in cloning vectors that can be propagated in *E. coli* or other suitable host cells. Because the cloned DNA can be initially extracted directly from environmental samples, the libraries are not limited to the small fraction of prokaryotes that can be grown in pure culture. Additionally, a normalization of the environmental DNA present in these samples could allow more equal representation of the DNA from all of the species present in a sample. Normalization techniques (described below) can dramatically increase the efficiency of finding interesting genes from minor constituents of the sample that may be under-represented by several orders of magnitude compared to the dominant species in the sample.

The present invention provides a high-throughput capillary array system for screening that allows one to assess an enormous number of clones or samples to identify and recover cells encoding useful enzymes, as well as other biomolecules (e.g., ligands, nucleic acids, or proteins). In particular, the capillary array-based techniques described herein can be used to screen, identify and recover proteins having a desired bioactivity or other ligands having a desired binding affinity. For example, binding assays may be conducted by using an appropriate substrate or other marker that emits a detectable signal upon the occurrence of the desired binding event.

This invention differs from fluorescence activated cell sorting, as normally performed, in several aspects. FACS machines have been employed in the studies focused on the analyses of eukaryotic and prokaryotic cell lines and cell culture processes. FACS has also been utilized to monitor production of foreign proteins in both eukaryotes and prokaryotes to study, for example, differential gene expression and the like. The detection and counting capabilities of the FACS system have been applied in these examples. However, FACS has never previously been employed in a discovery process to screen for and recover bioactivities in prokaryotes. Furthermore, the present invention does not require cells to survive, as do previously described technologies, since the desired nucleic acid (recombinant clones) can be obtained from alive or dead cells. The cells only need to be viable long enough to produce the compound to be detected, and can thereafter be either viable or non-viable cells so long as the expressed biomolecule remains active. The present invention also solves problems that would have been associated with detection and sorting of *E. coli* expressing recombinant enzymes, and recovering encoding nucleic acids. Additionally, the present invention includes within its embodiments any apparatus capable of detecting fluorescent wavelengths associated with biological material, such apparatus are defined herein as fluorescent analyzers.

Prior to the present invention, the evaluation of complex environmental expression libraries was rate limiting. The present invention allows the rapid screening of complex environmental libraries, containing, for example, genomic sequences from thousands of different organisms. The benefits of the present invention can be seen, for example, in screening a complex environmental sample. Screening of a complex sample previously required one to use labor intensive methods to screen several million clones to cover the genomic biodiversity. The invention represents an extremely high-throughput screening method which allows one to assess this enormous number of clones. The method disclosed allows the screening anywhere from about 30 million to about 200 million clones per hour for a desired nucleic acid sequence or biological activity. This allows the thorough screening of environmental libraries for clones expressing novel biomolecules.

As used herein and in the appended claims, the singular forms "a," "and," and "the" include plural referents unless the context clearly dictates otherwise. Thus, for example, reference to "a clone" includes a plurality of clones and reference to "the nucleic acid sequence" generally includes reference to one or more nucleic acid sequences and equivalents thereof known to those skilled in the art, and so forth.

Unless defined otherwise, all technical and scientific terms used herein have the same meaning as commonly understood to one of ordinary skill in the art to which the invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the databases, proteins, and methodologies, which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

An "amino acid" is a molecule having the structure wherein a central carbon atom (the α-carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino acid carboxylic groups in the dehydration reaction that links one amino acid to another. As a result, when incorporated into a protein, an amino acid is referred to as an "amino acid residue."

"Protein" or "polypeptide" refers to any polymer of two or more individual amino acids (whether or not naturally occurring) linked via a peptide bond, and occurs when the carboxyl carbon atom of the carboxylic acid group bonded to the α-carbon of one amino acid (or amino acid residue) becomes covalently bound to the amino nitrogen atom of amino group bonded to the α-carbon of an adjacent amino acid. The term "protein" is understood to include the terms "polypeptide" and "peptide" (which, at times may be used interchangeably herein) within its meaning. In addition, proteins comprising multiple polypeptide subunits (e.g., DNA polymerase III, RNA polymerase II) or other components (for example, an RNA molecule, as occurs in telomerase) will also be understood to be included within the meaning of "protein" as used herein. Similarly, fragments of proteins and polypeptides are also within the scope of the invention and may be referred to herein as "proteins."

A particular amino acid sequence of a given protein (i.e., the polypeptide's "primary structure," when written from the amino-terminus to carboxy-terminus) is determined by the nucleotide sequence of the coding portion of a mRNA, which is in turn specified by genetic information, typically genomic DNA (including organelle DNA, e.g., mitochondrial or chloroplast DNA). Thus, determining the sequence of a gene assists in predicting the primary sequence of a corresponding polypeptide and more particular the role or activity of the polypeptide or proteins encoded by that gene or polynucleotide sequence.

The term "isolated" means altered "by the hand of man" from its natural state; i.e., if it occurs in nature, it has been changed or removed from its original environment, or both. For example, a naturally occurring polynucleotide or a polypeptide naturally present in a living animal, a biological sample or an environmental sample in its natural state is not "isolated", but the same polynucleotide or polypeptide separated from the coexisting materials of its natural state is "isolated", as the term is employed herein. Such polynucleotides, when introduced into host cells in culture or in whole organisms, still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions).

"Polynucleotide" or "nucleic acid sequence" refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. A polynucleotides as used herein refers to, among others, single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term polynucleotide encompasses genomic DNA or RNA (depending upon the organism, i.e., RNA genome of viruses), as well as mRNA encoded by the genomic DNA, and cDNA.

As mentioned above, there is currently a need in the biotechnology and chemical industry for molecules that can optimally carry out biological or chemical processes (e.g., enyzmes). For example, molecules and compounds that are utilized in both established and emerging chemical, pharmaceutical, textile, food and feed, detergent markets must meet stringent economical and environmental standards. The synthesis of polymers, pharmaceuticals, natural products and agrochemicals is often hampered by expensive processes which produce harmful byproducts and which suffer from poor or inefficient catalysis. Enzymes, for example, have a number of remarkable advantages which can overcome these problems in catalysis: they act on single functional groups, they distinguish between similar functional groups on a single molecule, and they distinguish between enantiomers. Moreover, they are biodegradable and function at very low mole fractions in reaction mixtures. Because of their chemo-, regio- and stereospecificity, enzymes present a unique opportunity to optimally achieve desired selective transformations. These are often extremely difficult to duplicate chemically, especially in single-step reactions. The elimination of the need for protection groups, selectivity, the ability to carry out multi-step transformations in a single reaction vessel, along with the concomitant reduction in environmental burden, has led to the increased demand for enzymes in chemical and pharmaceutical industries. Enzyme-based processes have been gradually replacing many conventional chemical-based methods. A current limitation to more widespread industrial use is primarily due to the relatively small number of commercially available enzymes. Only~300 enzymes (excluding DNA modifying enzymes) are at present commercially available from the>3000 non DNA-modifying enzyme activities thus far described.

The use of enzymes for technological applications also may require performance under demanding industrial conditions. This includes activities in environments or on substrates for which the currently known arsenal of enzymes was not evolutionarily selected. However, the natural environment provides extreme conditions including, for example, extremes in temperature and pH. A number of organisms have adapted to these conditions due in part to selection for polypeptides than can withstand these extremes.

Enzymes have evolved by selective pressure to perform very specific biological functions within the milieu of a living organism, under conditions of temperature, pH and salt concentration. For the most part, the non-DNA modifying enzyme activities thus far described have been isolated from mesophilic organisms, which represent a very small fraction of the available phylogenetic diversity. The dynamic field of biocatalysis takes on a new dimension with the help of enzymes isolated from microorganisms that thrive in extreme environments. For example, such enzymes must function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. Environmental samples obtained, for example, from extreme conditions containing organisms, polynucleotides or polypeptides (e.g., enzymes) open a new field in biocatalysis. By rapidly screening for polynucleotides encoding polypeptides of interest, the invention provides not only a source of materials for the development of biologics, therapeutics, and enzymes for industrial applications, but also provides a new materials for further processing by, for example, directed evolution and mutagenesis to develop molecules or polypeptides modified for particular activity or conditions.

In addition to the need for new enzymes for industrial use, there has been a dramatic increase in the need for bioactive compounds with novel activities. This demand has arisen largely from changes in worldwide demographics coupled with the clear and increasing trend in the number of pathogenic organisms that are resistant to currently available antibiotics. For example, while there has been a surge in demand for antibacterial drugs in emerging nations with young populations, countries with aging populations, such as the U.S., require a growing repertoire of drugs against cancer, diabetes, arthritis and other debilitating conditions. The death rate from infectious diseases has increased 58% between 1980 and 1992 and it has been estimated that the emergence of antibiotic resistant microbes has added in excess of $30 billion annually to the cost of health care in the U.S. alone. (Adams et al., *Chemical and Engineering News*, 1995; Amann et al., *Microbiological Reviews*, 59, 1995). As a response to this trend pharmaceutical companies have significantly increased their screening of microbial diversity for compounds with unique activities or specificity. Accordingly, the invention can be used to obtain and identify polynucleotides and related sequence specific information from, for example, infectious microorganisms present in the environment such as, for example, in the gut of various macroorganisms.

Identifying novel enzymes or bioactive molecules in an environmental sample is one solution to this problem. By rapidly identifying polypeptides having an activity of interest and polynucleotides encoding the polypeptide of interest the invention provides methods, compositions and sources for the development of biologics, diagnostics, therapeutics, and compositions for industrial applications.

In another embodiment, the methods and compositions of the invention provide for the identification of lead drug compounds present in an environmental sample. The methods of the invention provide the ability to mine the environment for novel drugs or identify related drugs contained in different microorganisms. There are several common sources of lead compounds (drug candidates), including natural product collections, synthetic chemical collections, and synthetic combinatorial chemical libraries, such as nucleotides, peptides, or other polymeric molecules that have been identified or developed as a result of environmental mining. Each of these sources has advantages and disadvantages. The success of programs to screen these candidates depends largely on the number of compounds entering the programs, and pharmaceutical companies have to date screened hundred of thousands of synthetic and natural compounds in search of lead compounds. Unfortunately, the ratio of novel to previously-discovered compounds has diminished with time. The discovery rate of novel lead compounds has not kept pace with demand despite the best efforts of pharmaceutical companies. There exists a strong need for accessing new sources of potential drug candidates. Accordingly, the invention provides a rapid and efficient method to identify and characterize environmental samples that may contain novel drug compounds.

The majority of bioactive compounds currently in use are derived from soil microorganisms. Many microbes inhabiting soils and other complex ecological communities produce a variety of compounds that increase their ability to survive and proliferate. These compounds are generally thought to be nonessential for growth of the organism and are synthesized with the aid of genes involved in intermediary metabolism hence their name—"secondary metabolites". Secondary metabolites that influence the growth or survival of other organisms are known as "bioactive" compounds and serve as key components of the chemical defense arsenal of both micro- and macro-organisms. Humans have exploited these compounds for use as antibiotics, antiinfectives and other bioactive compounds with activity against a broad range of prokaryotic and eukaryotic pathogens. Approximately 6,000 bioactive compounds of microbial origin have been characterized, with more than 60% produced by the gram positive soil bacteria of the genus *Streptomyces*. (Barnes et al., *Proc. Nat. Acad. Sci. U.S.A.*, 91, 1994). Of these, at least 70 are currently used for biomedical and agricultural applications. The largest class of bioactive compounds, the polyketides, include a broad range of antibiotics, immunosuppressants and anticancer agents which together account for sales of over $5 billion per year.

Despite the seemingly large number of available bioactive compounds, it is clear that one of the greatest challenges facing modem biomedical science is the proliferation of antibiotic resistant pathogens. Because of their short generation time and ability to readily exchange genetic information, pathogenic microbes have rapidly evolved and disseminated resistance mechanisms against virtually all classes of antibiotic compounds. For example, there are virulent strains of the human pathogens *Staphylococcus* and *Streptococcus* that can now be treated with but a single antibiotic, vancomycin, and resistance to this compound will require only the transfer of a single gene, vanA, from resistant *Enterococcus* species for this to occur. (Bateson et al., *System. Appl. Microbiol*, 12, 1989). When this crucial need for novel antibacterial compounds is superimposed on the growing demand for enzyme inhibitors, immunosuppressants and anti-cancer agents it becomes readily apparent why pharmaceutical companies have stepped up their screening of microbial samples for bioactive compounds.

The invention provides methods of identifying a nucleic acid sequence encoding a polypeptide having either known or unknown function. For example, much of the diversity in microbial genomes results from the rearrangement of gene clusters in the genome of microorganisms. These gene clusters can be present across species or phylogenetically related with other organisms.

For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. The gene cluster, the promoter, and additional sequences that function in regulation altogether are referred to as an "operon" and can include up to 20 or more genes, usually from 2 to 6 genes. Thus, a gene cluster is a group of adjacent genes that are either identical or related, usually as to their function.

Some gene families consist of identical members. Clustering is a prerequisite for maintaining identity between genes, although clustered genes are not necessarily identical. Gene clusters range from extremes where a duplication is generated to adjacent related genes to cases where hundreds of identical genes lie in a tandem array. Sometimes no significance is discemable in a repetition of a particular gene. A principal example of this is the expressed duplicate insulin genes in some species, whereas a single insulin gene is adequate in other mammalian species.

Further, gene clusters undergo continual reorganization and, thus, the ability to create heterogeneous libraries of gene clusters from, for example, bacterial or other prokaryote sources is valuable in determining sources of novel proteins, particularly including enzymes such as, for example, the polyketide synthases that are responsible for the synthesis of polyketides having a vast array of useful activities. Other types of proteins that are the product(s) of gene clusters are also contemplated, including, for example, antibiotics, antivirals, antitumor agents and regulatory proteins, such as insulin.

As an example, polyketide synthases enzymes fall in a gene cluster. Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of a huge variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

The ability to select and combine desired components from a library of polyketides and postpolyketide biosynthesis genes for generation of novel polyketides for study is appealing. The method(s) of the present invention make it possible to, and facilitate the cloning of, novel polyketide synthases, since one can generate gene banks with clones containing large inserts (especially when using the f-factor based vectors), which facilitates cloning of gene clusters.

For example, a gene cluster can be ligated into a vector containing an expression regulatory sequences which can control and regulate the production of a detectable protein or protein-related array activity from the ligated gene clusters. Use of vectors which have an exceptionally large capacity for exogenous nucleic acid introduction are particularly appropriate for use with such gene clusters and are described by way of example herein to include the f-factor (or fertility factor) of *E. coli*. This f-factor of *E. coli* is a plasmid which affects high-frequency transfer of itself during conjugation and is ideal to achieve and stably propagate large nucleic acid fragments, such as gene clusters from mixed microbial samples.

The nucleic acid isolated or derived from these samples (e.g., a mixed population of microorganisms) can preferably be inserted into a vector or a plasmid prior to screening of the polynucleotides. Such vectors or plasmids are typically those containing expression regulatory sequences, including promoters, enhancers and the like.

Accordingly, the invention provides novel systems to clone and screen mixed populations of organisms present, for example, in an environmental samples, for polynucleotides encoding molecules having an activity of interest, enzymatic activities and bioactivities of interest in vitro. The method(s) of the invention allow the cloning and discovery of novel bioactive molecules in vitro, and in particular novel bioactive molecules derived from uncultivated or cultivated samples. Large size gene clusters, genes and gene fragments can be cloned, sequenced and screened using the method(s) of the invention. Unlike previous strategies, the method(s) of the invention allow one to clone screen and identify polynucleotides and the polypeptides encoded by these polynucleotides in vitro from a wide range of environmental samples.

The invention allows one to screen for and identify polynucleotide sequences from complex environmental samples. DNA libraries created from these samples can be obtained from cell free samples, so long as the sample contains nucleic acid sequences, or from samples containing cellular organisms or viral particles. The organisms from which the libraries may be prepared include prokaryotic microorganisms, such as *Eubacteria* and *Archaebacteria*, lower eukaryotic microorganisms such as fungi, algae and protozoa, as well as mixed populations of plants, plant spores and pollen. The organisms may be cultured organisms or uncultured organisms obtained from environmental samples and includes extremophiles, such as thermophiles, hyperthermophiles, psychrophiles and psychrotrophs.

Sources of nucleic acids used to construct a DNA library can be obtained from environmental samples, such as, but not limited to, microbial samples obtained from Arctic and Antarctic ice, water or permafrost sources, materials of volcanic origin, materials from soil or plant sources in tropical areas, droppings from various organisms including mammals, invertebrates, as well as dead and decaying matter etc. Thus, for example, nucleic acids may be recovered from either a cultured or non-cultured organism and used to produce an appropriate DNA library (e.g., a recombinant expression library) for subsequent determination of the identity of the particular polynucleotide sequence or screening for enzyme or biological activity.

The following outlines a general procedure for producing libraries from both culturable and non-culturable organisms as well as mixed population of organisms, which libraries can be probed, sequenced or screened to select therefrom nucleic acid sequences having an identified, desired or predicted biological activity (e.g., an enzymatic activity).

As used herein an environmental sample is any sample containing organisms or polynucleotides or a combination thereof. Thus, an environmental sample can be obtained from any number of sources (as described above), including, for example, insect feces, hot springs, soil and the like. Any source of nucleic acids in purified or non-purified form can be utilized as starting material. Thus, the nucleic acids may be obtained from any source which is contaminated by an organism or from any sample containing cells. The environmental sample can be an extract from any bodily sample such as blood, urine, spinal fluid, tissue, vaginal swab, stool, amniotic fluid or buccal mouthwash from any mammalian organism. For non-mammalian (e.g., invertebrates) organisms the sample can be a tissue sample, salivary sample, fecal material or material in the digestive tract of the organism. An environmental sample also includes samples obtained from extreme environments including, for example, hot sulfur pools, volcanic vents, and frozen tundra. The sample can come from a variety of sources. For example, in horticulture and agricultural testing the sample can be a plant, fertilizer, soil, liquid or other horticultural or agricultural product; in food testing the sample can be fresh food or processed food (for example infant formula, seafood, fresh produce and packaged food); and in environmental testing the sample can be liquid, soil, sewage treatment, sludge and any other sample in the environment which is considered or suspected of containing an organism or polynucleotides.

When the sample is a mixture of material (e.g., a mixed population of organisms), for example, blood, soil or sludge, it can be treated with an appropriate reagent which is effective to open the cells and expose or separate the strands of nucleic acids. Although not necessary, this lysing and nucleic acid denaturing step will allow cloning, amplification or sequencing to occur more readily. Further, if desired, the mixed population can be cultured prior to analysis in order to purify a particular population and thus obtaining a purer sample. This is not necessary, however. For example, culturing of organisms in the sample can include culturing the organisms in microdroplets and separating the cultured microdroplets with a cell sorter into individual wells of a multi-well tissue culture plate.

Accordingly, the sample comprises nucleic acids from, for example, a diverse and mixed population of organisms (e.g., microorganisms present in the gut of an insect). Nucleic acids are isolated from the sample using any number of methods for DNA and RNA isolation. Such nucleic acid isolation methods are commonly performed in the art. Where the nucleic acid is RNA, the RNA can be reversed transcribed to DNA using primers known in the art. Where the DNA is genomic DNA, the DNA can be sheared using, for example, a 25 gauge needle.

The nucleic acids are then cloned into an appropriate vector. The vector used will depend upon whether the DNA is to be expressed, amplified, sequenced or manipulated in any number of ways known in the art (see, for example, U.S. Pat. No. 6,022,716 which discloses high throughput sequencing vectors). Cloning techniques are known in the art or can be developed by one skilled in the art, without undue experimentation. The choice of a vector will also depend on the size of the polynucleotide sequence and the host cell to be employed in the methods of the invention. Thus, the vector used in the invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are typically used where the specific nucleic acid sequence to be analyzed or modified is large because these vectors are able to stably propagate large polynucleotides.

The vector containing the cloned DNA sequence can then be amplified by plating (i.e., clonal amplification) or transfecting a suitable host cell with the vector (e.g., a phage on an *E. coli* host). Alternatively (or subsequent to amplification), the cloned DNA sequence is used to prepare a library for screening by transforming a suitable organism. Hosts, known in the art are transformed by artificial introduction of the vectors containing the target nucleic acid by inoculation under conditions conducive for such transformation. One could transform with double stranded circular or linear nucleic acid or there may also be instances where one would transform with single stranded circular or linear nucleic acid sequences. By transform or transformation is meant a permanent or transient genetic change induced in a cell following incorporation of new DNA (e.g., DNA exogenous to the cell). Where the cell is a mammalian cell, a permanent genetic change is generally achieved by introduction of the DNA into the genome of the cell. A transformed cell or host cell generally refers to a cell (e.g., prokaryotic or eukaryotic) into which (or into an ancestor of which) has been introduced, by means of recombinant DNA techniques, a DNA molecule not normally present in the host organism.

A particularly type of vector for use in the invention contains an f-factor origin replication. The f-factor (or fertility factor) in *E. coli* is a plasmid which effects high frequency transfer of itself during conjugation and less frequent transfer of the bacterial chromosome itself. In a particular embodiment cloning vectors referred to as "fosmids" or bacterial artificial chromosome (BAC) vectors are used. These are derived from *E. coli* f-factor which is able to stably integrate large segments of DNA. Accordingly, the vectors make it possible to integrate large genomic fragments in the form of a stable "environmental DNA library."

The nucleic acids derived from a mixed population or sample may be inserted into the vector by a variety of procedures. In general, the nucleic acid sequence is inserted into an appropriate restriction endonuclease site(s) by procedures known in the art. Such procedures and others are deemed to be within the scope of those skilled in the art. A typical cloning scenario may have the DNA "blunted" with an appropriate nuclease (e.g., Mung Bean Nuclease), methylated with, for example, EcoR I Methylase and ligated to EcoR I linkers GGAATTCC (SEQ ID NO: 1). The linkers are then digested with an EcoR I Restriction Endonuclease and the DNA size fractionated (e.g., using a sucrose gradient). The resulting size fractionated DNA is then ligated into a suitable vector for sequencing, screening or expression (e.g., a lambda vector and packaged using an in vitro lambda packaging extract).

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, methods of transfection or transformation with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). The eukaryotic cell may be a yeast cell (e.g., *Saccharomyces cerevisiae*), an insect cell (e.g., *Drosophila* sp.) or may be a mammalian cell, including a human cell.

Eukaryotic systems, and mammalian expression systems, allow for post-translational modifications of expressed mammalian proteins to occur. Eukaryotic cells which possess the cellular machinery for processing of the primary transcript, glycosylation, phosphorylation, and, advantageously secretion of the gene product should be used. Such host cell lines may include, but are not limited to, CHO, VERO, BHK, HeLa, COS, MDCK, Jurkat, HEK-293, and WI38.

In one embodiment, once a library of clones is created using any number of methods, including those describe above, the clones are resuspended in a liquid media, for example, a nutrient rich broth or other growth media known in the art. Typically the media is a liquid media which can be readily pipetted. One or more media types containing at least one clone of the library is then introduced either individually or together as a mixture, into capillaries (all or a portion thereof) in a capillary array. The capillary array (e.g., an array of from about 100, 1000, 2000, 4000, 5000, 10,000, 20,000, 40,000, 50,000, 100,000 to about 4,000,000 capillary tubes) can be incubated and used to screen cells, samples or compound in each capillary tube for an activity, molecule or compound of interest. If an activity, molecule or compound of interest is identified, the contents of the capillary tube in the array can be aspirated and further cultured, screened, cloned or sequenced.

In another embodiment, the library is first biopanned prior to introduction or delivery into a capillary. Such biopanning methods enrich the library for sequences or activities of interest. Examples of methods for biopanning or enrichment are described below.

In one embodiment, the library can be screened or sorted to enrich for clones containing a sequence or activity of interested based on polynucleotide sequences present in the sample. Thus, the invention provides methods and compositions useful in screening organisms for a desired biological activity or biological sequence and to assist in obtaining sequences of interest that can further be used in directed evolution, molecular biology, biotechnology and industrial applications.

Accordingly, the invention provides methods to rapidly screen, enrich and identify sequences in a sample by screening and identifying the nucleic acid sequences present in the sample. Thus, the invention increases the repertoire of available sequences that can be used for the development of diagnostics, therapeutics or molecules for industrial applications. Accordingly, the methods of the invention can identify novel nucleic acid sequences encoding proteins or polypeptides having a desired biological activity.

Biopanning

After the libraries have been generated one can include the additional step of "biopanning" such libraries prior to expression screening. The "biopanning" procedure refers to a process for identifying clones having a specified biological activity by screening for sequence homology in a library of clones.

The probe DNA used for selectively interacting with the target DNA of interest in the library can be a full-length coding region sequence or a partial coding region sequence of DNA for an known bioactivity. The original DNA library can be probed using mixtures of probes comprising at least a portion of the DNA sequence encoding a known bioactivity having a desired activity. These probes or probe libraries are preferably single-stranded. The probes that are particularly suitable are those derived from DNA encoding bioactivities having an activity similar or identical to the specified bioactivity which is to be screened.

In another embodiment, in vivo biopanning may be performed utilizing a FACS-based machine or the capillary array system of the present invention. DNA libraries are constructed with vectors which contain elements which stabilize transcribed RNA. For example, the inclusion of sequences which result in secondary structures such as hairpins which are designed to flank the transcribed regions of the RNA would serve to enhance their stability, thus increasing their half life within the cell. The probe molecules used in the biopanning process consist of oligonucleotides labeled with reporter molecules that only fluoresce upon binding of the probe to a target molecule. Various dyes or stains well known in the art, for example those described in "Practical Flow Cytometry", 1995 Wiley-Liss, Inc., Howard M. Shapiro, M.D., can be used to intercalate or associate with nucleic acid in order to "label" the oligonucleotides. These probes are introduced into the recombinant cells of the library using one of several transformation methods. The probe molecules interact or hybridize to the transcribed target mRNA or DNA resulting in DNA/RNA heteroduplex molecules or DNA/DNA duplex molecules. Binding of the probe to a target will yield a fluorescent signal which is detected and sorted by the FACS machine during the screening process.

The probe DNA should be at least about 10 bases and preferably at least 15 bases. In one embodiment, an entire coding region of one part of a pathway may be employed as a probe. Where the probe is hybridized to the target DNA in an in vitro system, conditions for the hybridization in which target DNA is selectively isolated by the use of at least one DNA probe will be designed to provide a hybridization stringency of at least about 50% sequence identity, more particularly a stringency providing for a sequence identity of at least about 70%, 80%, 90% or 95%.

Hybridization techniques for probing a microbial DNA library to isolate target DNA of potential interest are well known in the art and any of those which are described in the literature are suitable for use herein.

The resultant libraries of transformed clones are then screened for clones which display an activity of interest. Clones can be shuttled in alternative hosts for expression of active compounds, or screened using methods described herein.

An alternative to the in vivo biopanning described above is an encapsulation techniques such as gel microdroplets, which may be employed to localize multiple clones in one location to be screened on a FACS machine for positive expressing clones within the group of clones which can then be broken out into individual clones to be screened again on a FACS machine or on the capillary array system of the present invention to identify positive individual clones. Screening on a FACS machine is described in patent application Ser. No. 08/876,276 filed Jun. 16, 1997.

Further, it is possible to combine some or all of the above embodiments such that a normalization step is performed prior to generation of the expression library, the expression library is then generated, the expression library so generated is then biopanned, and the biopanned expression library is then screened using a high throughput cell sorting and screening instrument. Thus there are a variety of options, including: (i) generating the library and then screen it; (ii) normalize the target DNA, generate the expression library and screen it; (iii) normalize, generate the library, biopan and screen; or (iv) generate, biopan and screen the library.

The gel microdroplet technology has had significance in amplifying the signals available in flow cytometric analysis, and in permitting the screening of microbial strains in strain improvement programs for biotechnology. Wittrup et al., (Biotechnol.Bioeng., 42: 351–356, 1993) developed a microencapsulation selection method which allows the rapid and quantitative screening of >$10^6$ yeast cells for enhanced secretion of *Aspergillus awamori* glucoamylase. The method provides a 400-fold single-pass enrichment for high-secretion mutants.

Gel microdroplet or other related technologies can be used in the present invention to localize, sort, and amplify signals in the high throughput screening of recombinant libraries. Cell viability during the screening is not an issue or concern since nucleic acid can be recovered from the microdroplet.

Different types of encapsulation strategies and compounds or polymers can be used with the present invention. For instance, high temperature agaroses can be employed for making microdroplets stable at high temperatures, allowing stable encapsulation of cells subsequent to heat kill steps utilized to remove all background activities when screening for thermostable bioactivities.

Following any number of biopanning techniques capable of enriching the library population for clones containing sequences of interest, the enriched clones are suspended in a liquid media such as a nutrient broth or other growth media. Accordingly, the enrich clones comprises a plurality of recombinant clones, which comprise host cells transformed with constructs comprising expression vectors into which have been incorporated nucleic acid sequences derived from a sample. Liquid media containing a subset of clones and one or more substrates (e.g., an enzyme substrate) is then introduced, either individually or together as a mixture, into capillaries in a capillary array. Interaction (including reaction) of the substrate or labeled polynucleotide probe and a clone expressing an enzyme having the desire enzyme activity produces an optically detectable signal, which can be spatially detected to identify one or more capillaries containing at least one signal-producing clone. The signal-producing clones can then be recovered from the identified capillaries.

A "substrate" as used herein includes substrates for the optical detection of enzymes (and their specific enzyme activities). Such substrates are well known in the art. For example, various enzymes and suitable substrates specific for such enzymes are provided in Molecular Probes, Handbook Of Fluorescent Probes and Research Chemical (Molecular Probes, Inc.; Eugene, Oreg.), the disclosure of which is incorporated herein by reference. A suitable substrate for use in the present invention is any substrate that produces an optically detectable signal upon interaction (e.g., reaction) with a give enzyme having a desired activity, or a given clone encoding such enzyme.

One skilled in the art can choose a suitable substrate based on the desired enzyme activity. Examples of desired enzymes/enzymatic activities include those listed herein. A desired enzyme activity may also comprise a group of enzymes in an enzymatic pathway for which there exists an optically detectable substrate or by-product. One example of this is the set of carotenoid synthesis enzymes.

Substrates are known and/or are commercially available for glycosidases, proteases, phosphtases, and monoxygenases, among others. Among the proteases with optically detectable substrates or lay products are the serine proteases—trypsin and chymotrypsin. Among the glucosidases are mannosidase, amylogluconsidase, cellulase, neuraminidase, beta-galactosidase, beta-glucosidase, beta-glucouronidase and alpha-amylase.

Where the desire activity is in the same class as that of other biomolecules or enzymes having a number known substrates, the activity can be examined using a cocktail of known substrates. For example, substrates are known for approximately 20 commercially available esterases and the combination of these known substrate can provide detectable, if not optimal, signal production.

The optical signal substrate can be a chromogenic substrate, a fluorogenic substrate, a bio-or chemiluminescent substrate, or a fluorescence resonance energy transfer (FRET) substrate. The detectable species can be one which results from cleavage of the substrate or a secondary molecule which is so affected by the cleavage or other substrate/biomolecule interaction as to undergo a detectable change. Innumerable examples of detectable assay formats are known from the diagnostic arts which use immunoassay, chromogenic assay, and labeled probe methodologies.

In one embodiment, the optical signal substrate can be a bio- or chemiluminescent substrate. Chemiluminescent substrates for several enzymes are available from Tropix (Bedford, Mass.). Among the enzymes having known chemiluminescent substrates are alkaline phosphatase, beta-galactosidase, beta-glucouronidase, and beta-glucosidase.

In another embodiment, chromogenic substrates may be used, particularly for certain enzymes such as hydrolytic enzymes. For example, the optical signal substrate can be an indolyl derivative, which is enyzmatically cleaved to yield a chromogenic product. Where chromogenic substrate are used, the optically detectable signal is optical absorbance (including changes in absorbance). In this embodiment, signal detection can be provided by an absorbance measurement using a spectrophotometer or the like.

In another embodiment, a fluorogenic substrate is used, such that the optically detectable signal is fluorescence. Fluorogenic substrates provide high sensitivity for improved detection, as well as alternate detection modes. Hydroxy- and amino-substituted coumarins are the most widely used fluorophores used for preparing fluorogenic substrates. A typical coumarin-based fluorogenic substrate is 7-hydroxycoumarin, commonly known as umbelliferone (Umb). Derivatives and analogs of umbelliferone are also used. Substrate based on derivative and analogs of florescein (such as FDG or C12-FDG) and rhodamine are also used. Substrates derived from resorufin (e.g, resorufin beta-D-galactopyranoside or resorufin beta-D-glucuronide) are particularly useful in the present invention. Resorufin-based substrates are useful, for example, in screening for glycosidases, hydrolases and dealkylases. Lipophilic derivates of the foregoing substrates (e.g., alkylated derivatives) may be useful in certain embodiments, since they generally load more readily into cells and may tend to associate with lipid regions of the cell. Fluorescein and resorufin are available commercially as alkylated derivatives that form products that are relatively insoluble in water (i.e., lipophilic). For example, fluorescence imaging can be performed using C12-resorufin galactoside, produced by Molecular Probes (Eugene, Oreg.) as a substrate.

The particular fluorogenic substrate used may be chosen based on the enzymatic activity being screened. For examples:

Lipases/Esterases. When screening for an enzyme having lipase or esterase activity, an acylated derivative of fluorescein in used. The fluorphore is hydrolyzed from the derivative to generate a signal.

Proteases. Enzymes having protease activity can be screened in the same way as the esterases, with an amide bond cleaved instead of an ester. There are now well over 100 different protease substrates available with an acylated fluorophore at the scissile bond. Rhodamine derivatives are generally used.

Monooxygenases (Dealkylases). Several coumarin derivatives suitable as monooxygenase substrates are commercially available. Typically, in these substrates, the hydroxylation of the ethyl group in the compound results in the release of the resorufin fluorophore.

Typically, the substrates are able to enter the cell and maintain a presence within the cell for a period sufficient for analysis to occur (e.g., once the substrate is in the cell it does not "leak" back out before reacting with the enzyme being screened to an extent sufficient to produce a detectable response). Retention of the substrate in the cell can be enhanced by a variety of techniques. In one method, the substrate compound is structurally modified by addition of a hydrophobic (e.g., alkyl) tail. In another embodiment, a solvent, such as DMSO or glycerol, can be used to coat the exterior of the cell. Also the substrate can be administered to the cells at reduced temperature, which has been observed to retard leakage of substrates from cells.

The optical signal substrate can, in some embodiments, be a FRET substrate. FRET is a spectroscopic method that can monitor proximity and relative angular orientation of fluorophores. A fluorescent indicator system that uses FRET to measure the concentration of a substrate or products includes two fluorescent moieties having emission and excitation spectra that render one a "donor" fluorescent moiety and the other an "acceptor" fluorescent moiety. The two fluorescent moieties are chosen such that the excitation spectrum of the acceptor fluorescent moiety overlaps with the emission spectrum of the excited moiety (the donor fluorescence moiety). The donor moiety is excited by light of appropriate intensity within the excitation spectrum of the donor moiety and emits the absorbed energy as fluorescent light. When the acceptor fluorescent protein moiety is positioned to quench the donor moiety in the excited state, the fluorescence energy is transferred to the acceptor moiety, which can emit a second photon. The emission spectra of the donor and acceptor moieties have minimal overlap so that the two emissions can be distinguished. Thus, when acceptor emits fluorescence at longer wavelength that the donor, then the net steady state effect is that the donor's emission is quenched, and the acceptor now emits when excited at the donor's absorption maximum.

The optical signal can be measured using, for example, a fluoremeter (or the like) to detect fluorescence, including fluorescence polarization, time-resolved fluorescence or FRET. In general, excitation radiation, from an excitation source having a first wavelength, causes the excitation radiation to excite the sample. In response, fluorescence compounds in the sample emit radiation having a wavelength that is different from the excitation wavelength. Methods of performing assays on fluorescent materials are well known in the art and are described, e.g., by Lakowicz (Principles of Fluorescence Spectroscopy, New York, Plenum Press, 1983) and Herman ("Resonance energy transfer microscopy," in: Fluorescence Microscopy of Living Cells in Culture, Part B, Methods in Cell Biology, vol. 30, ed. Taylor & Wang, San Diego, Academic Press, 1989, pp. 219–243). Examples of fluorescence detection techniques are described in further detail below.

In addition, several methods have been describe in the literature for using reporter genes to measure gene expression. Nolan et al. describes a technique to analyze beta-galactosidase expression in mammalian cells. This technique employs fluorescein-di-beta-D-glactopyranoside (FDG) as a substrate for beta-galactosidase, which releases fluorescein, a product that can be detected by it fluorescence emission upon hydrolysis (Nolan et al., 1991). Other fluorogenic substrates have been developed, such as 5-dodecanoylamino fluorescein di-beta-D-galactopyranside (C12-FDG) (Molecular Probes), which differs from FDG in that it is a lipophilic fluorescein derivative that can easily cross most cell membranes under physiological culture conditions.

The above-mentioned beta-galactosidase assays may be employed to screen E. coli cells expressing recombinant beta-D-galactosidase isolated, for example, from a hyperthermophilic archaeon such as Sulolobus solfataricus. Other reporter genes may be useful as substrates are known for beta-glucouronidase, alkaline phosphatase, chloramphenicol acetyltransferase (CAT) and luciferase.

Existing screening technology usually relies on two-dimensional wells (e.g., 96-, 384- and 1536-well) plates. The capillary array-based approach of the present invention has numerous advantages over well-based screening techniques, including the elimination of the need for fluid dispensers for dispensing fluids (e.g., reactants) into individual well reservoirs, and the reduced cost per array (e.g., glass capillaries are reusable). In addition, the wave-guide effects of the capillaries in an array constructed with a low refractive index matrix (e.g., the interstitial spaces between the capillary walls in the array are composed of a low refractive index material, such as black glass) can improve optical detectability, since the capillaries act effectively like optical fibers. Moreover, the enzymes screened using two dimensional well plates is typically on the order of about 1 million clone-assays per day using a 1536-well plate with conventional automated screening techniques, while that for a capillary-based approach is as high as about $10^9$ clone-assays per day. In the case of the evaporative/wick cycle approach, the present invention also provides the advantages of the possibility of high temperature (up to about 99° C.) assays and the spatial concentration of detectable products in a very small volume (to improve detection sensitivity). Capillary array-based screening techniques also have advantages over FACS-based assays. For example, capillary array-based screening permits standard liquid-phase assays, long-duration assays, and high temperature assays.

With reference now to FIG. 1, depicted is a capillary array useful in the invention. The capillary array (10) is comprised of a plurality of individual capillaries (20) having at least one outer wall (30) defining a lumen (40). The capillaries (20) of the capillary array (10) are held in close proximity and can be bound together, fused (e.g., where the capillaries are made of glass), glued, bonded, or clamped. The capillary array of the present invention comprises at least about 100 capillaries, or at least about 1,000 capillaries and can exceed about 5,000 capillaries. In one embodiment, the capillary array comprises about 5,000–50,000 capillaries. A typically capillary array can be comprised of about 1,000 capillaries or more (e.g., about 100,000 to about 4,000,000) and have a density of 500 to more than 1,000 (e.g., about 1,500 to 51,000) capillaries per cm$^2$, or about 5 capillaries per mm$^2$. Lower densities are feasible and capable of being made in the art. The capillary array can have, for example, a width (or diameter) of about 0.5–10 mm and a height (or thickness) of about 0.05 to about 10 cm (more preferably about 0.1 to about 5 cm). The ratio of height to width is typically at least about 1.

A capillary (20) is depicted in FIG. 1 as having at least one wall (30) and a lumen (40) having an internal diameter of 200 μm and a length of 1 cm. One of skill in the art will recognize that modifications can be made to the volume or dimensions of the invention without departing from the spirit and scope of the present invention. For example, a capillary having an internal diameter of 200 μm and a length of 1 cm has a volume of about 0.3 μl. This volume can be modified by changing the length (e.g., increasing or decreasing the length) or the interior diameter (e.g., increasing or decreasing the interior diameter) or both. The volume desired will depend upon a number of factors which can be empirically determined. Such factors include, for example, the number and size of the cell to be introduced into a capillary tube (20). A volume sufficient to introduce 1 or about 1–10 cells per capillary is desirable. The individual capillaries in the capillary array typically have an inner diameter (I.D.) of about 10–500 microns; and more preferably about 50–200 microns. In the embodiment depicted in FIG. 1 a volume of 0.3 μl is sufficient to allow introduction of about 1 to 10 cells. The number of cells can be easily varied by dilution of the cell culture prior to wicking of the culture by the capillary tubes. It will be recognized that the outer wall (30) of capillary (20) can be one or more walls fused together. Similarly, the wall can define a lumen (40) that is cylindrical, square, hexagonal or any other geometric shape so long as the walls form a lumen for retention of a liquid or sample.

The capillaries in the array can be formed by a variety of methods including, but not limited to, UV excimer laser ablation/drilling/machining, differential glass etching techniques, drawing of hollow glass tubes, silicon lithography, micro-wire EDM, mechanical drilling, electrochemical methods, and selective chemical or charged-particle etching techniques.

Figure 2:
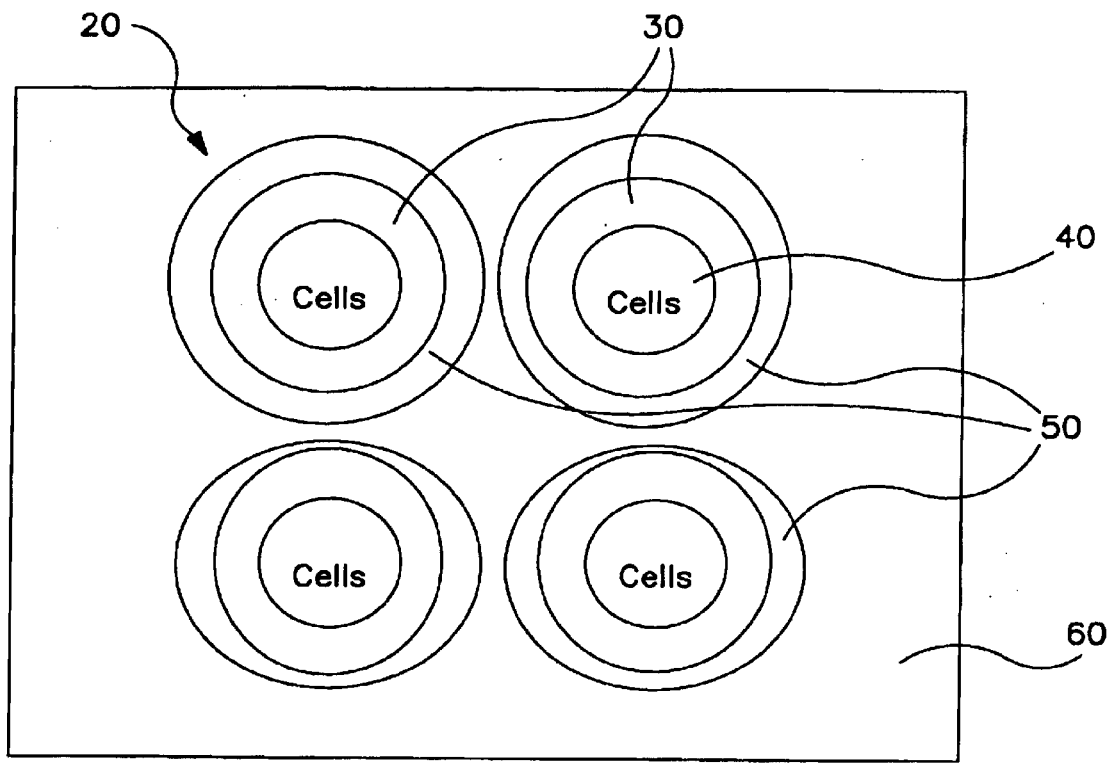
FIG. 2 shows a cross section of a capillary and capillary array. The cross section depicts the lumen of the capillary, labeled as "cells", the sleeve glass of the capillary and the EMA black glass. Also depicted is a cross section a capillary array depicting a plurality of capillary tubes.

FIG. 2 shows a horizontal cross section of a capillary and capillary array of the invention. Capillary (20) is shown having at least one cylindrical wall (30), a lumen (40), a second exterior wall (50), and interstitial material (60) separating the capillary tubes in the array (10). In this embodiment, the cylindrical wall (30) is comprised of a sleeve glass, while exterior wall (50) is comprised of black EMA glass. Lumen (40) is of sufficient size to allow introduction of one or more cells.

The capillary array may be formed from a number of suitable materials such as, for example, metal, glass, semiconductors, (e.g., silicon), quartz, ceramics, as well as various polymers and plastics including, among others, polyethylene, polystyrene, and polypropylene. The internal walls of the capillary array (or portions thereof) may also be coated or functionalized to modify their surface properties. For example, the hydrophilicity/hydrophobicity may be altered to promote or reduce wicking or capillary action, respectively. In addition, the internal walls (or portions thereof) may be silanized or coated with e.g., TEFLON, to prevent sticking of cells, nucleic acids, and other biological materials to the capillary walls. Other coating or functionalizing materials include, for example, ligands such as avidin, streptavidin, antibodies, antigens, and other molecules having specific binding affinity. Typically a material that can withstand repeated sterilization at high-temperatures is used. Preferably the material is glass. The second wall (50) can be made of any material that reduces the "cross-talk" or diffusion of light between adjacent capillary tubes. Such materials include a metal sheath surrounding each capillary, opaque glass or plastics and the like.

Figure 3:
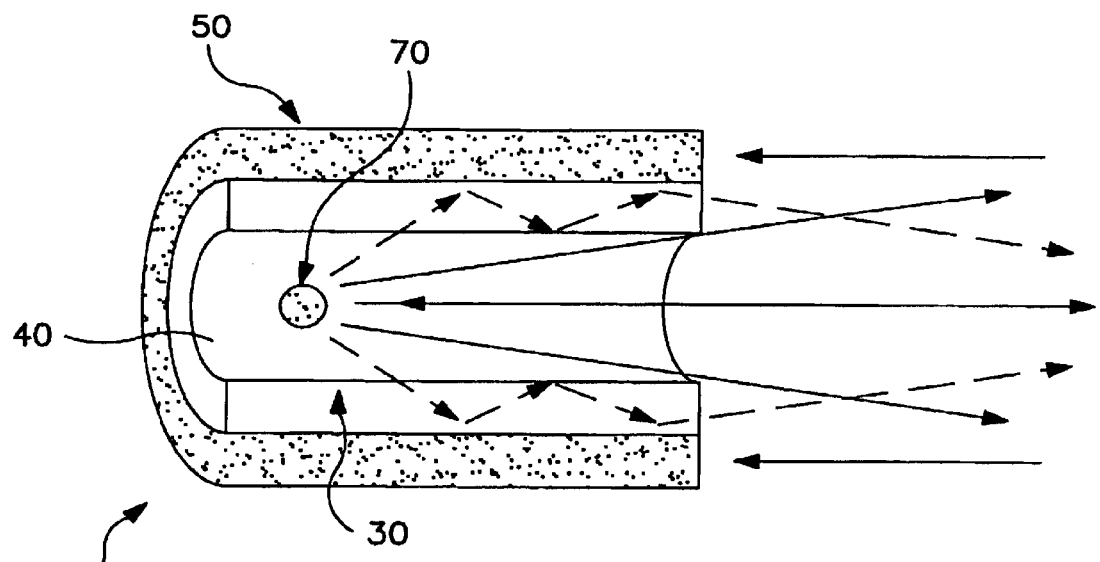
FIG. 3 is a schematic depicting the excitation and emission of a light from a sample within the capillary lumen.

FIG. 3 depicts a vertical cross-section of a capillary of the invention. Depicted is capillary (20) having a first wall (30) and a second wall of black EMA glass (50) defining a lumen (40). A cell, clone or molecule (70) is depicted within the lumen (40). During use an excitation light is directed into the lumen (40) contacting the cell, clone or molecule (70) and exciting a reporter fluorescent material causing emission of light. The emitted light travels the length of the capillary until it reaches a detector. One advantage of the present invention is that the excitation light and emitted light cannot cross contaminate adjacent capillary tubes in a capillary array due to the black EMA glass (50). In addition, the black EMA glass refracts and directs the emitted light towards either end of the capillary tube thus increasing the signal detected by an optical detector (e.g., a CCD camera and the like).

Figure 4:
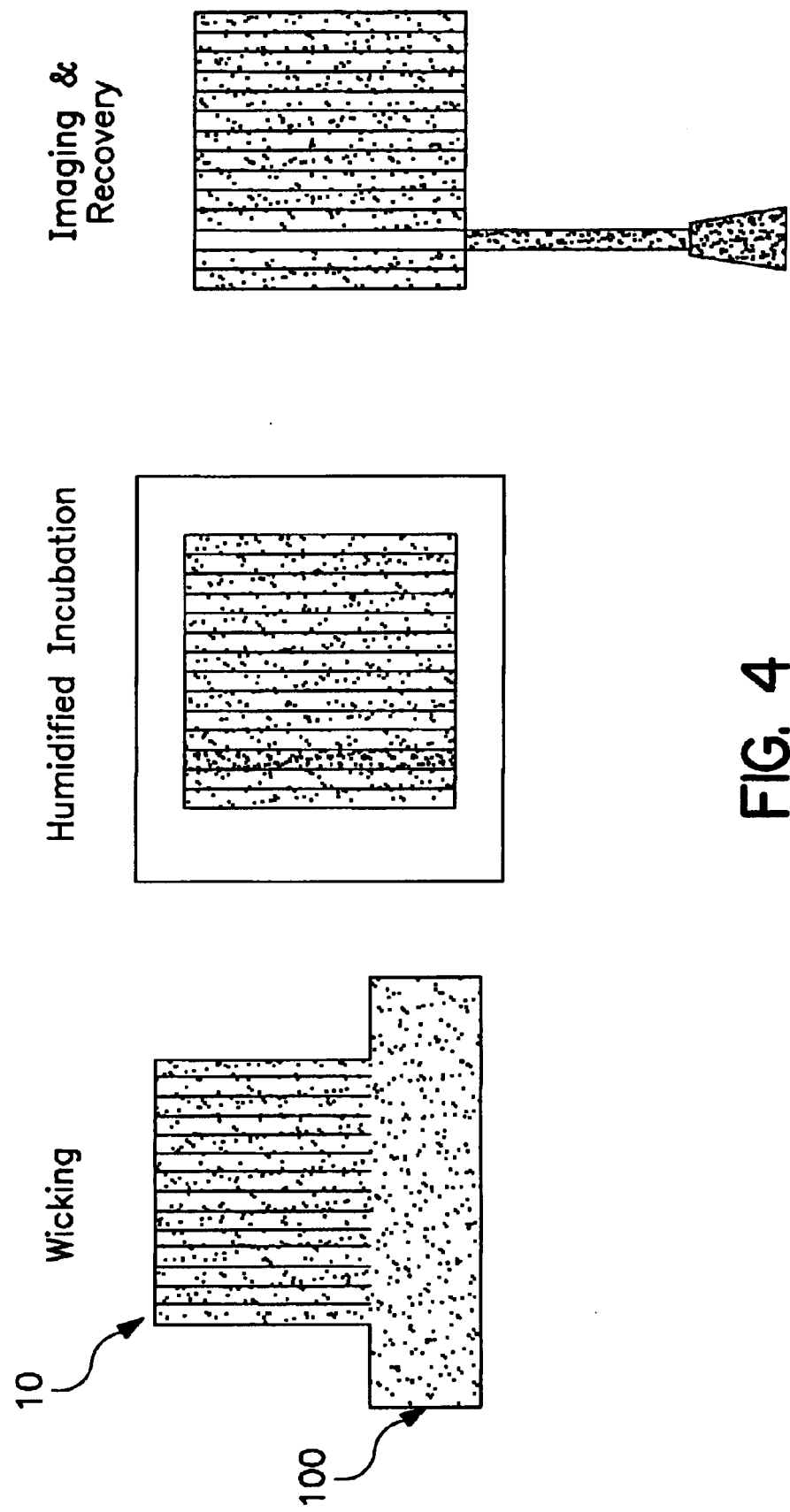
FIG. 4 illustrates an embodiment of the invention in which a capillary array is wicked by contacting a sample containing cells, and humidified in a humidified incubator followed by imaging and recovery of cells in the capillary array.
Figure 7A:
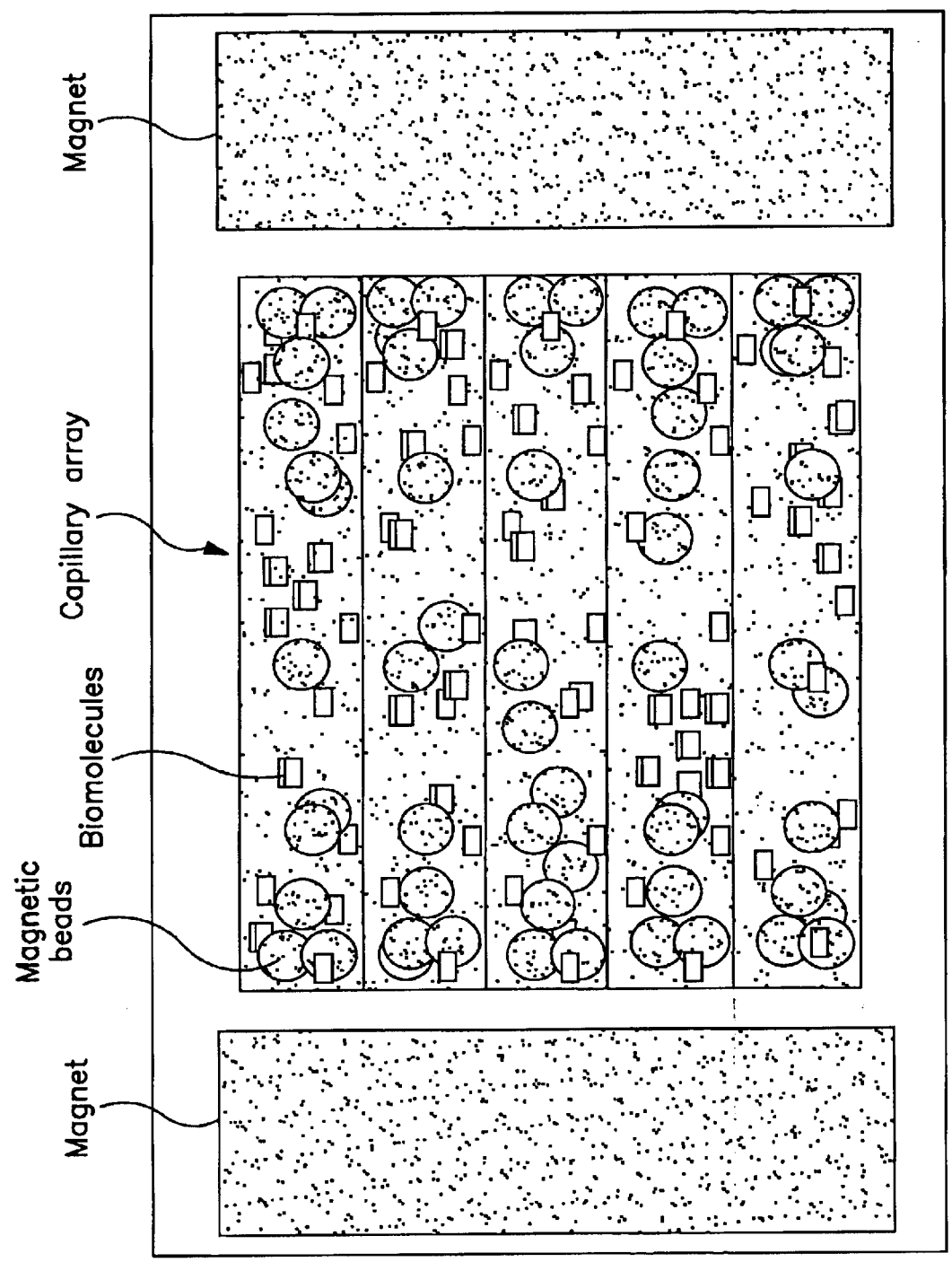
FIG. 7A is a depiction of capillary tubes containing paramagnetic beads and cells.
Figure 7B:
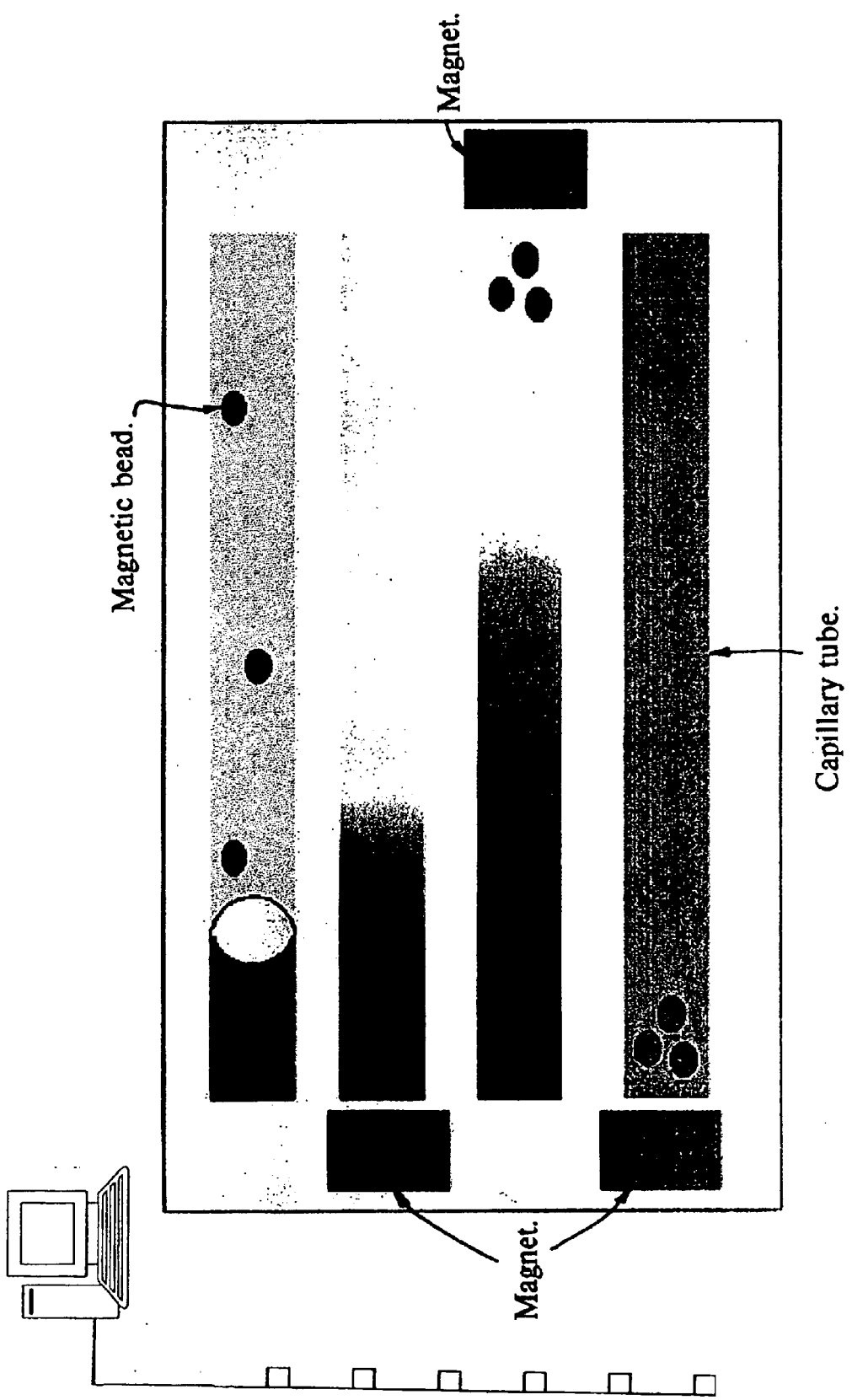
FIG. 7B is a depiction on the use of the paramagnetic beads to stir a sample in a capillary tube. Magnets are alternated between opposite ends of the capillary tube to effectuate movement of the paramagnetic beads from one end of the tube to the other.

FIG. 4 depicts a method of using a capillary array of the invention. In this depiction, capillary array (10) is immersed or contacted with a container (100) containing cells, clones, molecules or compounds suspended in media. The media and cells are then wicked up the capillary tubes by capillary action. The natural wicking that occurs as a result of capillary forces obviates the need for pumping equipment and liquid dispensers. Substrates, as described above, for measuring biological activity (e.g., enzyme activity) can be contacted with the cells either before or after introduction of the cells into the capillaries in the capillary array. The substrate and at least a subset of the clones can be introduced simultaneously into capillaries in the capillary array by placing open ends of the capillaries in a reservoir containing a mixture of the substrate and clones. Alternatively, a solution of cells may be wicked into the capillaries before the capillary array is placed in a reservoir containing substrate, where the substrate is then wicked into the capillaries that already contain the cells to be screened for the desired activity. As depicted in FIGS. 7A and 7B, and discussed more fully below, various methods can be used to mix or stir the substrate with the cells present in the capillaries including, for example, pareamagnetic beads.

The substrate solution can then be incubated with the cells for a period of time and at an appropriate temperature necessary for cell growth and, for example, to allow the substrate to permeabilize the cell membrane to produce an optically detectable signal or for a period of time and temperature for optimum enzymatic activity. The incubation can be performed, for example, by placing the capillary array in a humidified incubator or at ambient temperature in an apparatus containing a water source to ensure reduced evaporation within the capillary tubes. The evaporative flow rate may be reduced by increasing the humidity (e.g., by placing the capillary array in a humidified chamber). The evaporation rate can also be reduced by capping the capillaries with an oil, wax, membrane or the like. Alternatively, a high molecular weight fluid such as various alcohols, or molecules capable of forming a molecular monolayer, bilayers or other thin films (e.g., fatty acids), or various oils (e.g., mineral oil) can be used to reduce evaporation.

The concentration ranges for substrate solutions will vary according to the substrate utilized. Commercially available substrates will generally contain instructions on concentration ranges to be utilized in, for example, cell staining. These ranges may be employed in the determination of an optimal concentration or concentration range to be utilized in the present invention. Such determination is within the ability of one of skill in the art.

In one embodiment, a first fluid containing cells or clones is wicked into the capillary until only about 50% of the capillary is filled. A small air-bubble is then introduced into the capillary. The air-bubble can be introduced by any number of means including, for example, contacting the capillary with a compositions that creates a seal at the capillary opening on the opposite end of the capillary and then removing the composition thereby causing a vacuum to move the fluid further into the capillary. The capillary or capillary array is then contacted with a second fluid, typically a substrate. The second fluid may contain paramagnetic beads or particles in addition to any substrate. The second fluid is then wicked into the capillary or capillary array and is separated from the fluid containing the cell or clone by the air-bubble. The capillary or capillary array can then be incubated for a period of time to allow the first and second media to reach optimal temperature or for sufficient time to allow cell growth or for sufficient time to allow the first and second media to reach the same temperature. The air-bubble separating the two media types can be disrupted to allow mixing of the media and enzymatic activity. In one embodiment, paramagnetic beads are used to disrupt and/or mix the contents of the capillary tube or capillary array. For example, FIGS. 7A and 7B depicts an embodiment of the invention in which paramagnetic beads are magnetically attracted from one area of the capillary or capillary array to another area of the capillary or capillary array. The paramagnetic beads are attracted by electric or magnetic fields produced at various locations around the capillary or capillary array. Accordingly, alternating an electrical field or magnetic field having a polarity opposite that of the paramagnetic beads from one end of a capillary to another would cause the paramagnetic beads to move within the capillary causing movement of the fluid within the capillary.

In another embodiment, recombinant clones containing a reporter construct or a substrate are wicked into the capillary tubes of the capillary array. In this embodiment, it is not necessary to add a substrate as the reporter construct or substrate contained in the clone can be readily detected using techniques known in the art. For example, a clone containing a reporter construct such as green fluorescent protein can be detected by exposing the clone or substrate within the clone to a wavelength of light that induces fluorescence. Such reporter constructs can be implemented to respond to various culture conditions or upon exposure to various physical stimuli (including light and heat). In addition, various compounds can be screen in a sample using similar techniques. For example, a compound detectably labeled with a florescent molecule can be readily detected within a capillary tube of a capillary array.

The capillary or capillary array is analyzed for identification of capillaries having a detectable signal, such as an optical signal (e.g., fluorescence), by a detector capable of detecting a change in light production or light transmission, for example. Spatial and light detection may be performed using a fluorescence excitation beam that directs light through each of the capillaries in the array, and a photodetector (e.g., a photodiode array, charge-coupled device (CCD), or charge injection device (CID)). The light generated by, for example, enzymatic activation of a fluorescent substrate is detected by an appropriate light detector or detectors positioned adjacent to the apparatus of the invention. The light detector may be, for example, film, a photomultiplier tube, photodiode, avalanche photo diode, CCD or other light detector or camera. The light detector may be a single detector to detect sequential emissions or may be plural to detect and spatially resolve simultaneous emissions at single or multiple wavelengths of emitted light. The light emitted and detected may be visible light or may be emitted as non-visible radiation such as infrared or ultraviolet radiation. The detector or detectors may be stationary or movable. The emitted light or other radiation may be conducted to the detector or detectors by means of lenses, mirrors and fiberoptic light guides or light conduits (single, multiple, fixed, or moveable) positioned on or adjacent to at least one surface of the capillary array.

The photodetector preferably comprises a CCD, CID or an array of photodiode elements that correspond in positions to the capillaries. Position detection of one or more capillaries having an optical signal is then determined from the optical input from each element. Alternatively, the array may be scanned by a scanning confocal or phase-contrast fluorescence microscope or the like, where the array is, for example, carried on a movable stage for movement in a X-Y plane as the capillaries in the array are successively aligned with the beam to determine the capillary array positions at which an optical signal is detected. A CCD camera or the like can be used in conjunction with the microscope. The detection system is preferably computer-automated for rapid screening and recovery.

Where a chromogenic substrate is used, the change in the absorbance spectrum can be measured using a calorimeter, spectrophotometer or the like. Such calorimetric measurements are usually difficult when dealing with a low-volume liquid because the optical path length is short. However, the capillary approach of the present invention permits small volumes of liquid to have long optical path lengths (e.g., longitudinally along the capillary tube), thereby providing the ability to measure absorbance changes using conventional techniques.

In another embodiment, bioactivity or biomolecule or compound is detected by using various electromagnetic detection devices, including, for example, optical, magnetic and thermal detection. In yet another embodiment, radioactivity can be detected within a capillary tube using detection methods known in the art. The radiation can be detected at either end of the capillary tube. For example, where radiation is to be detected the capillary tubes in the capillary array can be separated by plexi-glass or lead rather than a material having a low refractive index.

Recovery of putative hits (cells or clones producing a detectable or optical signal) can be facilitated by using position feedback from the detection system to automate positioning of a recovery device (e.g., a needle pipette tip or capillary tube). FIG. 5 shows an example of a recovery system of the invention. In this example, a needle is guided to a capillary containing a "hit" by overlapping the tip of the needle with the capillary containing the "hit" in the X-Y plane. Once the needle is in alignment with the capillary containing the "hit" the needle is moved along the Z plane until the tip of the needle engages the capillary opening. In order to avoid damage to the capillary itself the needle may be attached to a spring or be of a material that flexes. Once in contact with the opening of the capillary the sample can be aspirated or expelled from the capillary.

The sample can be expelled by, for example, injecting a blast of inert gas into the capillary and collecting the ejected sample in a collection device at the opposite end of the capillary. The diameter of the collection device can be larger than or equal to the diameter of the capillary. The collected sample can then be further processed by, for example, extracting polynucleotides, proteins or by growing the clone in culture.

Figure 5B:
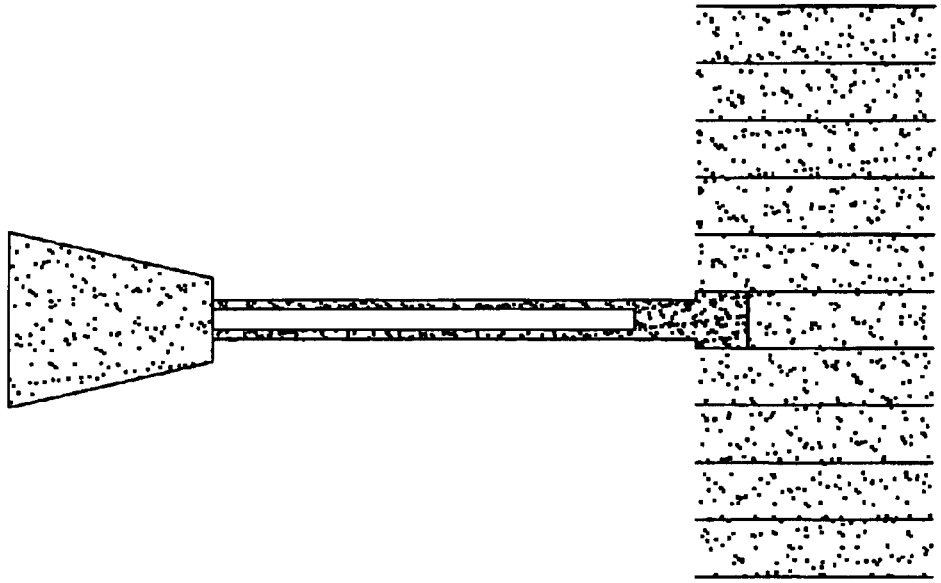
FIG. 5B illustrates a "sloppy" recovery in which the recovery device has an outer diameter greater than the inner diameter of the capillary from which one or more signal-producing clones is being recovered.
Figure 5A:
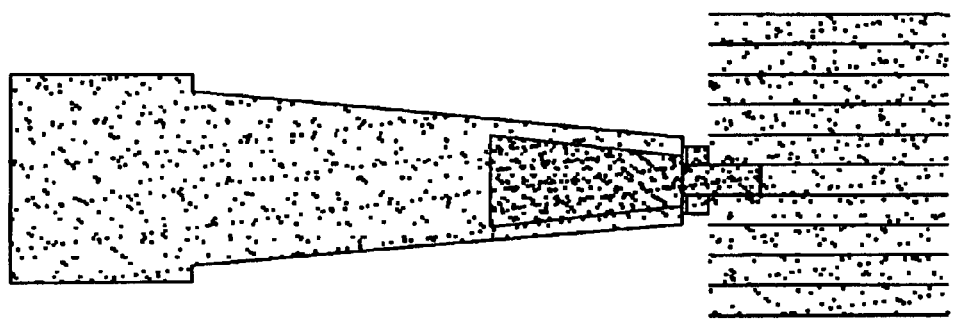
FIG. 5A illustrates one example of a cell recovery technique useful for recovering a sample from a capillary array. In this depiction a needle is contacted with a capillary containing a sample to be obtained. A vacuum is created to evacuate the sample from the capillary tube and onto a filter.
Figure 5C:
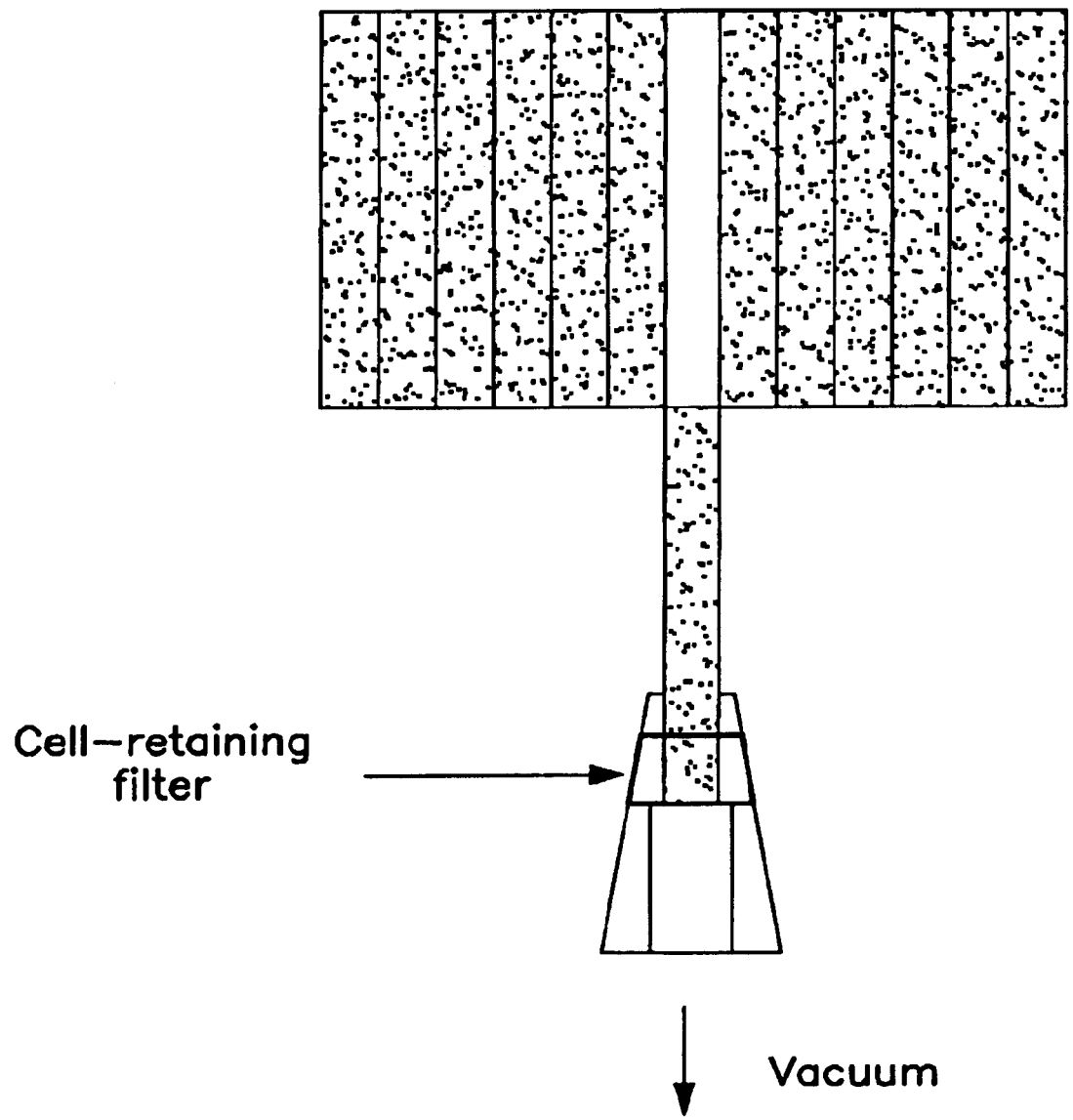
FIG. 5C illustrates "precise" recovery in which the recovery device has an outer diameter approximately equal to or less than the inner diameter of the capillary.
Figure 5D:
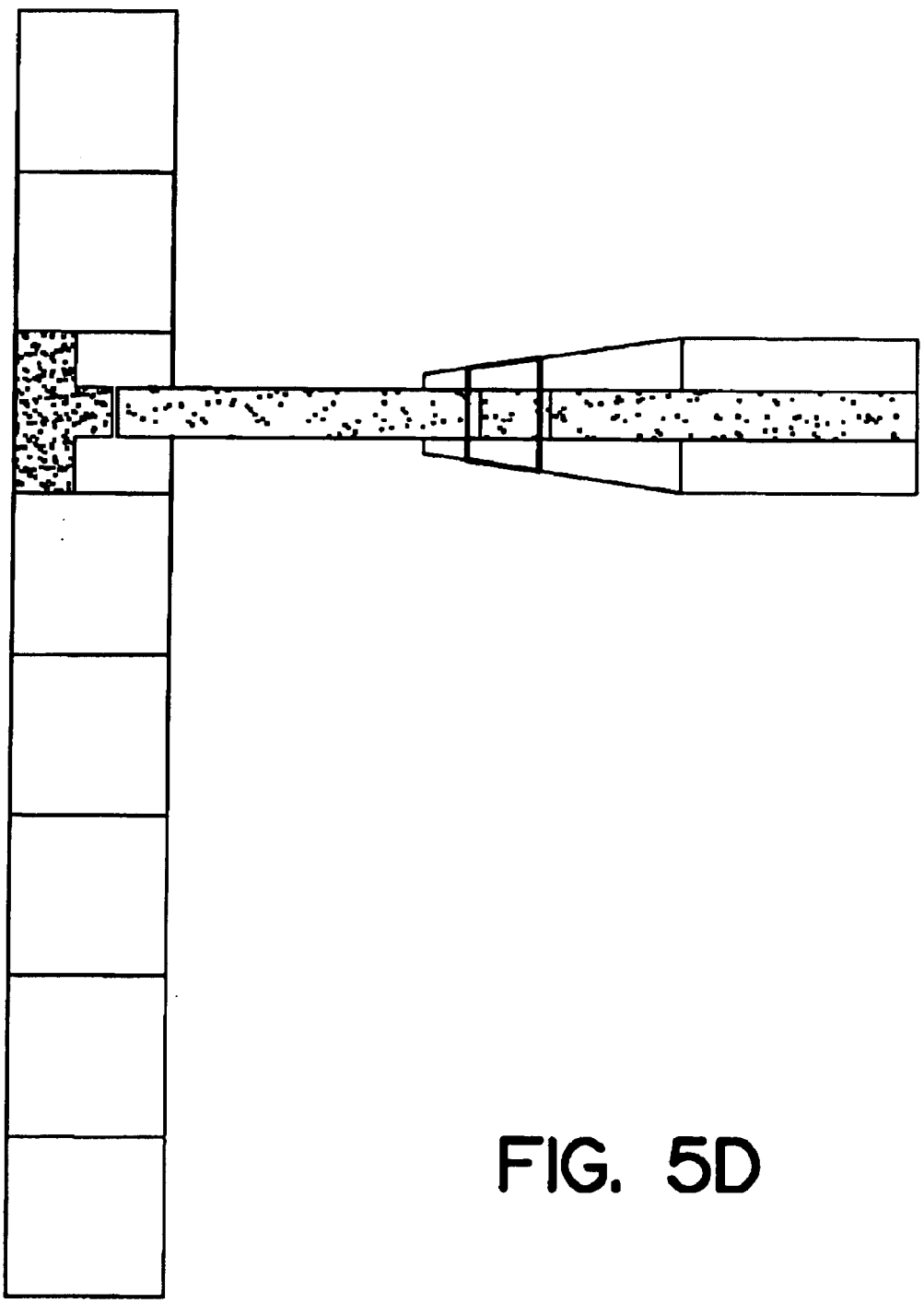
FIG. 5D shows the further processing of the sample once evacuated from the capillary. The sample on the filter from FIGS. 5A–C above is delivered into a multi-well tissue culture plate by reversing the flow of the vacuum or by pumping media through the filter.
Figure 6:
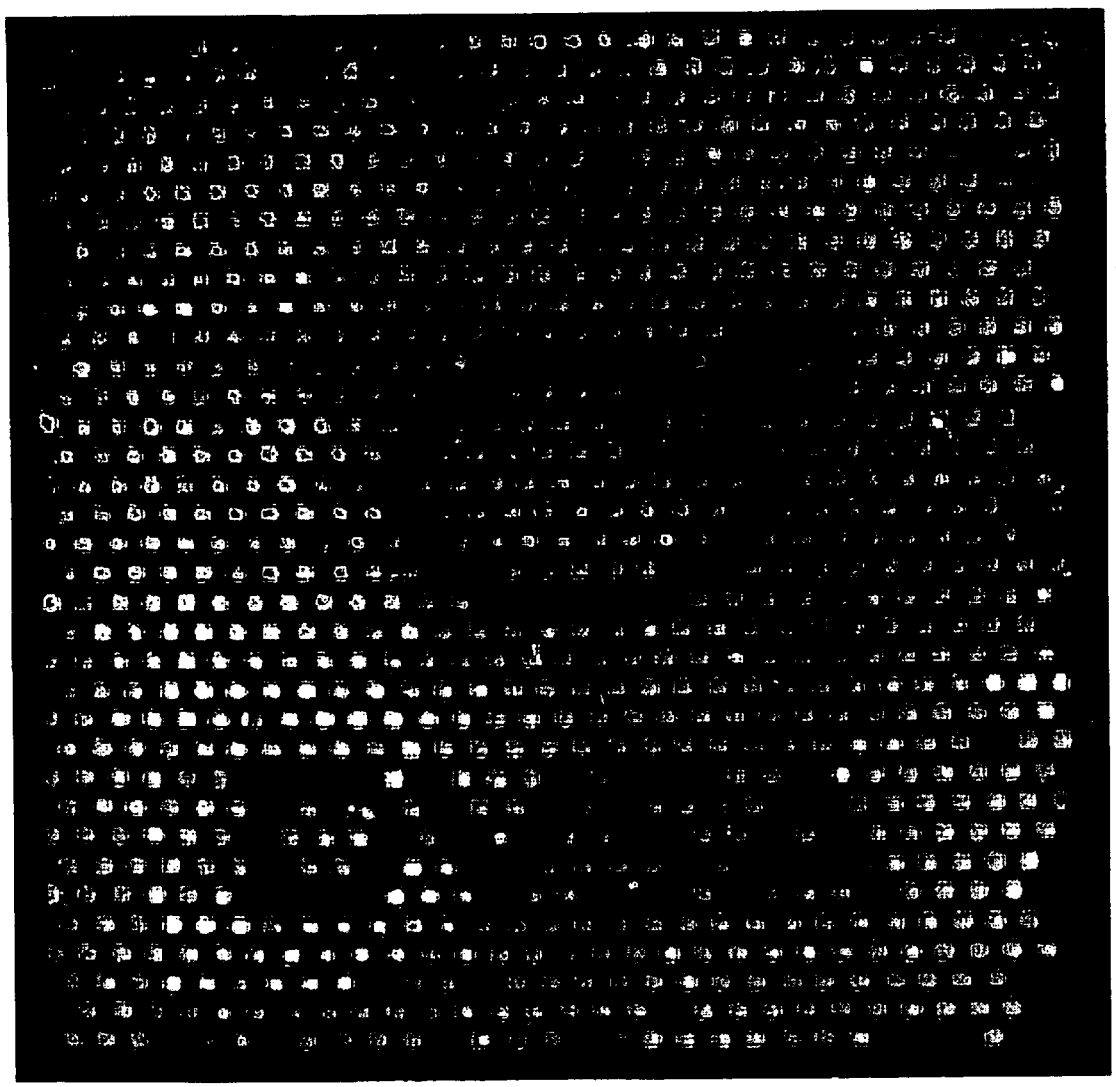
FIG. 6 shows a depiction of the degree of fidelity in the recovery technique that can be achieved by the methods of the invention.

In another embodiment, the sample is aspirated by use of a vacuum. In this embodiment, the needle contacts the capillary opening and the sample is "vacuumed" or aspirated from the capillary tube onto or into a collection device. The collection device may be a microfuge tube or a filter located proximal to the opening of the needle, as depicted in FIGS. 5A–C. FIG. 5D shows further processing of a sample collected onto a filter following aspiration of the sample from the capillary. The sample (e.g., cells, proteins, or nucleic acids) present on the filter can be delivered into a collection device (e.g., a microfuge tube, capillary tube, microtiter plate, cell culture plate, and the like) by forcing media, air or other fluid through the filter in the reverse direction. FIG. 6 shows the fidelity by which the methods of the invention are capable of extracting sample(s) from the capillary array.

Accordingly, the capillaries, capillary array and systems of the invention are particularly well suited for screening libraries for activity. The screening for activity may be effected on individual expression clones or may be initially effected on a mixture of expression clones to ascertain whether or not the mixture has one or more specified activities. If the mixture has a specified activity, then the individual clones may be rescreened for such activity or for a more specific activity after collection from the capillary array.

The library may, for example, be screened for a specified enzyme activity. For example, the enzyme activity screened for may be one or more of the six IUB classes; oxidoreductases, transferases, hydrolases, lyases, isomerases and ligases. The recombinant enzymes which are determined to be positive for one or more of the IUB classes may then be rescreened for a more specific enzyme activity.

Alternatively, the library may be screened for a more specialized enzyme activity. For example, instead of generically screening for hydrolase activity, the library may be screened for a more specialized activity, i.e. the type of bond on which the hydrolase acts. Thus, for example, the library may be screened to ascertain those hydrolases which act on one or more specified chemical functionalities, such as: (a) amide (peptide bonds), i.e. proteases; (b) ester bonds, i.e. esterases and lipases; (c) acetals, i.e., glycosidases etc.

As described with respect to one of the above aspects, the invention provides a process for activity screening of clones containing selected DNA derived from a microorganism which method comprises:

screening a library for specified enzyme activity, said library including a plurality of clones, said clones having been prepared by recovering genomic DNA from a mixed population of organisms, and transforming a host with the selected DNA to produce clones which are screened for the specified enzyme activity.

In another embodiment, an enrichment step may be used before activity based screening. The enrichment step can be, for example, a biopanning method. A procedure of "biopanning" is described and exemplified in U.S. Ser. No. 08/692, 002, filed Aug. 2, 1996.

In another embodiment, the polynucleotides are contained in clones, the clones having been prepared from nucleic acid sequences of a mixed population of organisms, wherein the nucleic acid sequences are used to prepare a DNA library of the mixed population of organisms. The DNA library is screened for a sequence of interest by transfecting a host cell containing the library with at least one labeled nucleic acid sequence which is all or a portion of a DNA sequence encoding a bioactivity having a desirable activity and separating the library clones containing the desirable sequence by fluorescent based analysis.

The present invention offers the ability to screen for many types of bioactivities. For instance, the ability to select and combine desired components from a library of polyketides and postpolyketide biosynthesis genes for generation of novel polyketides for study is appealing. The method(s) of the present invention make it possible to and facilitate the cloning of novel polyketide synthases, and other relevant pathways or genes encoding commercially relevant secondary metabolites, since one can generate gene banks with clones containing large inserts (especially when using vectors which can accept large inserts, such as the f-factor based vectors), which facilitates cloning of gene clusters.

The biopanning approach described above can be used to create libraries enriched with clones carrying sequences homologous to a given probe sequence. Using this approach libraries containing clones with inserts of up to 40 kbp can be enriched approximately 1,000 fold after each round of panning. This enables one to reduce the number of clones to be screened after 1 round of biopanning enrichment. This approach can be applied to create libraries enriched for clones carrying sequence of interest related to a bioactivity of interest for example polyketide sequences.

Hybridization screening using high density filters or biopanning has proven an efficient approach to detect homologues of pathways containing conserved genes. To discover novel bioactive molecules that may have no known counterparts, however, other approaches are necessary. Another approach of the present invention is to screen in *E. coli* for the expression of small molecule ring structures or "backbones". Because the genes encoding these polycyclic structures can often be expressed in *E. coli* the small molecule backbone can be manufactured albeit in an inactive form. Bioactivity is conferred upon transferring the molecule or pathway to an appropriate host that expresses the requisite glycosylation and methylation genes that can modify or "decorate" the structure to its active form. Thus, inactive ring compounds, recombinantly expressed in *E. coli* are detected to identify clones which are then shuttled to a metabolically rich host, such as *Streptomyces*, for subsequent production of the bioactive molecule. The use of high throughput robotic systems allows the screening of hundreds of thousands of clones in multiplexed arrays in microtiter dishes.

One approach to detect and enrich for clones carrying these structures is to use the capillary screening method of the invention or a FACS screening, a procedure described and exemplified in U.S. Ser. No. 08/876,276, filed Jun. 16, 1997. Polycyclic ring compounds typically have characteristic fluorescent spectra when excited by ultraviolet light. Thus clones expressing these structures can be distinguished from background using a sufficiently sensitive detection method. For example, as described above, capillary array systems can be used to screen for fluorescent or optically detectable signals. In addition, high throughput FACS screening can be utilized in combination with the capillary system of the invention either before or after FACS screening to screen for small molecule backbones in *E. coli* libraries. Commercially available FACS machines are capable of screening up to 100,000 clones per second for UV active molecules. These clones can be sorted for further FACS screening or the resident plasmids can be extracted and shuttled to *Streptomyces* for activity screening.

In an alternate screening approach, after shuttling to a *Streptomyces* host, organic extracts from candidate clones can be tested for bioactivity by susceptibility screening against test organisms such as *Staphylococcus aureus, E. coli*, or *Saccharomyces cervisiae*.

An alternative to the above-mentioned screening methods provided by the present invention is an approach termed "mixed extract" screening. The "mixed extract" screening approach takes advantage of the fact that the accessory genes needed to confer activity upon the polycyclic backbones are expressed in metabolically rich hosts, such as *Streptomyces*, and that the enzymes can be extracted and combined with the backbones extracted from *E. coli* clones to produce the bioactive compound in vitro. Enzyme extract preparations from metabolically rich hosts, such as *Streptomyces* strains, at various growth stages are combined with pools of organic extracts from *E. coli* libraries and then evaluated for bioactivity.

Another approach to detect activity in the *E. coli* clones is to screen for genes that can convert bioactive compounds to different forms. For example, a recombinant enzyme was recently discovered that can convert the low value daunomycin to the higher value doxorubicin. Similar enzyme pathways are being sought to convert penicillins to cephalosporins.

Screening may be carried out to detect a specified enzyme activity by procedures known in the art. For example, enzyme activity may be screened for one or more of the six IUB classes; oxidoreductases, transferases, hydrolases, lyases, isomerases and ligases. The recombinant enzymes which are determined to be positive for one or more of the IUB classes may then be rescreened for a more specific enzyme activity. Alternatively, the library may be screened for a more specialized enzyme activity. For example, instead of generically screening for hydrolase activity, the library may be screened for a more specialized activity, i.e. the type of bond on which the hydrolase acts. Thus, for example, the library may be screened to ascertain those hydrolases which act on one or more specified chemical functionalities, such as: (a) amide (peptide bonds), i.e. proteases; (b) ester bonds, i.e. esterases and lipases; (c) acetals, i.e., glycosidases.

The capillary screening method of the invention can also be used to detect expression of UV fluorescent molecules in metabolically rich hosts, such as *Streptomyces*. Recombinant oxytetracylin retains its diagnostic red fluorescence when produced heterologously in *S. lividans* TK24. Pathway clones, which can be identified by the methods and systems of the invention, can thus be screened for polycyclic molecules in a high throughput fashion.

Recombinant bioactive compounds can also be screened in vivo using "two-hybrid" systems, which can detect enhancers and inhibitors of protein-protein or other interactions such as those between transcription factors and their activators, or receptors and their cognate targets. In this embodiment, both a small molecule pathway and a GFP reporter construct are co-expressed. Clones altered in GFP expression can then be identified by the capillary array techniques described herein and the pathway clone isolated for characterization.

As indicated, common approaches to drug discovery involve screening assays in which disease targets (macromolecules implicated in causing a disease) are exposed to potential drug candidates which are tested for therapeutic activity. In other approaches, whole cells or organisms that are representative of the causative agent of the disease, such as bacteria or tumor cell lines, are exposed to the potential candidates for screening purposes. Any of these approaches can be employed with the present invention.

The present invention also allows for the transfer of cloned pathways derived from uncultivated samples into metabolically rich hosts for heterologous expression and downstream screening for bioactive compounds of interest using a variety of screening approaches briefly described above.

After viable or non-viable cells, are screened and positive clones are recovered, DNA can be isolated from positive clones utilizing techniques well known in the art. The DNA can then be amplified either in vivo or in vitro by utilizing any of the various amplification techniques known in the art. In vivo amplification would include transformation of the clone(s) or subclone(s) into a viable host, followed by growth of the host. In vitro amplification can be performed using techniques such as the polymerase chain reaction. Once amplified the identified sequences can be "evolved" or sequenced.

One advantage afforded by present invention is the ability to manipulate the identified polynucleotides to generate and select for encoded variants with altered activity or specificity.

Clones found to have the bioactivity for which the screen was performed can be subjected to directed mutagenesis to develop new bioactivities with desired properties or to develop modified bioactivities with particularly desired properties that are absent or less pronounced in the wild-type activity, such as stability to heat or organic solvents. Any of the known techniques for directed mutagenesis are applicable to the invention. For example, particularly preferred mutagenesis techniques for use in accordance with the invention include those described below.

Alternatively, it may be desirable to variegate a polynucleotide sequence obtained, identified or cloned as described herein. Such variegation can modify the polynucleotide sequence in order to modify (e.g., increase or decrease) the encoded polypeptide's activity, specificity, affinity, function, etc. DNA shuffling can be used to increase variation in a particular sample. DNA shuffling is meant to indicate recombination between substantially homologous but non-identical sequences, in some embodiments DNA shuffling may involve crossover via non-homologous recombination, such as via cer/lox and/or flp/frt systems and the like (see, for example, U.S. Pat. No. 5,939,250, issued to Dr. Jay Short on Aug. 17, 1999, and assigned to Diversa Corporation, the disclosure of which is incorporated herein by reference). Various methods for shuffling, mutating or variegating polynucleotide sequences are discussed below.

Nucleic acid shuffling is a method for in vitro or invivo homologous recombination of pools of shorter or smaller polynucleotides to produce a polynucleotide or polynucleotides. Mixtures of related nucleic acid sequences or polynucleotides are subjected to sexual PCR to provide random polynucleotides, and reassembled to yield a library or mixed population of recombinant hybrid nucleic acid molecules or polynucleotides.

In contrast to cassette mutagenesis, only shuffling and error-prone PCR allow one to mutate a pool of sequences blindly (without sequence information other than primers).

The advantage of the mutagenic shuffling of the invention over error-prone PCR alone for repeated selection can best be explained as follows. Consider DNA shuffling as compared with error-prone PCR (not sexual PCR). The initial library of selected pooled sequences can consist of related sequences of diverse origin or can be derived by any type of mutagenesis (including shuffling) of a single gene. A collection of selected sequences is obtained after the first round of activity selection. Shuffling allows the free combinatorial association of all of the related sequences, for example.

This method differs from error-prone PCR, in that it is an inverse chain reaction. In error-prone PCR, the number of polymerase start sites and the number of molecules grows exponentially. However, the sequence of the polymerase start sites and the sequence of the molecules remains essentially the same. In contrast, in nucleic acid reassembly or shuffling of random polynucleotides the number of start sites and the number (but not size) of the random polynucleotides decreases over time. For polynucleotides derived from whole plasmids the theoretical endpoint is a single, large concatemeric molecule.

Since cross-overs occur at regions of homology, recombination will primarily occur between members of the same sequence family. This discourages combinations of sequences that are grossly incompatible (e.g., having different activities or specificities). It is contemplated that multiple families of sequences can be shuffled in the same reaction. Further, shuffling generally conserves the relative order.

Rare shufflants will contain a large number of the best molecules (e.g., highest activity or specificity) and these rare shufflants may be selected based on their superior activity or specificity.

A pool of 100 different polypeptide sequences can be permutated in up to $10^3$ different ways. This large number of permutations cannot be represented in a single library of DNA sequences. Accordingly, it is contemplated that multiple cycles of DNA shuffling and selection may be required depending on the length of the sequence and the sequence diversity desired.

Error-prone PCR, in contrast, keeps all the selected sequences in the same relative orientation, generating a much smaller mutant cloud.

The template polynucleotide which may be used in the methods of the invention may be DNA or RNA. It may be of various lengths depending on the size of the gene or shorter or smaller polynucleotide to be recombined or reassembled. Preferably, the template polynucleotide is from 50 bp to 50 kb. It is contemplated that entire vectors containing the nucleic acid encoding the protein of interest can be used in the methods of the invention, and in fact have been successfully used.

The template polynucleotide may be obtained by amplification using the PCR reaction (U.S. Pat. No. 4,683,202 and U.S. Pat. No. 4,683,195) or other amplification or cloning methods. However, the removal of free primers from the PCR products before subjecting them to pooling of the PCR products and sexual PCR may provide more efficient results. Failure to adequately remove the primers from the original pool before sexual PCR can lead to a low frequency of crossover clones.

The template polynucleotide often is double-stranded. A double-stranded nucleic acid molecule is recommended to ensure that regions of the resulting single-stranded polynucleotides are complementary to each other and thus can hybridize to form a double-stranded molecule.

It is contemplated that single-stranded or double-stranded nucleic acid polynucleotides having regions of identity to the template polynucleotide and regions of heterology to the template polynucleotide may be added to the template polynucleotide, at this step. It is also contemplated that two different but related polynucleotide templates can be mixed at this step.

The double-stranded polynucleotide template and any added double-or single-stranded polynucleotides are subjected to sexual PCR which includes slowing or halting to provide a mixture of from about 5 bp to 5 kb or more. Preferably the size of the random polynucleotides is from about 10 bp to 1000 bp, more preferably the size of the polynucleotides is from about 20 bp to 500 bp.

Alternatively, it is also contemplated that double-stranded nucleic acid having multiple nicks may be used in the methods of the invention. A nick is a break in one strand of the double-stranded nucleic acid. The distance between such nicks is preferably 5 bp to 5 kb, more preferably between 10 bp to 1000 bp. This can provide areas of self-priming to produce shorter or smaller polynucleotides to be included with the polynucleotides resulting from random primers, for example.

The concentration of any one specific polynucleotide will not be greater than 1% by weight of the total polynucleotides, more preferably the concentration of any one specific nucleic acid sequence will not be greater than 0.1% by weight of the total nucleic acid.

The number of different specific polynucleotides in the mixture will be at least about 100, preferably at least about 500, and more preferably at least about 1000.

At this step single-stranded or double-stranded polynucleotides, either synthetic or natural, may be added to the random double-stranded shorter or smaller polynucleotides in order to increase the heterogeneity of the mixture of polynucleotides.

It is also contemplated that populations of double-stranded randomly broken polynucleotides may be mixed or combined at this step with the polynucleotides from the sexual PCR process and optionally subjected to one or more additional sexual PCR cycles.

Where insertion of mutations into the template polynucleotide is desired, single-stranded or double-stranded polynucleotides having a region of identity to the template polynucleotide and a region of heterology to the template polynucleotide may be added in a 20 fold excess by weight as compared to the total nucleic acid, more preferably the single-stranded polynucleotides may be added in a 10 fold excess by weight as compared to the total nucleic acid.

Where a mixture of different but related template polynucleotides is desired, populations of polynucleotides from each of the templates may be combined at a ratio of less than about 1:100, more preferably the ratio is less than about 1:40. For example, a backcross of the wild-type polynucleotide with a population of mutated polynucleotide may be desired to eliminate neutral mutations (e.g., mutations yielding an insubstantial alteration in the phenotypic property being selected for). In such an example, the ratio of randomly provided wild-type polynucleotides which may be added to the randomly provided sexual PCR cycle hybrid polynucleotides is approximately 1:1 to about 100:1, and more preferably from 1:1 to 40:1.

The mixed population of random polynucleotides are denatured to form single-stranded polynucleotides and then re-annealed. Only those single-stranded polynucleotides having regions of homology with other single-stranded polynucleotides will re-anneal.

The random polynucleotides may be denatured by heating. One skilled in the art could determine the conditions necessary to completely denature the double-stranded nucleic acid. Preferably the temperature is from 80° C. to 100° C., more preferably the temperature is from 90° C. to 96° C. other methods which may be used to denature the polynucleotides include pressure and pH.

The polynucleotides may be re-annealed by cooling. Preferably the temperature is from 20° C. to 75° C., more preferably the temperature is from 40° C. to 65° C. If a high frequency of crossovers is needed based on an average of only 4 consecutive bases of homology, recombination can be forced by using a low annealing temperature, although the process becomes more difficult. The degree of renaturation which occurs will depend on the degree of homology between the population of single-stranded polynucleotides.

Renaturation can be accelerated by the addition of polyethylene glycol ("PEG") or salt. The salt concentration is preferably from 0 mM to 200 mM, more preferably the salt concentration is from 10 mM to 100 mm. The salt may be KCl or NaCl. The concentration of PEG is preferably from 0% to 20%, more preferably from 5% to 10%.

The annealed polynucleotides are next incubated in the presence of a nucleic acid polymerase and dNTP's (i.e. dATP, dCTP, DGTP and dTTP). The nucleic acid polymerase may be the Klenow fragment, the Taq polymerase or any other DNA polymerase known in the art.

The approach to be used for the assembly depends on the minimum degree of homology that should still yield crossovers. If the areas of identity are large, Taq polymerase can be used with an annealing temperature of between 45–65° C. If the areas of identity are small, Klenow polymerase can be used with an annealing temperature of between 20–30° C. One skilled in the art could vary the temperature of annealing to increase the number of cross-overs achieved.

The polymerase may be added to the random polynucleotides prior to annealing, simultaneously with annealing or after annealing.

The cycle of denaturation, renaturation and incubation in the presence of polymerase is referred to herein as shuffling or reassembly of the nucleic acid. This cycle is repeated for a desired number of times. Preferably the cycle is repeated from 2 to 50 times, more preferably the sequence is repeated from 10 to 40 times.

The resulting nucleic acid is a larger double-stranded polynucleotide of from about 50 bp to about 100 kb, preferably the larger polynucleotide is from 500 bp to 50 kb.

This larger polynucleotides may contain a number of copies of a polynucleotide having the same size as the template polynucleotide in tandem. This concatemeric polynucleotide is then denatured into single copies of the template polynucleotide. The result will be a population of polynucleotides of approximately the same size as the template polynucleotide. The population will be a mixed population where single or double-stranded polynucleotides having an area of identity and an area of heterology have been added to the template polynucleotide prior to shuffling. These polynucleotides are then cloned into the appropriate vector and the ligation mixture used to transform bacteria.

It is contemplated that the single polynucleotides may be obtained from the larger concatemeric polynucleotide by amplification of the single polynucleotide prior to cloning by a variety of methods including PCR (U.S. Pat. No. 4,683,195 and U.S. Pat. No. 4,683,202), rather than by digestion of the concatemer.

The vector used for cloning is not critical provided that it will accept a polynucleotide of the desired size. If expression of the particular polynucleotide is desired, the cloning vehicle should further comprise transcription and translation signals next to the site of insertion of the polynucleotide to allow expression of the polynucleotide in the host cell.

The resulting bacterial population will include a number of recombinant polynucleotides having random mutations. This mixed population may be tested to identify the desired recombinant polynucleotides. The method of selection will depend on the polynucleotide desired.

For example, if a polynucleotide, identified by the methods of described herein, encodes a protein with a first binding affinity, subsequent mutated (e.g., shuffled) sequences having an increased binding efficiency to a ligand may be desired. In such a case the proteins expressed by each of the portions of the polynucleotides in the population or library may be tested for their ability to bind to the ligand by methods known in the art (i.e. panning, affinity chromatography). If a polynucleotide which encodes for a protein with increased drug resistance is desired, the proteins expressed by each of the polynucleotides in the population or library may be tested for their ability to confer drug resistance to the host organism. One skilled in the art, given knowledge of the desired protein, could readily test the population to identify polynucleotides which confer the desired properties onto the protein.

It is contemplated that one skilled in the art could use a phage display system in which fragments of the protein are expressed as fusion proteins on the phage surface (Pharmacia, Milwaukee Wis.). The recombinant DNA molecules are cloned into the phage DNA at a site which results in the transcription of a fusion protein a portion of which is encoded by the recombinant DNA molecule. The phage containing the recombinant nucleic acid molecule undergoes replication and transcription in the cell. The leader sequence of the fusion protein directs the transport of the fusion protein to the tip of the phage particle. Thus, the fusion protein which is partially encoded by the recombinant DNA molecule is displayed on the phage particle for detection and selection by the methods described above.

It is further contemplated that a number of cycles of nucleic acid shuffling may be conducted with polynucleotides from a sub-population of the first population, which sub-population contains DNA encoding the desired recombinant protein. In this manner, proteins with even higher binding affinities or enzymatic activity could be achieved.

It is also contemplated that a number of cycles of nucleic acid shuffling may be conducted with a mixture of wild-type polynucleotides and a sub-population of nucleic acid from the first or subsequent rounds of nucleic acid shuffling in order to remove any silent mutations from the sub-population.

Any source of nucleic acid, in a purified form can be utilized as the starting nucleic acid. Thus the process may employ DNA or RNA including messenger RNA, which DNA or RNA may be single or double stranded. In addition, a DNA-RNA hybrid which contains one strand of each may be utilized. The nucleic acid sequence may be of various lengths depending on the size of the nucleic acid sequence to be mutated. Preferably the specific nucleic acid sequence is from 50 to 50,000 base pairs. It is contemplated that entire vectors containing the nucleic acid encoding the protein of interest may be used in the methods of the invention.

Any specific nucleic acid sequence can be used to produce the population of hybrids by the present process. It is only necessary that a small population of hybrid sequences of the specific nucleic acid sequence exist or be available for the present process.

A population of specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into *E. coli* and propagated as a pool or library of hybrid plasmids.

Alternatively, a small mixed population of specific nucleic acids may be found in nature in that they may consist of different alleles of the same gene or the same gene from different related species (i.e., cognate genes). Alternatively, they may be related DNA sequences found within one species, for example, the immunoglobulin genes.

Once a mixed population of specific nucleic acid sequences is generated, the polynucleotides can be used directly or inserted into an appropriate cloning vector, using techniques well-known in the art.

The choice of vector depends on the size of the polynucleotide sequence and the host cell to be employed in the methods of the invention. The templates of the invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are preferred where the specific nucleic acid sequence to be mutated is larger because these vectors are able to stably propagate large polynucleotides.

If a mixed population of the specific nucleic acid sequence is cloned into a vector it can be clonally amplified. Utility can be readily determined by screening expressed polypeptides.

The DNA shuffling method of the invention can be performed blindly on a pool of unknown sequences. By adding to the reassembly mixture oligonucleotides (with ends that are homologous to the sequences being reassembled) any sequence mixture can be incorporated at any specific position into another sequence mixture. Thus, it is contemplated that mixtures of synthetic oligonucleotides, PCR polynucleotides or even whole genes can be mixed into another sequence library at defined positions. The insertion of one sequence (mixture) is independent from the insertion of a sequence in another part of the template. Thus, the degree of recombination, the homology required, and the diversity of the library can be independently and simultaneously varied along the length of the reassembled DNA.

Shuffling requires the presence of homologous regions separating regions of diversity. Scaffold-like protein structures may be particularly suitable for shuffling. The conserved scaffold determines the overall folding by self-association, while displaying relatively unrestricted loops that mediate the specific binding. Examples of such scaffolds are the immunoglobulin beta-barrel, and the four-helix bundle which are well-known in the art. This shuffling can be used to create scaffold-like proteins with various combinations of mutated sequences for binding.

In Vitro Shuffling

The equivalents of some standard genetic matings may also be performed by shuffling in vitro. For example, a "molecular backcross" can be performed by repeatedly mixing the hybrid's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (e.g., immunogenicity). Thus it can be useful to determine which mutations in a protein are involved in the enhanced biological activity and which are not, an advantage which cannot be achieved by error-prone mutagenesis or cassette mutagenesis methods.

Large, functional genes can be assembled correctly from a mixture of small random polynucleotides. This reaction may be of use for the reassembly of genes from the highly fragmented DNA of fossils. In addition random nucleic acid fragments from fossils may be combined with polynucleotides from similar genes from related species.

It is also contemplated that the method of the invention can be used for the in vitro amplification of a whole genome from a single cell as is needed for a variety of research and diagnostic applications. DNA amplification by PCR typically includes sequences of about 40 kb. Amplification of a whole genome such as that of *E. coli* (5,000 kb) by PCR would require about 250 primers yielding 125 forty kb polynucleotides. On the other hand, random production of polynucleotides of the genome with sexual PCR cycles, followed by gel purification of small polynucleotides will provide a multitude of possible primers. Use of this mix of random small polynucleotides as primers in a PCR reaction alone or with the whole genome as the template should result in an inverse chain reaction with the theoretical endpoint of a single concatamer containing many copies of the genome.

A 100 fold amplification in the copy number and an average polynucleotide size of greater than 50 kb may be obtained when only random polynucleotides are used. It is thought that the larger concatamer is generated by overlap of many smaller polynucleotides. The quality of specific PCR products obtained using synthetic primers will be indistinguishable from the product obtained from unamplified DNA. It is expected that this approach will be useful for the mapping of genomes.

The polynucleotide to be shuffled can be produced as random or non-random polynucleotides, at the discretion of the practitioner. Moreover, the invention provides a method of shuffling that is applicable to a wide range of polynucleotide sizes and types, including the step of generating polynucleotide monomers to be used as building blocks in the reassembly of a larger polynucleotide. For example, the building blocks can be fragments of genes or they can be comprised of entire genes or gene pathways, or any combination thereof.

In Vivo Shuffling

In an embodiment of in vivo shuffling, a mixed population of a specific nucleic acid sequence is introduced into bacterial or eukaryotic cells under conditions such that at least two different nucleic acid sequences are present in each host cell. The polynucleotides can be introduced into the host cells by a variety of different methods. The host cells can be transformed with the smaller polynucleotides using methods known in the art, for example treatment with calcium chloride. If the polynucleotides are inserted into a phage genome, the host cell can be transfected with the recombinant phage genome having the specific nucleic acid sequences. Alternatively, the nucleic acid sequences can be introduced into the host cell using electroporation, transfection, lipofection, biolistics, conjugation, and the like.

In general, in this embodiment, specific nucleic acid sequences will be present in vectors which are capable of stably replicating the sequence in the host cell. In addition, it is contemplated that the vectors will encode a marker gene such that host cells having the vector can be selected. This ensures that the mutated specific nucleic acid sequence can be recovered after introduction into the host cell. However, it is contemplated that the entire mixed population of the specific nucleic acid sequences need not be present on a vector sequence. Rather only a sufficient number of sequences need be cloned into vectors to ensure that after introduction of the polynucleotides into the host cells each host cell contains one vector having at least one specific nucleic acid sequence present therein. It is also contemplated that rather than having a subset of the population of the specific nucleic acids sequences cloned into vectors, this subset may be already stably integrated into the host cell.

It has been found that when two polynucleotides which have regions of identity are inserted into the host cells homologous recombination occurs between the two polynucleotides. Such recombination between the two mutated specific nucleic acid sequences will result in the production of double or triple hybrids in some situations.

It has also been found that the frequency of recombination is increased if some of the mutated specific nucleic acid sequences are present on linear nucleic acid molecules. Therefore, in a one embodiment, some of the specific nucleic acid sequences are present on linear polynucleotides.

After transformation, the host cell transformants are placed under selection to identify those host cell transformants which contain mutated specific nucleic acid sequences having the qualities desired. For example, if increased resistance to a particular drug is desired then the transformed host cells may be subjected to increased concentrations of the particular drug and those transformants producing mutated proteins able to confer increased drug resistance will be selected. If the enhanced ability of a particular protein to bind to a receptor is desired, then expression of the protein can be induced from the transformants and the resulting protein assayed in a ligand binding assay by methods known in the art to identify that subset of the mutated population which shows enhanced binding to the ligand. Alternatively, the protein can be expressed in another system to ensure proper processing.

Once a subset of the first recombined specific nucleic acid sequences (daughter sequences) having the desired characteristics are identified, they are then subject to a second round of recombination. In the second cycle of recombination, the recombined specific nucleic acid sequences may be mixed with the original mutated specific nucleic acid sequences (parent sequences) and the cycle repeated as described above. In this way a set of second recombined specific nucleic acids sequences can be identified which have enhanced characteristics or encode for proteins having enhanced properties. This cycle can be repeated a number of times as desired.

It is also contemplated that in the second or subsequent recombination cycle, a backcross can be performed. A molecular backcross can be performed by mixing the desired specific nucleic acid sequences with a large number of the wild-type sequence, such that at least one wild-type nucleic acid sequence and a mutated nucleic acid sequence are present in the same host cell after transformation. Recombination with the wild-type specific nucleic acid sequence will eliminate those neutral mutations that may affect unselected characteristics such as immunogenicity but not the selected characteristics.

In another embodiment of the invention, it is contemplated that during the first round a subset of specific nucleic acid sequences can be generated as smaller polynucleotides by slowing or halting their PCR amplification prior to introduction into the host cell. The size of the polynucleotides must be large enough to contain some regions of identity with the other sequences so as to homologously recombine with the other sequences. The size of the polynucleotides will range from 0.03 kb to 100 kb more preferably from 0.2 kb to 10 kb. It is also contemplated that in subsequent rounds, all of the specific nucleic acid sequences other than the sequences selected from the previous round may be utilized to generate PCR polynucleotides prior to introduction into the host cells.

The shorter polynucleotide sequences can be single-stranded or double-stranded. The reaction conditions suitable for separating the strands of nucleic acid are well known in the art.

The steps of this process can be repeated indefinitely, being limited only by the number of possible hybrids which can be achieved.

Therefore, the initial pool or population of mutated template nucleic acid is cloned into a vector capable of replicating in a bacteria such as *E. coli*. The particular vector is not essential, so long as it is capable of autonomous replication in *E. coli*. In a one embodiment, the vector is designed to allow the expression and production of any protein encoded by the mutated specific nucleic acid linked to the vector. It is also preferred that the vector contain a gene encoding for a selectable marker.

The population of vectors containing the pool of mutated nucleic acid sequences is introduced into the *E. coli* host cells. The vector nucleic acid sequences may be introduced by transformation, transfection or infection in the case of phage. The concentration of vectors used to transform the bacteria is such that a number of vectors is introduced into each cell. Once present in the cell, the efficiency of homologous recombination is such that homologous recombination occurs between the various vectors. This results in the generation of hybrids (daughters) having a combination of mutations which differ from the original parent mutated sequences. The host cells are then clonally replicated and selected for the marker gene present on the vector. Only those cells having a plasmid will grow under the selection. The host cells which contain a vector are then tested for the presence of favorable mutations.

Once a particular daughter mutated nucleic acid sequence has been identified which confers the desired characteristics, the nucleic acid is isolated either already linked to the vector or separated from the vector. This nucleic acid is then mixed with the first or parent population of nucleic acids and the cycle is repeated.

The parent mutated specific nucleic acid population, either as polynucleotides or cloned into the same vector is introduced into the host cells already containing the daughter nucleic acids. Recombination is allowed to occur in the cells and the next generation of recombinants, or granddaughters are selected by the methods described above. This cycle can be repeated a number of times until the nucleic acid or peptide having the desired characteristics is obtained. It is contemplated that in subsequent cycles, the population of mutated sequences which are added to the hybrids may come from the parental hybrids or any subsequent generation.

In an alternative embodiment, the invention provides a method of conducting a "molecular" backcross of the obtained recombinant specific nucleic acid in order to eliminate any neutral mutations. Neutral mutations are those mutations which do not confer onto the nucleic acid or peptide the desired properties. Such mutations may however confer on the nucleic acid or peptide undesirable characteristics. Accordingly, it is desirable to eliminate such neutral mutations. The method of the invention provide a means of doing so.

In this embodiment, after the hybrid nucleic acid, having the desired characteristics, is obtained by the methods of the embodiments, the nucleic acid, the vector having the nucleic acid or the host cell containing the vector and nucleic acid is isolated.

The nucleic acid or vector is then introduced into the host cell with a large excess of the wild-type nucleic acid. The nucleic acid of the hybrid and the nucleic acid of the wild-type sequence are allowed to recombine. The resulting recombinants are placed under the same selection as the hybrid nucleic acid. Only those recombinants which retained the desired characteristics will be selected. Any silent mutations which do not provide the desired characteristics will be lost through recombination with the wild-type DNA. This cycle can be repeated a number of times until all of the silent mutations are eliminated.

Exonuclease-Mediated Reassembly

In a another embodiment, the invention provides for a method for shuffling, assembling, reassembling, recombining, and/or concatenating at least two polynucleotides to form a progeny polynucleotide (e.g., a chimeric progeny polynucleotide that can be expressed to produce a polypeptide or a gene pathway). In a particular embodiment, a double stranded polynucleotide (e.g., two single stranded sequences hybridized to each other as hybridization partners) is treated with an exonuclease to liberate nucleotides from one of the two strands, leaving the remaining strand free of its original partner so that, if desired, the remaining strand may be used to achieve hybridization to another partner.

In a particular aspect, a double stranded polynucleotide end (that may be part of—or connected to—a polynucleotide or a nonpolynucleotide sequence) is subjected to a source of exonuclease activity. Serviceable sources of exonuclease activity may be an enzyme with 3' exonuclease activity, an enzyme with 5' exonuclease activity, an enzyme with both 3' exonuclease activity and 5' exonuclease activity, and any combination thereof. An exonuclease can be used to liberate nucleotides from one or both ends of a linear double stranded polynucleotide, and from one to all ends of a branched polynucleotide having more than two ends.

By contrast, a non-enzymatic step may be used to shuffle, assemble, reassemble, recombine, and/or concatenate polynucleotide building blocks that is comprised of subjecting a working sample to denaturing (or "melting") conditions (for example, by changing temperature, pH, and/or salinity conditions) so as to melt a working set of double stranded polynucleotides into single polynucleotide strands. For shuffling, it is desirable that the single polynucleotide strands participate to some extent in annealment with different hybridization partners (i.e. and not merely revert to exclusive reannealment between what were former partners before the denaturation step). The presence of the former hybridization partners in the reaction vessel, however, does not preclude, and may sometimes even favor, reannealment of a single stranded polynucleotide with its former partner, to recreate an original double stranded polynucleotide.

In contrast to this non-enzymatic shuffling step comprised of subjecting double stranded polynucleotide building blocks to denaturation, followed by annealment, the invention further provides an exonuclease-based approach requiring no denaturation—rather, the avoidance of denaturing conditions and the maintenance of double stranded polynucleotide substrates in annealed (i.e. non-denatured) state are necessary conditions for the action of exonucleases (e.g., exonuclease III and red alpha gene product). Additionally, in contrast, the generation of single stranded polynucleotide sequences capable of hybridizing to other single stranded polynucleotide sequences is the result of covalent cleavage—and hence sequence destruction—in one of the hybridization partners. For example, an exonuclease III enzyme may be used to enzymatically liberate 3' terminal nucleotides in one hybridization strand (to achieve covalent hydrolysis in that polynucleotide strand); and this favors hybridization of the remaining single strand to a new partner (since its former partner was subjected to covalent cleavage).

It is particularly appreciated that enzymes can be discovered, optimized (e.g., engineered by directed evolution), or both discovered and optimized specifically for the instantly disclosed approach that have more optimal rates and/or more highly specific activities &/or greater lack of unwanted activities. In fact it is expected that the invention may encourage the discovery and/or development of such designer enzymes.

Furthermore, it is appreciated that one can protect the end of a double stranded polynucleotide or render it susceptible to a desired enzymatic action of a serviceable exonuclease as necessary. For example, a double stranded polynucleotide end having a 3' overhang is not susceptible to the exonuclease action of exonuclease III. However, it may be rendered susceptible to the exonuclease action of exonuclease III by a variety of means; for example, it may be blunted by treatment with a polymerase, cleaved to provide a blunt end or a 5' overhang, joined (ligated or hybridized) to another double stranded polynucleotide to provide a blunt end or a 5' overhang, hybridized to a single stranded polynucleotide to provide a blunt end or a 5' overhang, or modified by any of a variety of means).

According to one aspect, an exonuclease may be allowed to act on one or on both ends of a linear double stranded polynucleotide and proceed to completion, to near completion, or to partial completion. When the exonuclease action is allowed to go to completion, the result will be that the length of each 5' overhang will be extend far towards the middle region of the polynucleotide in the direction of what might be considered a "rendezvous point" (which may be somewhere near the polynucleotide midpoint). Ultimately, this results in the production of single stranded polynucleotides (that can become dissociated) that are each about half the length of the original double stranded polynucleotide.

Thus this exonuclease-mediated approach is serviceable for shuffling, assembling and/or reassembling, recombining, and concatenating polynucleotide building blocks, which polynucleotide building blocks can be up to ten bases long or tens of bases long or hundreds of bases long or thousands of bases long or tens of thousands of bases long or hundreds of thousands of bases long or millions of bases long or even longer.

Substrates for an exonuclease may be generated by subjecting a double stranded polynucleotide to fragmentation. Fragmentation may be achieved by mechanical means (e.g., shearing, sonication, etc.), by enzymatic means (e.g., using restriction enzymes), and by any combination thereof. Fragments of a larger polynucleotide may also be generated by polymerase-mediated synthesis.

Additional examples of enzymes with exonuclease activity include red-alpha and venom phosphodiesterases. Red alpha (redα) gene product (also referred to as lambda exonuclease) is of bacteriophage λ origin. Red alpha gene product acts processively from 5'-phosphorylated termini to liberate mononucleotides from duplex DNA (Takahashi & Kobayashi, 1990). Venom phosphodiesterases (Laskowski, 1980) is capable of rapidly opening supercoiled DNA.

Non-stochastic Ligation Reassembly

In one aspect, the present invention provides a non-stochastic method termed synthetic ligation reassembly (SLR), that is somewhat related to stochastic shuffling, save that the nucleic acid building blocks are not shuffled or concatenated or chimerized randomly, but rather are assembled non-stochastically.

The SLR method does not depend on the presence of a high level of homology between polynucleotides to be shuffled. The invention can be used to non-stochastically generate libraries (or sets) of progeny molecules comprised of over $10^{100}$ different chimeras. Conceivably, SLR can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one embodiment of the invention, the annealed building pieces are treated with an enzyme, such as a ligase (e.g., T4 DNA ligase) to achieve covalent bonding of the building pieces.

In a another embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. As a representative list of families of enzymes which may be mutagenized in accordance with the aspects of the present invention, there may be mentioned, the following enzymes and their functions: Lipase/Esterase, Protease, Glycosidase/Glycosyl, transferase, Phosphatase/Kinase, Mono/Dioxygenase, Haloperoxidase, Lignin, peroxidase/Diarylpropane peroxidase, Epoxide hydrolase, Nitrile hydratase/nitrilase, Transaminase, Amidase/Acylase. These exemplifications, while illustrating certain specific aspects of the invention, do not portray the limitations or circumscribe the scope of the disclosed invention.

Thus according to one aspect of the invention, the sequences of a plurality of progenitor nucleic acid templates identified using the methods of the invention are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, and preferably at almost all of the progenitor templates. Even more preferably still a serviceable demarcation point is an area of homology that is shared by all of the progenitor templates.

In another embodiment, the ligation reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the invention, the possibility of unwanted side products is greatly reduced.

In yet another embodiment, the invention provides that, the ligation reassembly process is performed systematically, for example in order to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. In a particularly embodiment, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one embodiment, this polynucleotide is a gene, which may be a man-made gene. According to another embodiment, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another embodiment, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron (s).

Accordingly, the invention also provides for the generation of a chimeric polynucleotide that is a man-made gene pathway containing one (or more) artificially introduced intron(s). Preferably, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made genes produced using the invention can also serve as a substrate for recombination with another nucleic acid. Likewise, a man-made gene pathway produced using the invention can also serve as a substrate for recombination with another nucleic acid. In a preferred instance, the recombination is facilitated by, or occurs at, areas of homology between the man-made intron-containing gene and a nucleic acid with serves as a recombination partner. In a particularly preferred instance, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic ligation reassembly method of the invention utilizes a plurality of nucleic acid building blocks, each of which preferably has two ligatable ends. The two ligatable ends on each nucleic acid building block may be two blunt ends (i.e. each having an overhang of zero nucleotides), or preferably one blunt end and one overhang, or more preferably still two overhangs.

A serviceable overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

According to one preferred embodiment, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one embodiment, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. Preferably the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 3¹ untranslated regions or 5¹ untranslated regions of genes. Thus this approach may be used to generate genes having increased rates of expression. This approach may also be useful in the study of repetitive DNA sequences. Finally, this approach may be useful to mutate ribozymes or aptamers.

End Selection

The invention provides a method for selecting a subset of polynucleotides from a starting set of polynucleotides, which method is based on the ability to discriminate one or more selectable features (or selection markers) present anywhere in a working polynucleotide, so as to allow one to perform selection for (positive selection) and/or against (negative selection) each selectable polynucleotide. In a one aspect, a method is provided termed end-selection, which method is based on the use of a selection marker located in part or entirely in a terminal region of a selectable polynucleotide, and such a selection marker may be termed an "end-selection marker".

End-selection may be based on detection of naturally occurring sequences or on detection of sequences introduced experimentally (including by any mutagenesis procedure mentioned herein and not mentioned herein) or on both, even within the same polynucleotide. An end-selection marker can be a structural selection marker or a functional selection marker or both a structural and a functional selection marker. An end-selection marker may be comprised of a polynucleotide sequence or of a polypeptide sequence or of any chemical structure or of any biological or biochemical tag, including markers that can be selected using methods based on the detection of radioactivity, of enzymatic activity, of fluorescence, of any optical feature, of a magnetic property (e.g., using magnetic beads), of immunoreactivity, and of hybridization.

End-selection may be applied in combination with any method for performing mutagenesis. Such mutagenesis methods include, but are not limited to, methods described herein (supra and infra). Such methods include, by way of non-limiting exemplification, any method that may be referred herein or by others in the art by any of the following terms: "saturation mutagenesis", "shuffling", "recombination", "re-assembly", "error-prone PCR", "assembly PCR", "sexual PCR", "crossover PCR", "oligonucleotide primer-directed mutagenesis", "recursive (and/or exponential) ensemble mutagenesis (see Arkin and Youvan, 1992)", "cassette mutagenesis", "in vivo mutagenesis", and "in vitro mutagenesis". Moreover, end-selection may be performed on molecules produced by any mutagenesis and/or amplification method (see, e.g., Arnold, 1993; Caldwell and Joyce, 1992; Stemmer, 1994) following which method it is desirable to select for (including to screen for the presence of) desirable progeny molecules.

In addition, end-selection may be applied to a polynucleotide apart from any mutagenesis method. In a one embodiment, end-selection, as provided herein, can be used in order to facilitate a cloning step, such as a step of ligation to another polynucleotide (including ligation to a vector). The invention thus provides for end-selection as a serviceable means to facilitate library construction, selection and/or enrichment for desirable polynucleotides, and cloning in general.

In a another embodiment, end-selection can be based on (positive) selection for a polynucleotide; alternatively end-selection can be based on (negative) selection against a polynucleotide; and alternatively still, end-selection can be based on both (positive) selection for, and on (negative) selection against, a polynucleotide. End-selection, along with other methods of selection and/or screening, can be performed in an iterative fashion, with any combination of like or unlike selection and/or screening methods and serviceable mutagenesis methods, all of which can be performed in an iterative fashion and in any order, combination, and permutation. It is also appreciated that end-selection may also be used to select a polynucleotide in a: circular (e.g., a plasmid or any other circular vector or any other polynucleotide that is partly circular), and/or branched, and/or modified or substituted with any chemical group or moiety.

In one non-limiting aspect, end-selection of a linear polynucleotide is performed using a general approach based on the presence of at least one end-selection marker located at or near a polynucleotide end or terminus (that can be either a 5' end or a 3' end). In one particular non-limiting exemplification, end-selection is based on selection for a specific sequence at or near a terminus such as, but not limited to, a sequence recognized by an enzyme that recognizes a polynucleotide sequence. An enzyme that recognizes and catalyzes a chemical modification of a polynucleotide is referred to herein as a polynucleotide-acting enzyme. In a preferred embodiment, serviceable polynucleotide-acting enzymes are exemplified non-exclusively by enzymes with polynucleotide-cleaving activity, enzymes with polynucleotide-methylating activity, enzymes with polynucleotide-ligating activity, and enzymes with a plurality of distinguishable enzymatic activities (including non-exclusively, e.g., both polynucleotide-cleaving activity and polynucleotide-ligating activity).

It is appreciated that relevant polynucleotide-acting enzymes include any enzymes identifiable by one skilled in the art (e.g., commercially available) or that may be developed in the future, though currently unavailable, that are serviceable for generating a ligation compatible end, preferably a sticky end, in a polynucleotide. It may be preferable to use restriction sites that are not contained, or alternatively that are not expected to be contained, or alternatively that are unlikely to be contained (e.g., when sequence information regarding a working polynucleotide is incomplete) internally in a polynucleotide to be subjected to end-selection. It is recognized that methods (e.g., mutagenesis methods) can be used to remove unwanted internal restriction sites. It is also appreciated that a partial digestion reaction (i.e. a digestion reaction that proceeds to partial completion) can be used to achieve digestion at a recognition site in a terminal region while sparing a susceptible restriction site that occurs internally in a polynucleotide and that is recognized by the same enzyme. In one aspect, partial digest are useful because it is appreciated that certain enzymes show preferential cleavage of the same recognition sequence depending on the location and environment in which the recognition sequence occurs.

It is also appreciated that protection methods can be used to selectively protect specified restriction sites (e.g., internal sites) against unwanted digestion by enzymes that would otherwise cut a working polypeptide in response to the presence of those sites; and that such protection methods include modifications such as methylations and base substitutions (e.g., U instead of T) that inhibit an unwanted enzyme activity.

In another embodiment of the invention, a serviceable end-selection marker is a terminal sequence that is recognized by a polynucleotide-acting enzyme that recognizes a specific polynucleotide sequence. In one aspect of the invention, serviceable polynucleotide-acting enzymes also include other enzymes in addition to classic type II restriction enzymes. According to this preferred aspect of the invention, serviceable polynucleotide-acting enzymes also include gyrases (e.g., topoisomerases), helicases, recombinases, relaxases, and any enzymes related thereto.

It is appreciated that, end-selection can be used to distinguish and separate parental template molecules (e.g., to be subjected to mutagenesis) from progeny molecules (e.g., generated by mutagenesis). For example, a first set of primers, lacking in a topoisomerase I recognition site, can be used to modify the terminal regions of the parental molecules (e.g., in polymerase-based amplification). A different second set of primers (e.g., having a topoisomerase I recognition site) can then be used to generate mutated progeny molecules (e.g., using any polynucleotide chimerization method, such as interrupted synthesis, template-switching polymerase-based amplification, or interrupted synthesis; or using saturation mutagenesis; or using any other method for introducing a topoisomerase I recognition site into a mutagenized progeny molecule) from the amplified template molecules. The use of topoisomerase I-based end-selection can then facilitate, not only discernment, but selective topoisomerase I-based ligation of the desired progeny molecules.

It is appreciated that an end-selection approach using topoisomerase-based nicking and ligation has several advantages over previously available selection methods. In sum, this approach allows one to achieve direction cloning (including expression cloning).

Peptide Display Methods

The present method can be used to shuffle, by in vitro and/or in vivo recombination by any of the disclosed methods, and in any combination, polynucleotide sequences selected by peptide display methods, wherein an associated polynucleotide encodes a displayed peptide which is screened for a phenotype (e.g., for affinity for a predetermined receptor (ligand).

An increasingly important aspect of bio-pharmaceutical drug development and molecular biology is the identification of peptide structures, including the primary amino acid sequences, of peptides or peptidomimetics that interact with biological macromolecules. One method of identifying peptides that possess a desired structure or functional property, such as binding to a predetermined biological macromolecule (e.g., a receptor), involves the screening of a large library or peptides for individual library members which possess the desired structure or functional property conferred by the amino acid sequence of the peptide.

In addition to direct chemical synthesis methods for generating peptide libraries, several recombinant DNA methods also have been reported. One type involves the display of a peptide sequence, antibody, or other protein on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member.

A well-known peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles (i.e., library members) which are bound to the immobilized macromolecule are then recovered and replicated to amplify the selected bacteriophage sub-population for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such methods are further described in PCT patent publications WO 91/17271, WO 91/18980, WO 91/19818 and WO 93/08278.

The present invention also provides random, pseudorandom, and defined sequence framework peptide libraries and methods for generating and screening those libraries to identify useful compounds (e.g., peptides, including single-chain antibodies) that bind to receptor molecules or epitopes of interest or gene products that modify peptides or RNA in a desired fashion. The random, pseudorandom, and defined sequence framework peptides are produced from libraries of peptide library members that comprise displayed peptides or displayed single-chain antibodies attached to a polynucleotide template from which the displayed peptide was synthesized. The mode of attachment may vary according to the specific embodiment of the invention selected, and can include encapsulation in a phage particle or incorporation in a cell.

A significant advantage of the present invention is that no prior information regarding an expected ligand structure is required to isolate peptide ligands or antibodies of interest. The peptide identified can have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

The invention also provides a method for shuffling a pool of polynucleotide sequences identified by the methods of the invention and selected by affinity screening a library of polysomes displaying nascent peptides (including single-chain antibodies) for library members which bind to a predetermined receptor (e.g., a mammalian proteinaceous receptor such as, for example, a peptidergic hormone receptor, a cell surface receptor, an intracellular protein which binds to other protein(s) to form intracellular protein complexes such as hetero-dimers and the like) or epitope (e.g., an immobilized protein, glycoprotein, oligosaccharide, and the like).

Polynucleotide sequences selected in a first selection round (typically by affinity selection for binding to a receptor (e.g., a ligand)) by any of these methods are pooled and the pool(s) is/are shuffled by in vitro and/or invivo recombination to produce a shuffled pool comprising a population of recombined selected polynucleotide sequences. The recombined selected polynucleotide sequences are subjected to at least one subsequent selection round. The polynucleotide sequences selected in the subsequent selection round(s) can be used directly, sequenced, and/or subjected to one or more additional rounds of shuffling and subsequent selection. Selected sequences can also be back-crossed with polynucleotide sequences encoding neutral sequences (i.e., having insubstantial functional effect on binding), such as for example by back-crossing with a wild-type or naturally-occurring sequence substantially identical to a selected sequence to produce native-like functional peptides, which may be less immunogenic. Generally, during back-crossing subsequent selection is applied to retain the property of binding to the predetermined receptor (ligand).

Prior to or concomitant with the shuffling of selected sequences, the sequences can be mutagenized. In one embodiment, selected library members are cloned in a prokaryotic vector (e.g., plasmid, phagemid, or bacteriophage) wherein a collection of individual colonies (or plaques) representing discrete library members are produced. Individual selected library members can then be manipulated (e.g., by site-directed mutagenesis, cassette mutagenesis, chemical mutagenesis, PCR mutagenesis, and the like) to generate a collection of library members representing a kernal of sequence diversity based on the sequence of the selected library member. The sequence of an individual selected library member or pool can be manipulated to incorporate random mutation, pseudorandom mutation, defined kernal mutation (i.e., comprising variant and invariant residue positions and/or comprising variant residue positions which can comprise a residue selected from a defined subset of amino acid residues), codon-based mutation, and the like, either segmentally or over the entire length of the individual selected library member sequence. The mutagenized selected library members are then shuffled by in vitro and/or invivo recombinatorial shuffling as disclosed herein.

The invention also provides peptide libraries comprising a plurality of individual library members of the invention, wherein (1) each individual library member of said plurality comprises a sequence produced by shuffling of a pool of selected sequences, and (2) each individual library member comprises a variable peptide segment sequence or single-chain antibody segment sequence which is distinct from the variable peptide segment sequences or single-chain antibody sequences of other individual library members in said plurality (although some library members may be present in more than one copy per library due to uneven amplification, stochastic probability, or the like).

The invention also provides a product-by-process, wherein selected polynucleotide sequences having (or encoding a peptide having) a predetermined binding specificity are formed by the process of: (1) screening a displayed peptide or displayed single-chain antibody library against a predetermined receptor (e.g., ligand) or epitope (e.g., antigen macromolecule) and identifying and/or enriching library members which bind to the predetermined receptor or epitope to produce a pool of selected library members, (2) shuffling by recombination the selected library members (or amplified or cloned copies thereof) which binds the predetermined epitope and has been thereby isolated and/or enriched from the library to generate a shuffled library, and (3) screening the shuffled library against the predetermined receptor (e.g., ligand) or epitope (e.g., antigen macromolecule) and identifying and/or enriching shuffled library members which bind to the predetermined receptor or epitope to produce a pool of selected shuffled library members.

Antibody Display and Screening Methods

The present method can be used to shuffle, by in vitro and/or invivo recombination by any of the disclosed methods, and in any combination, polynucleotide sequences selected by antibody display methods, wherein an associated polynucleotide encodes a displayed antibody which is screened for a phenotype (e.g., for affinity for binding a predetermined antigen (ligand)).

Various molecular genetic approaches have been devised to capture the vast immunological repertoire represented by the extremely large number of distinct variable regions which can be present in immunoglobulin chains. The naturally-occurring germ line immunoglobulin heavy chain locus is composed of separate tandem arrays of variable segment genes located upstream of a tandem array of diversity segment genes, which are themselves located upstream of a tandem array of joining (i) region genes, which are located upstream of the constant region genes. During B lymphocyte development, V-D-J rearrangement occurs wherein a heavy chain variable region gene (VH) is formed by rearrangement to form a fused D segment followed by rearrangement with a V segment to form a V-D-J joined product gene which, if productively rearranged, encodes a functional variable region (VH) of a heavy chain. Similarly, light chain loci rearrange one of several V segments with one of several J segments to form a gene encoding the variable region (VL) of a light chain.

The vast repertoire of variable regions possible in immunoglobulins derives in part from the numerous combinatorial possibilities of joining V and i segments (and, in the case of heavy chain loci, D segments) during rearrangement in B cell development. Additional sequence diversity in the heavy chain variable regions arises from non-uniform rearrangements of the D segments during V-D-J joining and from N region addition. Further, antigen-selection of specific B cell clones selects for higher affinity variants having non-germline mutations in one or both of the heavy and light chain variable regions; a phenomenon referred to as "affinity maturation" or "affinity sharpening". Typically, these "affinity sharpening" mutations cluster in specific areas of the variable region, most commonly in the complementarity-determining regions (CDRs).

In order to overcome many of the limitations in producing and identifying high-affinity immunoglobulins through antigen-stimulated β cell development (i.e., immunization), various prokaryotic expression systems have been developed that can be manipulated to produce combinatorial antibody libraries which may be screened for high-affinity antibodies to specific antigens. Recent advances in the expression of antibodies in *Escherichia coli* and bacteriophage systems (see "alternative peptide display methods", infra) have raised the possibility that virtually any specificity can be obtained by either cloning antibody genes from characterized hybridomas or by de novo selection using antibody gene libraries (e.g., from Ig cDNA).

Combinatorial libraries of antibodies have been generated in bacteriophage lambda expression systems which may be screened as bacteriophage plaques or as colonies of lysogens (Huse et al, 1989); Caton and Koprowski, 1990; Mullinax et al., 1990; Persson et al., 1991). Various embodiments of bacteriophage antibody display libraries and lambda phage expression libraries have been described (Kang et al., 1991; Clackson et al., 1991; McCafferty et al., 1990; Burton et al, 1991; Hoogenboom et al., 1991; Chang et al., 1991; Breitling et al., 1991; Marks et al., 1991, p. 581; Barbas et al., 1992; Hawkins and Winter, 1992; Marks et al., 1992, p. 779; Marks et al., 1992, p. 16007; and Lowman et al., 1991; Lerner et al., 1992; all incorporated herein by reference). Typically, a bacteriophage antibody display library is screened with a receptor (e.g., polypeptide, carbohydrate, glycoprotein, nucleic acid) that is immobilized (e.g., by covalent linkage to a chromatography resin to enrich for reactive phage by affinity chromatography) and/or labeled (e.g., to screen plaque or colony lifts).

One particularly advantageous approach has been the use of so-called single-chain fragment variable (scfv) libraries (Marks et al., 1992, p. 779; Winter and Milstein, 1991; Clackson et al., 1991; Marks et al, 1991, p. 581; Chaudhary et al., 1990; Chiswell et al., 1992; McCafferty et al., 1990; and Huston et al., 1988). Various embodiments of scfv libraries displayed on bacteriophage coat proteins have been described.

Beginning in 1988, single-chain analogues of Fv fragments and their fusion proteins have been reliably generated by antibody engineering methods. The first step generally involves obtaining the genes encoding VH and VL domains with desired binding properties; these V genes may be isolated from a specific hybridoma cell line, selected from a combinatorial V-gene library, or made by V gene synthesis. The single-chain Fv is formed by connecting the component V genes with an oligonucleotide that encodes an appropriately designed linker peptide, such as (Gly-Gly-Gly-Gly-Ser) or equivalent linker peptide(s). The linker bridges the C-terminus of the first V region and N-terminus of the second, ordered as either VH-linker-VL or VL-linker-VH'. In principle, the scfv binding site can faithfully replicate both the affinity and specificity of its parent antibody combining site.

Thus, scfv fragments are comprised of VH and VL domains linked into a single polypeptide chain by a flexible linker peptide. After the scfv genes are assembled, they are cloned into a phagemid and expressed at the tip of the M13 phage (or similar filamentous bacteriophage) as fusion proteins with the bacteriophage PIII (gene 3) coat protein. Enriching for phage expressing an antibody of interest is accomplished by panning the recombinant phage displaying a population scfv for binding to a predetermined epitope (e.g., target antigen, receptor).

The linked polynucleotide of a library member provides the basis for replication of the library member after a screening or selection procedure, and also provides the basis for the determination, by nucleotide sequencing, of the identity of the displayed peptide sequence or VH and VL amino acid sequence. The displayed peptide (s) or single-chain antibody (e.g., scfv) and/or its VH and VL domains or their CDRs can be cloned and expressed in a suitable expression system. Often polynucleotides encoding the isolated VH and VL domains will be ligated to polynucleotides encoding constant regions (CH and CL) to form polynucleotides encoding complete antibodies (e.g., chimeric or fully-human), antibody fragments, and the like. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like.

Various methods have been reported for increasing the combinatorial diversity of a scfv library to broaden the repertoire of binding species (idiotype spectrum). The use of PCR has permitted the variable regions to be rapidly cloned either from a specific hybridoma source or as a gene library from non-immunized cells, affording combinatorial diversity in the assortment of VH and VL cassettes which can be combined. Furthermore, the VH and VL cassettes can themselves be diversified, such as by random, pseudorandom, or directed mutagenesis. Typically, VH and VL cassettes are diversified in or near the complementarity-determining regions (CDRS), often the third CDR, CDR3. Enzymatic inverse PCR mutagenesis has been shown to be a simple and reliable method for constructing relatively large libraries of scfv site-directed hybrids (Stemmer et al., 1993), as has error-prone PCR and chemical mutagenesis (Deng et al., 1994). Riechmann (Riechmann et al., 1993) showed semi-rational design of an antibody scfv fragment using site-directed randomization by degenerate oligonucleotide PCR and subsequent phage display of the resultant scfv hybrids. Barbas (Barbas et al., 1992) attempted to circumvent the problem of limited repertoire sizes resulting from using biased variable region sequences by randomizing the sequence in a synthetic CDR region of a human tetanus toxoid-binding Fab.

CDR randomization has the potential to create approximately $1 \times 10^{20}$ CDRs for the heavy chain CDR3 alone, and a roughly similar number of variants of the heavy chain CDR1 and CDR2, and light chain CDR1–3 variants. Taken individually or together, the combination possibilities of CDR randomization of heavy and/or light chains requires generating a prohibitive number of bacteriophage clones to produce a clone library representing all possible combinations, the vast majority of which will be non-binding. Generation of such large numbers of primary transformants is not feasible with current transformation technology and bacteriophage display systems. For example, Barbas (Barbas et al., 1992) only generated $5 \times 10^7$ transformants, which represents only a tiny fraction of the potential diversity of a library of thoroughly randomized CDRs.

Despite these substantial limitations, bacteriophage. display of scfv have already yielded a variety of useful antibodies and antibody fusion proteins. A bispecific single chain antibody has been shown to mediate efficient tumor cell lysis (Gruber et al., 1994). Intracellular expression of an anti-Rev scfv has been shown to inhibit HIV-1 virus replication in vitro (Duan et al., 1994), and intracellular expression of an anti-p21rar, scfv has been shown to inhibit meiotic maturation of *Xenopus oocytes* (Biocca et al., 1993). Recombinant scfv which can be used to diagnose HIV infection have also been reported, demonstrating the diagnostic utility of scfv (Lilley et al., 1994). Fusion proteins wherein an scFv is linked to a second polypeptide, such as a toxin or fibrinolytic activator protein, have also been reported (Holvost et al., 1992; Nicholls et al., 1993).

If it were possible to generate scfv libraries having broader antibody diversity and overcoming many of the limitations of conventional CDR mutagenesis and randomization methods which can cover only a very tiny fraction of the potential sequence combinations, the number and quality of scfv antibodies suitable for therapeutic and diagnostic use could be vastly improved. To address this, the in vitro and invivo shuffling methods of the invention are used to recombine CDRs which have been obtained (typically via PCR amplification or cloning) from nucleic acids obtained from selected displayed antibodies. Such displayed antibodies can be displayed on cells, on bacteriophage particles, on polysomes, or any suitable antibody display system wherein the antibody is associated with its encoding nucleic acid(s). In a variation, the CDRs are initially obtained from mRNA (or cDNA) from antibody-producing cells (e.g., plasma cells/splenocytes from an immunized wild-type mouse, a human, or a transgenic mouse capable of making a human antibody as in WO 92/03918, WO 93/12227, and WO 94/25585), including hybridomas derived therefrom.

Polynucleotide sequences selected in a first selection round (typically by affinity selection for displayed antibody binding to an antigen (e.g., a ligand) by any of these methods are pooled and the pool(s) is/are shuffled by in vitro and/or invivo recombination, especially shuffling of CDRs (typically shuffling heavy chain CDRs with other heavy chain CDRs and light chain CDRs with other light chain CDRs) to produce a shuffled pool comprising a population of recombined selected polynucleotide sequences. The recombined selected polynucleotide sequences are expressed in a selection format as a displayed antibody and subjected to at least one subsequent selection round. The polynucleotide sequences selected in the subsequent selection round(s) can be used directly, sequenced, and/or subjected to one or more additional rounds of shuffling and subsequent selection until an antibody of the desired binding affinity is obtained. Selected sequences can also be back-crossed with polynucleotide sequences encoding neutral antibody framework sequences (i.e., having insubstantial functional effect on antigen binding), such as for example by back-crossing with a human variable region framework to produce human-like sequence antibodies. Generally, during back-crossing subsequent selection is applied to retain the property of binding to the predetermined antigen.

Alternatively, or in combination with the noted variations, the valency of the target epitope may be varied to control the average binding affinity of selected scfv library members. The target epitope can be bound to a surface or substrate at varying densities, such as by including a competitor epitope, by dilution, or by other method known to those in the art. A high density (valency) of predetermined epitope can be used to enrich for scfv library members which have relatively low affinity, whereas a low density (valency) can preferentially enrich for higher affinity scfv library members.

For generating diverse variable segments, a collection of synthetic oligonucleotides encoding random, pseudorandom, or a defined sequence kernal set of peptide sequences can be inserted by ligation into a predetermined site (e.g., a CDR). Similarly, the sequence diversity of one or more CDRs of the single-chain antibody cassette(s) can be expanded by mutating the CDR(s) with site-directed mutagenesis, CDR-replacement, and the like. The resultant DNA molecules can be propagated in a host for cloning and amplification prior to shuffling, or can be used directly (i.e., may avoid loss of diversity which may occur upon propagation in a host cell) and the selected library members subsequently shuffled.

Displayed peptide/polynucleotide complexes (library members) which encode a variable segment peptide sequence of interest or a single-chain antibody of interest are selected from the library by an affinity enrichment technique. This is accomplished by means of a immobilized macromolecule or epitope specific for the peptide sequence of interest, such as a receptor, other macromolecule, or other epitope species. Repeating the affinity selection procedure provides an enrichment of library members encoding the desired sequences, which may then be isolated for pooling and shuffling, for sequencing, and/or for further propagation and affinity enrichment.

The library members without the desired specificity are removed by washing. The degree and stringency of washing required will be determined for each peptide sequence or single-chain antibody of interest and the immobilized predetermined macromolecule or epitope. A certain degree of control can be exerted over the binding characteristics of the nascent peptide/DNA complexes recovered by adjusting the conditions of the binding incubation and the subsequent washing. The temperature, pH, ionic strength, divalent cations concentration, and the volume and duration of the washing will select for nascent peptide/DNA complexes within particular ranges of affinity for the immobilized macromolecule. Selection based on slow dissociation rate, which is usually predictive of high affinity, is often the most practical route. This may be done either by continued incubation in the presence of a saturating amount of free predetermined macromolecule, or by increasing the volume, number, and length of the washes. In each case, the rebinding of dissociated nascent peptide/DNA or peptide/RNA complex is prevented, and with increasing time, nascent peptide/DNA or peptide/RNA complexes of higher and higher affinity are recovered.

Additional modifications of the binding and washing procedures may be applied to find peptides with special characteristics. The affinities of some peptides are dependent on ionic strength or cation concentration. This is a useful characteristic for peptides that will be used in affinity purification of various proteins when gentle conditions for removing the protein from the peptides are required.

One variation involves the use of multiple binding targets (multiple epitope species, multiple receptor species), such that a scfv library can be simultaneously screened for a multiplicity of scfv which have different binding specificities. Given that the size of a scfv library often limits the diversity of potential scfv sequences, it is typically desirable to us scfv libraries of as large a size as possible. The time and economic considerations of generating a number of very large polysome scFv-display libraries can become prohibitive. To avoid this substantial problem, multiple predetermined epitope species (receptor species) can be concomitantly screened in a single library, or sequential screening against a number of epitope species can be used. In one variation, multiple target epitope species, each encoded on a separate bead (or subset of beads), can be mixed and incubated with a polysome-display scfv library under suitable binding conditions. The collection of beads, comprising multiple epitope species, can then be used to isolate, by affinity selection, scfv library members. Generally, subsequent affinity screening rounds can include the same mixture of beads, subsets thereof, or beads containing only one or two individual epitope species. This approach affords efficient screening, and is compatible with laboratory automation, batch processing, and high throughput screening methods.

A variety of techniques can be used in the present invention to diversify a peptide library or single-chain antibody library, or to diversify, prior to or concomitant with shuffling, around variable segment peptides found in early rounds of panning to have sufficient binding activity to the predetermined macromolecule or epitope. In one approach, the positive selected peptide/polynucleotide complexes (those identified in an early round of affinity enrichment) are sequenced to determine the identity of the active peptides. Oligonucleotides are then synthesized based on these active peptide sequences, employing a low level of all bases incorporated at each step to produce slight variations of the primary oligonucleotide sequences. This mixture of (slightly) degenerate oligonucleotides is then cloned into the variable segment sequences at the appropriate locations. This method produces systematic, controlled variations of the starting peptide sequences, which can then be shuffled. It requires, however, that individual positive nascent peptide/polynucleotide complexes be sequenced before mutagenesis, and thus is useful for expanding the diversity of small numbers of recovered complexes and selecting variants having higher binding affinity and/or higher binding specificity. In a variation, mutagenic PCR amplification of positive selected peptide/polynucleotide complexes (especially of the variable region sequences, the amplification products of which are shuffled in vitro and/or invivo and one or more additional rounds of screening is done prior to sequencing. The same general approach can be employed with single-chain antibodies in order to expand the diversity and enhance the binding affinity/specificity, typically by diversifying CDRs or adjacent framework regions prior to or concomitant with shuffling. If desired, shuffling reactions can be spiked with mutagenic oligonucleotides capable of in vitro recombination with the selected library members can be included. Thus, mixtures of synthetic oligonucleotides and PCR produced polynucleotides (synthesized by error-prone or high-fidelity methods) can be added to the in vitro shuffling mix and be incorporated into resulting shuffled library members (shufflants).

The invention of shuffling enables the generation of a vast library of CDR-variant single-chain antibodies. One way to generate such antibodies is to insert synthetic CDRs into the single-chain antibody and/or CDR randomization prior to or concomitant with shuffling. The sequences of the synthetic CDR cassettes are selected by referring to known sequence data of human CDR and are selected in the discretion of the practitioner according to the following guidelines: synthetic CDRs will have at least 40 percent positional sequence identity to known CDR sequences, and preferably will have at least 50 to 70 percent positional sequence identity to known CDR sequences. For example, a collection of synthetic CDR sequences can be generated by synthesizing a collection of oligonucleotide sequences on the basis of naturally-occurring human CDR sequences listed in Kabat (Kabat et al., 1991); the pool(s) of synthetic CDR sequences are calculated to encode CDR peptide sequences having at least 40 percent sequence identity to at least one known naturally-occurring human CDR sequence. Alternatively, a collection of naturally-occurring CDR sequences may be compared to generate consensus sequences so that amino acids used at a residue position frequently (i.e., in at least 5 percent of known CDR sequences) are incorporated into the synthetic CDRs at the corresponding position(s). Typically, several (e.g., 3 to about 50) known CDR sequences are compared and observed natural sequence variations between the known CDRs are tabulated, and a collection of oligonucleotides encoding CDR peptide sequences encompassing all or most permutations of the observed natural sequence variations is synthesized. For example but not for limitation, if a collection of human VH CDR sequences have carboxy-terminal amino acids which are either Tyr, Val, Phe, or Asp, then the pool(s) of synthetic CDR oligonucleotide sequences are designed to allow the carboxy-terminal CDR residue to be any of these amino acids. In some embodiments, residues other than those which naturally-occur at a residue position in the collection of CDR sequences are incorporated: conservative amino acid substitutions are frequently incorporated and up to 5 residue positions may be varied to incorporate non-conservative amino acid substitutions as compared to known naturally-occurring CDR sequences. Such CDR sequences can be used in primary library members (prior to first round screening) and/or can be used to spike in vitro shuffling reactions of selected library member sequences. Construction of such pools of defined and/or degenerate sequences will be readily accomplished by those of ordinary skill in the art.

The collection of synthetic CDR sequences comprises at least one member that is not known to be a naturally-occurring CDR sequence. It is within the discretion of the practitioner to include or not include a portion of random or pseudorandom sequence corresponding to N region addition in the heavy chain CDR; the N region sequence ranges from 1 nucleotide to about 4 nucleotides occurring at V-D and D-J junctions. A collection of synthetic heavy chain CDR sequences comprises at least about 100 unique CDR sequences, typically at least about 1,000 unique CDR sequences, preferably at least about 10,000 unique CDR sequences, frequently more than 50,000 unique CDR sequences; however, usually not more than about $1\times10^6$ unique CDR sequences are included in the collection, although occasionally $1\times10^7$ to $1\times10^8$ unique CDR sequences are present, especially if conservative amino acid substitutions are permitted at positions where the conservative amino acid substituent is not present or is rare (i.e., less than 0.1 percent) in that position in naturally-occurring human CDRS. In general, the number of unique CDR sequences included in a library should not exceed the expected number of primary transformants in the library by more than a factor of 10. Such single-chain antibodies generally bind of about at least $1\times10$ m–, preferably with an affinity of about at least $5\times10^7$ M–1, more preferably with an affinity of at least $1\times10^8$ M–1 to $1\times10^9$ M–1 or more, sometimes up to $1\times10^{10}$ M–1 or more. Frequently, the predetermined antigen is a human protein, such as for example a human cell surface antigen (e.g., CD4, CD8, IL-2 receptor, EGF receptor, PDGF receptor), other human biological macromolecule (e.g., thrombomodulin, protein C, carbohydrate antigen, sialyl Lewis antigen, L-selectin), or nonhuman disease associated macromolecule (e.g., bacterial LPS, virion capsid protein or envelope glycoprotein) and the like.

High affinity single-chain antibodies of the desired specificity can be engineered and expressed in a variety of systems. For example, scfv have been produced in plants (Firek et al., 1993) and can be readily made in prokaryotic systems (Owens and Young, 1994; Johnson and Bird, 1991). Furthermore, the single-chain antibodies can be used as a basis for constructing whole antibodies or various fragments thereof (Kettleborough et al., 1994). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, 1982). Once purified, partially or to homogeneity as desired, the polypeptides may then be used therapeutically or in developing and performing assay procedures, immunofluorescent stainings, and the like (see, generally, Lefkovits and Pernis, 1979 and 1981; Lefkovits, 1997).

The antibodies generated by the method of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens and binding members well known to those skilled in the art.

Shuffling can also be used to recombinatorially diversify a pool of selected library members obtained by screening a two-hybrid screening system to identify library members which bind a predetermined polypeptide sequence. The selected library members are pooled and shuffled by in vitro and/or invivo recombination. The shuffled pool can then be screened in a yeast two hybrid system to select library members which bind said predetermined polypeptide sequence (e.g., and SH2 domain) or which bind an alternate predetermined polypeptide sequence (e.g., an SH2 domain from another protein species).

An approach to identifying polypeptide sequences which bind to a predetermined polypeptide sequence has been to use a so-called "two-hybrid" system wherein the predetermined polypeptide sequence is present in a fusion protein (Chien et al., 1991). This approach identifies protein-protein interactions invivo through reconstitution of a transcriptional activator (Fields and Song, 1989), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacz, HIS3) which is operably linked to a Gal4 binding site. Typically, the two-hybrid method is used to identify novel polypeptide sequences which interact with a known protein (Silver and Hunt, 1993; Durfee et al, 1993; Yang et al., 1992; Luban et al., 1993; Hardy et al., 1992; Bartel et al., 1993; and Vojtek et al, 1993). However, variations of the two-hybrid method have been used to identify mutations of a known protein that affect its binding to a second known protein (Li and Fields, 1993; Lalo et al., 1993; Jackson et al., 1993; and Madura et al., 1993). Two-hybrid systems have also been used to identify interacting structural domains of two known proteins (Bardwell et al., 1993; Chakrabarty et al., 1992; Staudinger et al., 1993; and Milne and Weaver 1993) or domains responsible for oligomerization of a single protein (Iwabuchi et al., 1993; Bogerd et al., 1993). Variations of two-hybrid systems have been used to study the invivo activity of a proteolytic enzyme (Dasmahapatra et al., 1992). Alternatively, an *E. coli*/BCCP interactive screening system (Germino et al., 1993; Guarente, 1993) can be used to identify interacting protein sequences (i.e., protein sequences which heterodimerize or form higher order heteromultimers). Sequences selected by a two-hybrid system can be pooled and shuffled and introduced into a two-hybrid system for one or more subsequent rounds of screening to identify polypeptide sequences which bind to the hybrid containing the predetermined binding sequence. The sequences thus identified can be compared to identify consensus sequence(s) and consensus sequence kernals.

One microgram samples of template DNA are obtained and treated with U.V. light to cause the formation of dimers, including TT dimers, particularly purine dimers. U.V. exposure is limited so that only a few photoproducts are generated per gene on the template DNA sample. Multiple samples are treated with U.V. light for varying periods of time to obtain template DNA samples with varying numbers of dimers from U.V. exposure.

A random priming kit which utilizes a non-proofreading polymerase (for example, Prime-It II Random Primer Labeling kit by Stratagene Cloning Systems) is utilized to generate different size polynucleotides by priming at random sites on templates which are prepared by U.V. light (as described above) and extending along the templates. The priming protocols such as described in the Prime-It II Random Primer Labeling kit may be utilized to extend the primers. The dimers formed by U.V. exposure serve as a roadblock for the extension by the non-proofreading polymerase. Thus, a pool of random size polynucleotides is present after extension with the random primers is finished.

The invention is further directed to a method for generating a selected mutant polynucleotide sequence (or a population of selected polynucleotide sequences) typically in the form of amplified and/or cloned polynucleotides, whereby the selected polynucleotide sequences(s) possess at least one desired phenotypic characteristic (e.g., encodes a polypeptide, promotes transcription of linked polynucleotides, binds a protein, and the like) which can be selected for. One method for identifying hybrid polypeptides that possess a desired structure or functional property, such as binding to a predetermined biological macromolecule (e.g., a receptor), involves the screening of a large library of polypeptides for individual library members which possess the desired structure or functional property conferred by the amino acid sequence of the polypeptide.

In one embodiment, the present invention provides a method for generating libraries of displayed polypeptides or displayed antibodies suitable for affinity interaction screening or phenotypic screening. The method comprises (1) obtaining a first plurality of selected library members comprising a displayed polypeptide or displayed antibody and an associated polynucleotide encoding said displayed polypeptide or displayed antibody, and obtaining said associated polynucleotides or copies thereof wherein said associated polynucleotides comprise a region of substantially identical sequences, optimally introducing mutations into said polynucleotides or copies, (2) pooling the polynucleotides or copies, (3) producing smaller or shorter polynucleotides by interrupting a random or particularized priming and synthesis process or an amplification process, and (4) performing amplification, preferably PCR amplification, and optionally mutagenesis to homologously recombine the newly synthesized polynucleotides.

It is an object of the invention to provide a process for producing hybrid polynucleotides which express a useful hybrid polypeptide by a series of steps comprising:
 (a) producing polynucleotides by interrupting a polynucleotide amplification or synthesis process with a means for blocking or interrupting the amplification or synthesis process and thus providing a plurality of smaller or shorter polynucleotides due to the replication of the polynucleotide being in various stages of completion;
 (b) adding to the resultant population of single- or double-stranded polynucleotides one or more single- or double-stranded oligonucleotides, wherein said added oligonucleotides comprise an area of identity in an area of heterology to one or more of the single- or double-stranded polynucleotides of the population;
 (c) denaturing the resulting single- or double-stranded oligonucleotides to produce a mixture of single-stranded polynucleotides, optionally separating the shorter or smaller polynucleotides into pools of polynucleotides having various lengths and further optionally subjecting said polynucleotides to a PCR procedure to amplify one or more oligonucleotides comprised by at least one of said polynucleotide pools;

(d) incubating a plurality of said polynucleotides or at least one pool of said polynucleotides with a polymerase under conditions which result in annealing of said single-stranded polynucleotides at regions of identity between the single-stranded polynucleotides and thus forming of a mutagenized double-stranded polynucleotide chain;

(e) optionally repeating steps (c) and (d);

(f) expressing at least one hybrid polypeptide from said polynucleotide chain, or chains; and (g) screening said at least one hybrid polypeptide for a useful activity.

In a one aspect of the invention, the means for blocking or interrupting the amplification or synthesis process is by utilization of UV light, DNA adducts, DNA binding proteins.

In one embodiment of the invention, the DNA adducts, or polynucleotides comprising the DNA adducts, are removed from the polynucleotides or polynucleotide pool, such as by a process including heating the solution comprising the DNA fragments prior to further processing.

The clones which are identified as having a desired specified activity may then be sequenced to identify the DNA sequence encoding a polypeptide (e.g., an enzyme) having the specified activity. Thus, in accordance with the present invention it is possible to isolate and identify: (i) DNA encoding an enzyme having a specified enzyme activity, (ii) enzymes having such activity (including the amino acid sequence thereof) and (iii) produce recombinant enzymes having such activity.

Suitable clones (e.g., 1–1000 or more clones) from the library are identified by the methods of the invention and sequenced using, for example, high through-put sequencing techniques. The exact method of sequencing is not a limiting factor of the invention. Any method useful in identifying the sequence of a particular cloned DNA sequence can be used. In general, sequencing is an adaptation of the natural process of DNA replication. Therefore, a template (e.g., the vector) and primer sequences are used. One general template preparation and sequencing protocol begins with automated picking of bacterial colonies, each of which contains a separate DNA clone which will function as a template for the sequencing reaction. The selected clones are placed into media, and grown overnight. The DNA templates are then purified from the cells and suspended in water. After DNA quantification, high-throughput sequencing is performed using a sequencers, such as Applied Biosystems, Inc., Prism 377 DNA Sequencers. The resulting sequence data can then be used in additional methods, including searching a database or databases.

A number of source databases are available that contain either a nucleic acid sequence and/or a deduced amino acid sequence for use with the invention in identifying or determining the activity encoded by a particular polynucleotide sequence. All or a representative portion of the sequences (e.g., about 100 individual clones) to be tested are used to search a sequence database (e.g., GenBank, PFAM or ProDom), either simultaneously or individually. A number of different methods of performing such sequence searches are known in the art. The databases can be specific for a particular organism or a collection of organisms. For example, there are databases for the C. elegans, Arabadopsis. sp., M. genitalium, M. jannaschii, E. coli, H. influenzae, S. cerevisiae and others. The sequence data of the clone is then aligned to the sequences in the database or databases using algorithms designed to measure homology between two or more sequences.

Such sequence alignment methods include, for example, BLAST (Altschul et al., 1990), BLITZ (MPsrch) (Sturrock & Collins, 1993), and FASTA (Person & Lipman, 1988). The probe sequence (e.g., the sequence data from the clone) can be any length, and will be recognized as homologous based upon a threshold homology value. The threshold value may be predetermined, although this is not required. The threshold value can be based upon the particular polynucleotide length. To align sequences a number of different procedures can be used. Typically, Smith-Waterman or Needleman-Wunsch algorithms are used. However, as discussed faster procedures such as BLAST, FASTA, PSI-BLAST can be used.

For example, optimal alignment of sequences for aligning a comparison window may be conducted by the local homology algorithm of Smith (Smith and Waterman, Adv Appl Math, 1981; Smith and Waterman, J Teor Biol, 1981; Smith and Waterman, J Mol Biol, 1981; Smith et al, J Mol Evol, 1981), by the homology alignment algorithm of Needleman (Needleman and Wuncsch, 1970), by the search of similarity method of Pearson (Pearson and Lipman, 1988), by computerized implementations of these algorithms (GAP, BESTFIT, FASTA, and TFASTA in the Wisconsin Genetics Software Package Release 7.0, Genetics Computer Group, 575 Science Dr., Madison, Wis., or the Sequence Analysis Software Package of the Genetics Computer Group, University of Wisconsin, Madison, Wis.), or by inspection, and the best alignment (i.e., resulting in the highest percentage of homology over the comparison window) generated by the various methods is selected. The similarity of the two sequence (i.e., the probe sequence and the database sequence) can then be predicted.

Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned.

One example of a useful algorithm is BLAST and BLAST 2.0 algorithms, which are described in Altschul et al., Nuc. Acids Res. 25: 3389–3402 (1977) and Altschul et al., J. Mol. Biol. 215: 403–410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands.

The BLAST algorithm also performs a statistical analysis of the similarity between two sequences (see, e.g., Karlin & Altschul, Proc. Natl. Acad. Sci. USA 90: 5873 (1993)). One measure of similarity provided by BLAST algorithm is the smallest sum probability (P(N)), which provides an indication of the probability by which a match between two nucleotide sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

Sequence homology means that two polynucleotide sequences are homolgous (i.e., on a nucleotide-by-nucleotide basis) over the window of comparison. A percentage of sequence identity or homology is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence homology. This substantial homology denotes a characteristic of a polynucleotide sequence, wherein the polynucleotide comprises a sequence having at least 60 percent sequence homology, typically at least 70 percent homology, often 80 to 90 percent sequence homology, and most commonly at least 99 percent sequence homology as compared to a reference sequence of a comparison window of at least 25–50 nucleotides, wherein the percentage of sequence homology is calculated by comparing the reference sequence to the polynucleotide sequence which may include deletions or additions which total 20 percent or less of the reference sequence over the window of comparison.

Sequences having sufficient homology can the be further identified by any annotations contained in the database, including, for example, species and activity information. Accordingly, in a typical environmental sample, a plurality of nucleic acid sequences will be obtained, cloned, sequenced and corresponding homologous sequences from a database identified. This information provides a profile of the polynucleotides present in the sample, including one or more features associated with the polynucleotide including the organism and activity associated with that sequence or any polypeptide encoded by that sequence based on the database information. As used herein "fingerprint" or "profile" refers to the fact that each sample will have associated with it a set of polynucleotides characteristic of the sample and the environment from which it was derived. Such a profile can include the amount and type of sequences present in the sample, as well as information regarding the potential activities encoded by the polynucleotides and the organisms from which polynucleotides were derived. This unique pattern is each sample's profile or fingerprint.

In some instances it may be desirable to express a particular cloned polynucleotide sequence once its identity or activity is determined or an suggested identity or activity is associated with the polynucleotide. In such instances the desired clone, if not already cloned into an expression vector, is ligated downstream of a regulatory control element (e.g., a promoter or enhancer) and cloned into a suitable host cell. Expression vectors are commercially available along with corresponding host cells for use in the invention.

As representative examples of expression vectors which may be used there may be mentioned viral particles, baculovirus, phage, plasmids, phagemids, cosmids, phosmids, bacterial artificial chromosomes, viral nucleic acid (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus, yeast, etc.) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE70, pQE60, pQE-9 (Qiagen), psiX174, pBluescript SK, pBluescript KS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene), pSVK3, pBPV, pMSG, pSVL (Pharmacia). However, any other plasmid or vector may be used as long as they are replicable and viable in the host.

The nucleic acid sequence in the expression vector is operatively linked to an appropriate expression control sequence(s) (promoter) to direct mRNA synthesis. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors typically contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The nucleic acid sequence(s) selected, cloned and sequenced as hereinabove described can additionally be introduced into a suitable host to prepare a library which is screened for the desired enzyme activity. The selected nucleic acid is preferably already in a vector which includes appropriate control sequences whereby a selected nucleic acid encoding an enzyme may be expressed, for detection of the desired activity. The host cell can be a higher eukaryotic cell, such as a mammalian cell, or a lower eukaryotic cell, such as a yeast cell, or the host cell can be a prokaryotic cell, such as a bacterial cell. The selection of an appropriate host is deemed to be within the scope of those skilled in the art from the teachings herein.

In some instances it may be desirable to perform an amplification of the nucleic acid sequence present in a sample or a particular clone that has been isolated. In this embodiment, the nucleic acid sequence is amplified by PCR reaction or similar reaction known to those of skill in the art. Commercially available amplification kits are available to carry out such amplification reactions.

In addition, it is important to recognize that the alignment algorithms and searchable database can be implemented in computer hardware, software or a combination thereof. Accordingly, the isolation, processing and identification of nucleic acid sequences and the corresponding polypeptides encoded by those sequence can be implemented in an automated system.

The invention will now be described in greater detail by reference to the following non-limiting examples.

EXAMPLES

Example 1

DNA isolation. DNA is isolated using the IsoQuick Procedure as per manufacture's instructions (Orca Research Inc., Bothell, Wash.). The isolated DNA can optionally be normalized according to Example 2 (below). Upon isolation, the DNA is sheared by pushing and pulling the DNA through a 25-gauge double-hub needle and a 1-cc syringe about 500 times. A small amount is run on a 0.8% agarose gel to make sure the majority of the DNA is in the desired size range (about 3–6 kb).

Blunt-ending DNA. The DNA is blunt-ended by mixing 45 $\mu$l of 10× Mung Bean Buffer, 2.0 $\mu$l Mung Bean Nuclease (1050 u/$\mu$l) and water to a final volume of 405 $\mu$l. The mixture is incubated at 37° C. for 15 minutes. The mixture is phenol:chloroform extracted, followed by an additional chloroform extraction. One ml of ice cold ethanol is added to the final extract to precipitate the DNA. The DNA is precipitated for 10 minutes on ice. The DNA is removed by centrifugation in a microcentrifuge for 30 minutes. The pellet is washed with 1 ml of 70% ethanol and repelleted in the microcentrifuge. Following centrifugation, the DNA is dried and gently resuspended in 26 $\mu$l of TE buffer.

Methylation of DNA. The DNA is methylated by mixing 4 $\mu$l of 10× EcoRI Methylase Buffer, 0.5 $\mu$l SAM (32 mM), 5.0 $\mu$l EcoRI Methylase (40 u/$\mu$l) and incubating t 37° C. for 1 hour. In order to insure blunt ends, the following can be added to the methylation reaction: 5.0 $\mu$l of 100 mM MgCl2, 8.0 $\mu$l of dNTP mix (2.5 mM of each dGTP, DATP, dTTP, dCTP), 4.0 $\mu$l of Klenow (5 u/$\mu$l). The mixture is then incubated at 12° C. for 30 minutes.

After incubating for 30 minutes 450 $\mu$l 1× STE is added. The mixture is phenol/chloroform extracted once followed by an additional chloroform extraction. One ml of ice cold ethanol is added to the final extract to precipitate the DNA. The DNA is precipitated for 10 minutes on ice. The DNA is removed by centrifugation in a microcentrifuge for 30 minutes. The pellet is washed with 1 ml of 70% ethanol, repelleted in the microcentrifuge and allowed to dry for 10 minutes.

Ligation. The DNA is ligated by gently resuspending the DNA in 8 $\mu$l EcoRI adapters (from Stratagene's cDNA Synthesis Kit), 1.0 $\mu$l of 10× ligation buffer, 1.0 $\mu$l of 10 mM rATP, 1.0 $\mu$l of T4 DNA Ligase (4Wu/$\mu$l) and incubating at 4° C. for 2 days. The ligation reaction is terminated by heating for 30 minutes at 70° C.

Phosphorylation of adapters. The adapter ends are phosphorylated by mixing the ligation reaction with 1.0 $\mu$l of 10× Ligation Buffer, 2.0 $\mu$l of 10 mM rATP, 6.0 $\mu$l of H2O, 1.0 $\mu$l of polynucleotide kinase (PNK), and incubating at 37° C. for 30 minutes. After incubating for 30 minutes, 31 $\mu$l of H2O and 5 ml of 10× STE are added to the reaction and the sample is size fractionated on a Sephacryl S-500 spin column. The pooled fractions (1–3) are phenol/chloroform extracted once, followed by an additional chloroform extraction. The DNA is precipitated by the addition of ice cold ethanol on ice for 10 minutes. The precipitate is pelleted by centrifugation in a microcentrifuge at high speed for 30 minutes. The resulting pellet is washed with 1 ml 70% ethanol, replleted by centrifugation and allowed to dry for 10 minutes. The sample is resuspended in 10.5 $\mu$l TE buffer. The sample is not plated, but is ligated directly to lambda arms as described above, except 2.5 $\mu$l of DNA and no water is used.

Sucrose Gradient (2.2 ml) Size Fractionation. Ligation is stopped by heating the sample to 65° C. for 10 minutes. The sample is gently loaded on a 2.2 ml sucrose gradient and centrifuged in a mini-ultracentrifuge 45 k rpm at 20° C. for 4 hours (no brake). Fractions are collected by puncturing the bottom of the gradient tube with a 20-gauge needle and allowing the sucrose to flow through the needle. The first 20 drops are collected in a Falcon 2059 tube, and then ten 1-drop fractions (labeled 1–10) are collected. Each drop is about 60 $\mu$l in volume. Five $\mu$l of each fraction are run on a 0.8% agarose gel to check the size. Fractions 1–4 (about 10–1.5 kb) are pooled and, in a separate tube, fractions 5–7 (about 5–0.5 kb) are pooled. One ml of ice cold ethanol is added to precipitate the DNA and then placed on ice for 10 minutes. The precipitate is pelleted by centrifugation in a microcentrifuge at high speed for 30 minutes. The pellets are washed by resuspending them in 1 ml of 70% ethanol and repelleting them by centrifugation in a microcentrifuge at high speed for 10 minutes, and then dried. Each pellet is then resuspended in 10 $\mu$l of TE buffer.

Test Ligation to Lambda Arms. The assay is plated by spotting 0.5 $\mu$l of the sample on agarose containing ethidium bromide along with standards (DNA sample of known concentration) to get an approximate concentration. The samples are then viewed using UV light and the estimated concentration is compared to the standards.

The following ligation reaction (5 $\mu$l reactions) are prepared and incubated at 4° C. overnight, as shown in Table 1 below:

TABLE 1

| Sample | H2O | 10× Ligase | 10 mM rATP | Lambda arms (ZAP) | Insert DNA | T4 DNA Ligase |
|---|---|---|---|---|---|---|
| Fraction 1–4 | 0.5 $\mu$l | 0.5 $\mu$l | 0.5 $\mu$l | 1.0 $\mu$l | 2.0 $\mu$l | 0.5 $\mu$l |
| Fraction 5–7 | 0.5 $\mu$l | 0.5 $\mu$l | 0.5 $\mu$l | 1.0 $\mu$l | 2.0 $\mu$l | 0.5 $\mu$l |

Test Package and Plate. The ligation reactions are packaged following manufacturer's protocol. Packaging reactions are stopped with 500 $\mu$l SM buffer and pooled with packaging that came from the same ligation. On $\mu$l of each pooled reaction is titered on an appropriate host (OD600= 1.0) (XL1-Blue MRF). 200 μl host (in MgSO4) are added to Falcon 2059 tubes, inoculated with 1 μl packaged phage and incubated at 37° C. for 15 minutes. About 3 ml of 48° C. top agar (50 ml stock containing 150 μl IPTG (0.5 M) and 300 μl X-GAL (350 mg/ml)) are added and plated on 100 mm plates. The plates are incubated overnight at 37° C.

Amplification of Libraries ($5.0 \times 10^5$ recombinants from each library). About 3.0 ml host cells (OD600=1.0) are added to two 50 ml conical tubes, inoculated with $2.5 \times 10^5$ pfu of phage per conical tube, and then incubated at 37° C. for 20 minutes. Top agar is added to each tube to a final volume of 45 ml. Each tube is plated across five 150 mm plates. The plates are incubated at 37° C. for 6–8 hours or until plaques are about pin-head in size. The plates are overlaid with 8–10 ml SM Buffer and placed at 4° C. overnight (with gentle rocking if possible).

Harvest Phage. The phage suspension is recovered by pouring the SM buffer off each plate into a 50 ml conical tube. About 3 ml of chloroform are added, shaken vigorously and incubated at room temperature for 15 minutes. The tubes are centrifuged at 2K rpm for 10 minutes to remove cell debris. The supernatant is poured into a sterile flask, 500 μl chloroform are added and stored at 4° C.

Titer Amplified Library. Serial dilutions of the harvested phage are made (for example, $10^{-5}$=1 μl amplified phage in 1 ml SM Buffer; $10^{-6}$=1 μl of the $10^{-3}$ dilution in 1 ml SM Buffer etc.), and 200 μl host (in 10 mM MgSO$_4$) are added to two tubes. One tube is inoculated with 10 μl of $10^{-6}$ dilution ($10^{-5}$). The other tube is inoculated with 1 μl of $10^{-6}$ dilution ($10^{-6}$), and incubated at 37° C. for 15 minutes.

About 3 ml of 48° C. top agar (50 ml stock containing 150 μl IPTG (0.5 M) and 37 μl X-GA (350 mg/ml)) are added to each tube and plated on 100 mm plates. The plates are incubated overnight at 37° C.

The ZAP II library is excised to create the pBLUE-SCRIPT library according to manufacturer's protocols (Stratagene).

The DNA library can be transformed into host cells (e.g., *E. coli*) to generate an expression library of clones.

Example 2

Normalization

Prior to library generation, purified DNA can be normalized. DNA is first fractionated according to the following protocol. A sample composed of genomic DNA is purified on a cesium-chloride gradient. The cesium chloride (Rf= 1.3980) solution is filtered through a 0.2 um filter and 15 ml is loaded into a 35 ml OptiSeal tube (Beckman). The DNA is added and thoroughly mixed. Ten micrograms of bis-benzimide (Sigma; Hoechst 33258) is added and mixed thoroughly. The tube is then filled with the filtered cesium chloride solution and spun in a Bti50 rotor in a Beckman L8–70 Ultracentrifuge at 33 k rpm for 72 hours. Following centrifugation, a syringe pump and fractionator (Brandel Model 186) are used to drive the gradient through an ISCO UA-5UV absorbance detector set to 280 nm. Peaks representing the DNA from the organisms present in an environmental sample are obtained. Eubacterial sequences can be detected by PCR amplification of DNA encoding rRNA from a 10 fold dilution of the *E. coli* peak using the following primers to amplify:

```
                                        (SEQ ID NO:1)
Forward primer: 5'-AGAGTTTGATCCTGGCTCAG-3'
                                        (SEQ ID NO:2)
Reverse primer: 5'-GGTTACCTTGTTACGACTT-3'
```

Recovered DNA is sheared or enzymatically digested to 3–6 kb fragments. Lone-linker primers are ligated and the DNA is size-selected. Size-selected DNA is amplified by PCR, if necessary.

Normalization is then accomplished by resuspending the double-stranded DNA sample in hybridization buffer (0.12 M NaH$_2$PO$_4$, pH 6.8/0.82 M NaCl/1 mM EDTA/0.1% SDS). The sample is overlaid with mineral oil and denatured by boiling for 10 minutes. The sample is incubated at 68° C. for 12–36 hours. Double-stranded DNA is separated from single-stranded DNA according to standard protocols (Sambrook, 1989) on hydroxyapatite at 60° C. The single-stranded DNA fraction is desalted and amplified by PCR. The process is repeated for several more rounds (up to 5 or more).

Example 3

Evaporation

Figure 8:
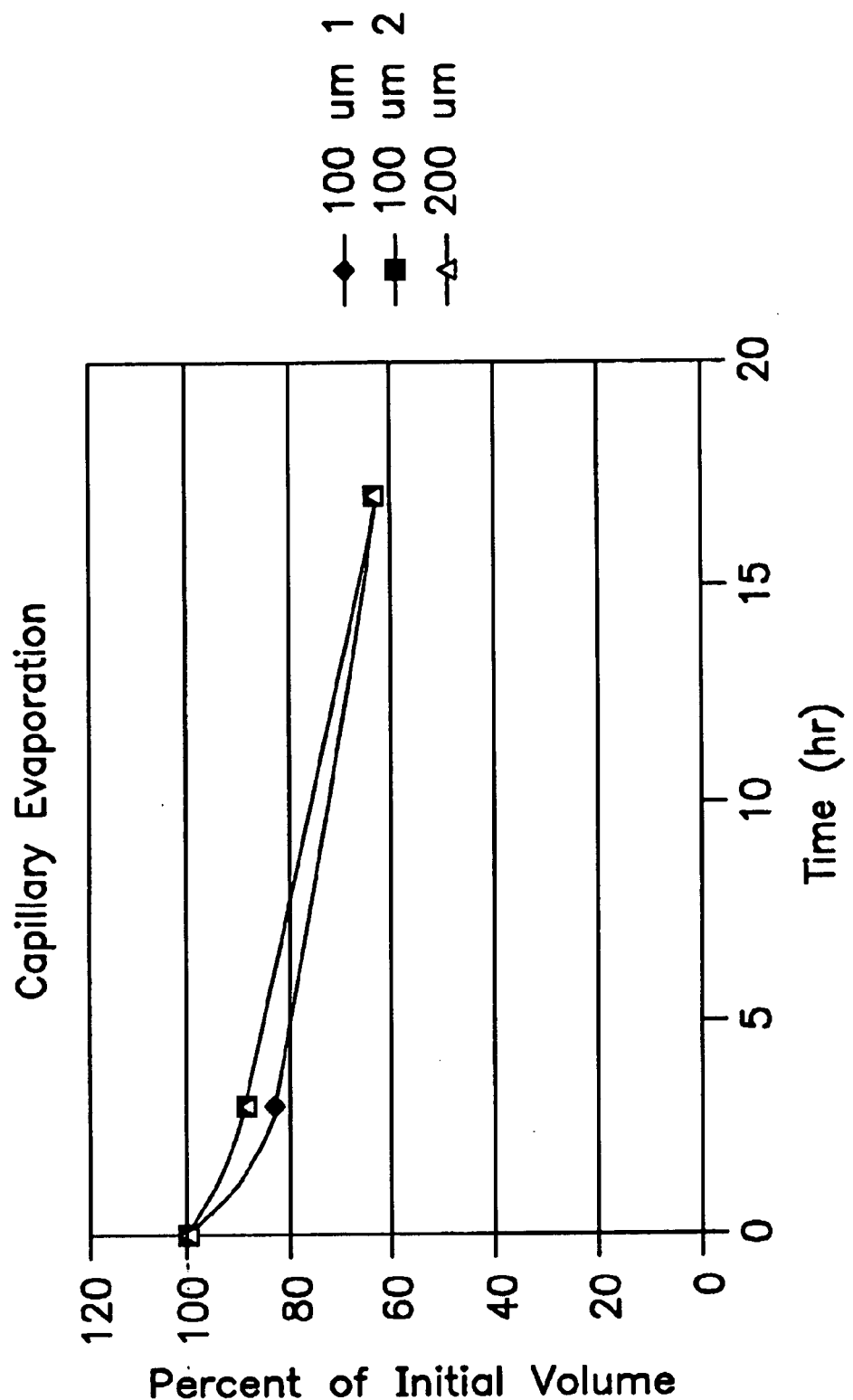
FIG. 8 is a graph showing the evaporation capillary tube contents over time as a percent of the initial volume.

Water was wicked into arrays comprised of capillaries having 100 μm and 200 μm diameter and that were 25 and 20 mm long respectively. The arrays were weighed initially (t=0) and subsequent time periods. The arrays were incubated at 37° C. and 85% humidity in a humidified incubator. Volumes were calculated from the weights. The experiment demonstrated that 25% of the volume was loss in 5 hours and 37% in 17 hours (FIG. 8).

Figure 9A:
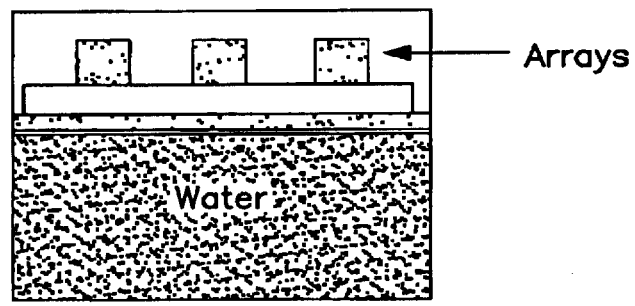
FIG. 9A is a schematic depicting a humidified chamber used for culturing capillary arrays.
Figure 9B:
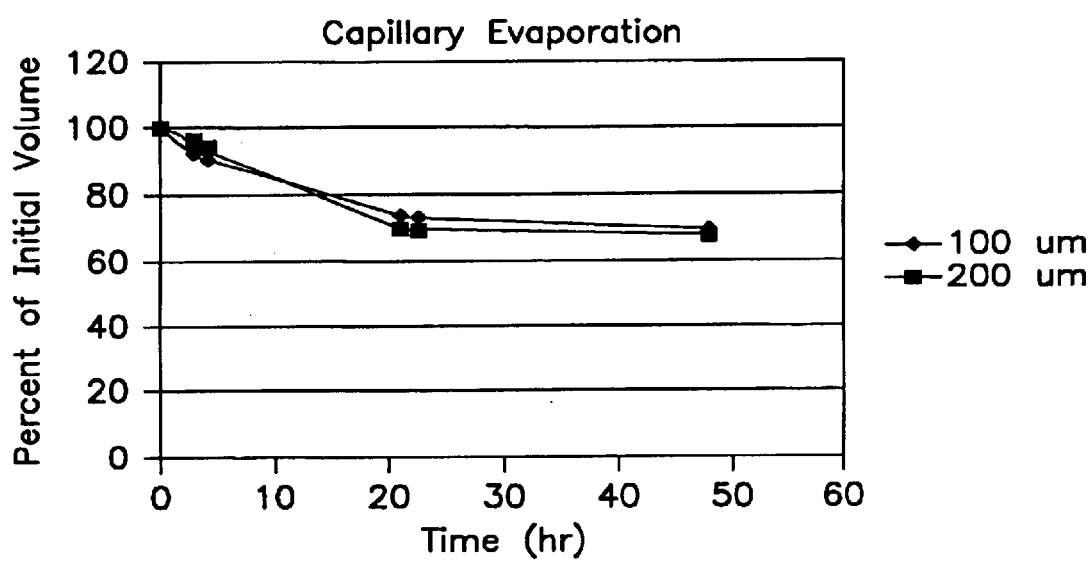
FIG. 9B shows a graph of the evaporation rate of capillary tube content (as a percent of initial volume) using the humidified chamber of FIG. 9A.

In a subsequent experiment a humid chamber was made from a pipette tip box with the arrays on the tip rack and water in the bottom of the box (FIG. 9A). The arrays were placed on the tip rack on their sides (capillaries oriented horizontally) during incubation. This incubation method provided a 7–10% loss over 5 hours and a 30% loss over 48 hours (FIG. 9B).

Example 4

535 GL2 β-galactosidase positive cells and negative control MD 24.6 cells were grown in liquid culture. Cells were diluted to 300 cells per ml and 80 μl of this dilution was placed in the well of a 384 well plate. Resorufin β-gal was added to give final concentrations of 5 uM, 50 uM, and 500 uM.

Figure 10:
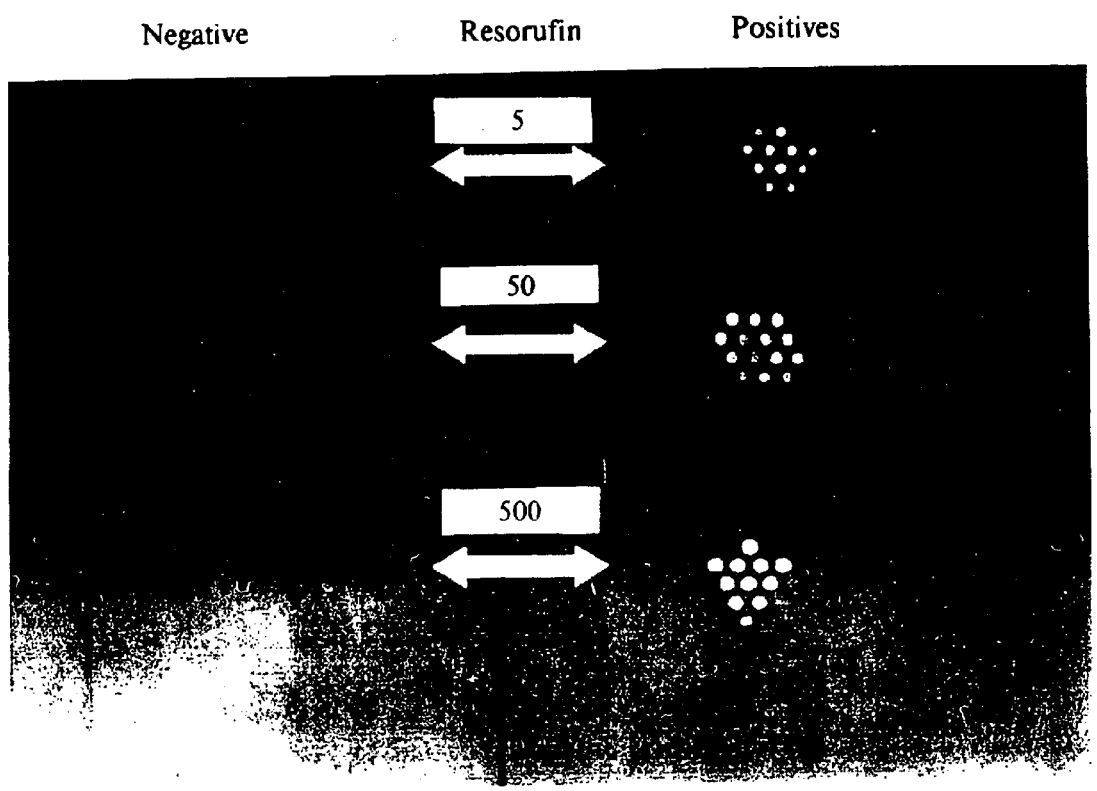
FIG. 10 shows detectable signals within capillary tubes of the capillary array at various concentrations of resorufin.
Figure 11:
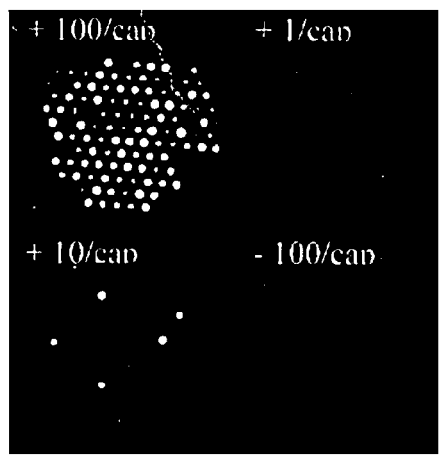
FIG. 11 shows detectable signals within the capillary tubes of the capillary array having various concentrations of cells from 1 to 100/capillary tube.
Figure 11:
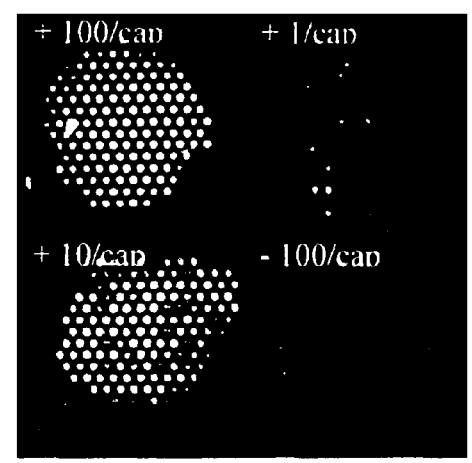
Figure 11:
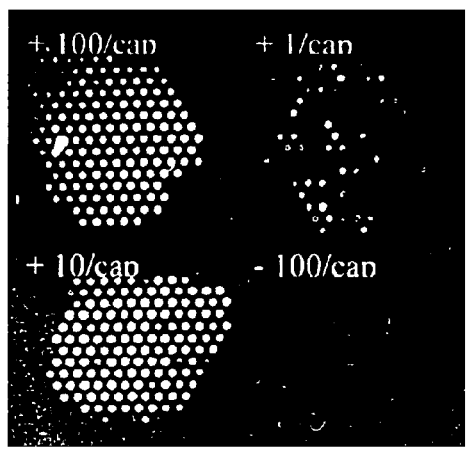
Figure 12:
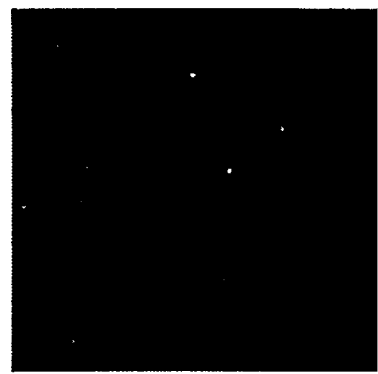
FIG. 12 shows the detection of positive cells within the capillary tubes of the capillary array. A mixture of positive and negative cells were wicked into the capillary tubes and a detectable signal measured at 8, 24 or 48 hours.
Figure 12:
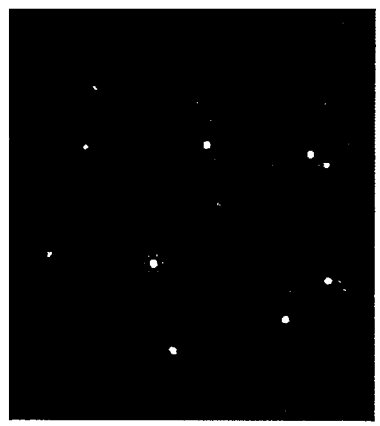
Figure 12:
Figure 12:
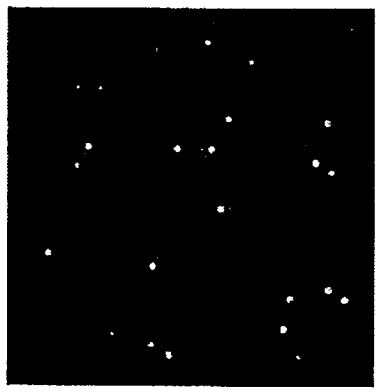
Figure 12:
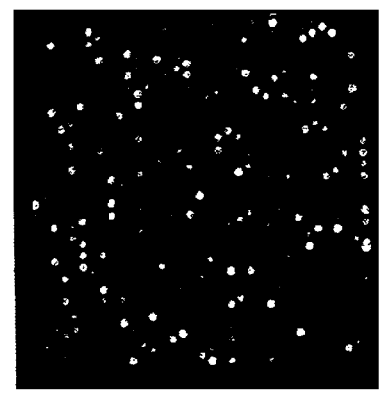

The cells were grown in the plates for 24 hours at 37° C./85% humidity. The cells were then pipetted directly onto an array and the array was imaged. As seen in FIG. 10 the cells grew well in the presence of 50 μm Resorufin β-gal which was easily detected.

β-gal positive 535 GL2 and β-gal negative MD 24.6 cells were grown in liquid culture. The cultures were diluted to 10 cell/capillary and 1 cell/capillary and mixed such that the final cell mixture wicked into the arrays was 95% MD 24.6:5% 535 GL2 cells. Resorufin β-gal was added to give a final concentration of 50 uM and the cell solutions were wicked into the arrays. The arrays were imaged over time (8 hours, 24 hours and 48 hours) (see FIG. 11).

β-gal positive 535 GL2 and negatives MD 24.6 cells were grown in liquid culture and the β-gal 535 GL2 cells were diluted to 100, 10, and 1 cells/capillary and the MD 24.6 to 100 cells/capillary. The cell dilutions were all mixed with resorufin β-gal to a final concentration of 50 uM and pipetted directly onto a 200 um diameter, 20 mm long capillary array. The array was incubated in the pipette tip box humid chamber at 37° C./85% humidity. The array was imaged at 8, 24, and 48 hours (see FIG. 12).

Example 5

β-gal positive 535 GL2 and β-gal negative MD 24.6 cells were grown in liquid culture. The cultures were diluted to 1 cell/capillary and mixed such that the final cell mixture wicked into the arrays was 99% MD 24.6:1% 535 GL2. Resorufin β-gal was added to give a final concentration of 50 uM and the cell solutions were wicked into an array. The array was incubated at 37° C./85% humidity in a water filled pipette box for 24 hours.

Figure 13:
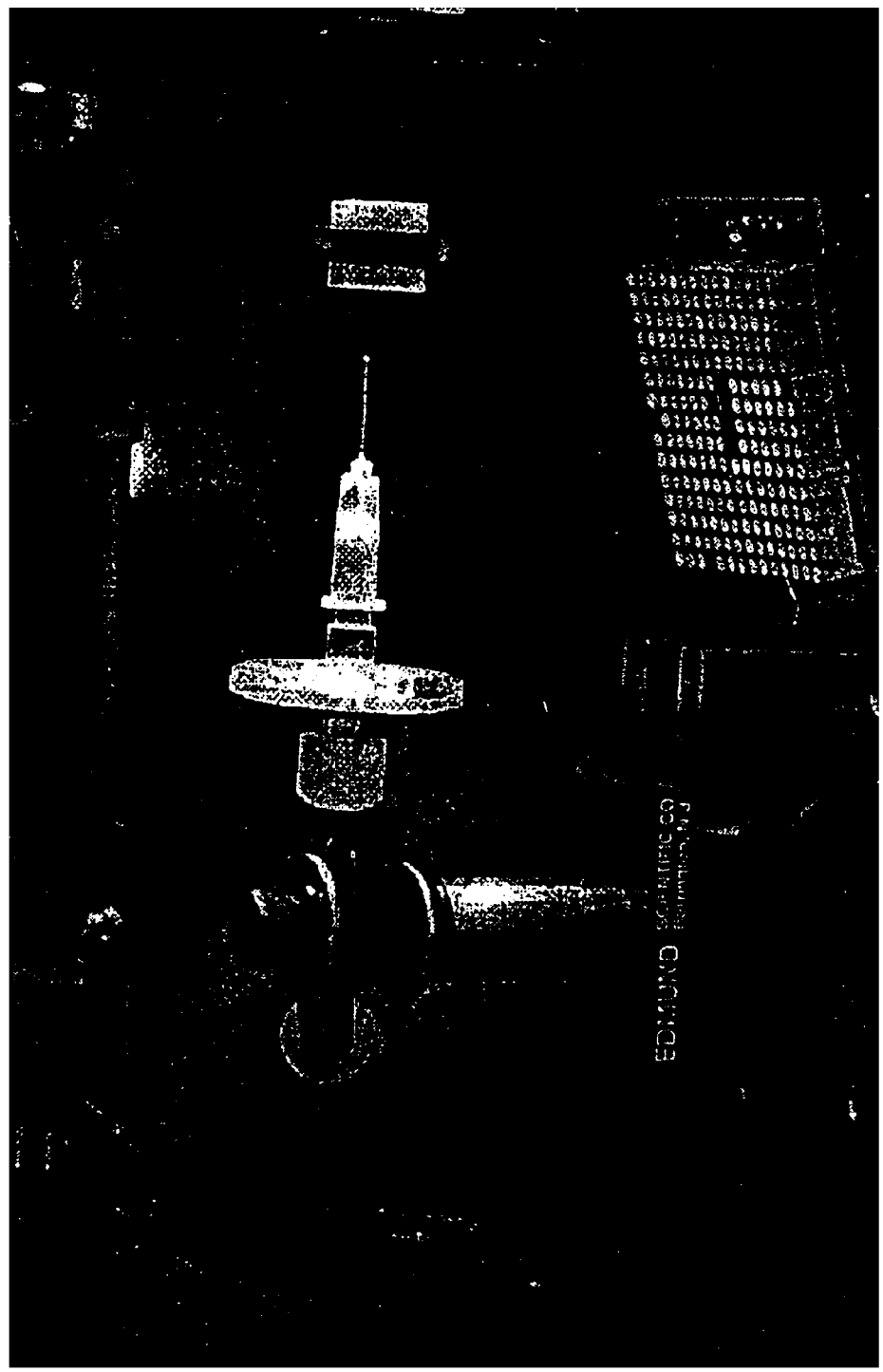
FIG. 13 is a picture of the recovery apparatus used to recover the contents of capillary tubes having positive signals.

Hits were recovered using a customized imaging and recovery system comprised of a CCD camera and a needle containing a filter which was attached to a vacuum source. Once a positive capillary/clone was identified the needle was aligned with the capillary and the sample aspirated out of the capillary and into the filter (see FIG. 13).

Example 6

Because imaging studies indicated that hit detection was dependent on whether the capillary top or bottom was imaged (i.e., the fluorophore was not distributed evenly), methods to stir the capillary contents were explored.

Paramagnetic beads (0.5–5 μm diameter beads) were wicked into arrays and magnets were used to stir arrays manually or by an automated device. In one embodiment, magnets are moved above and below a capillary array by a computer-controlled program operably connected to a compressed air system. Capillary arrays are held in a holder within a humidified incubator. Magnets are placed in holders identical to the one holding the array(s) and these holders are moved mechanically up and down causing magnetic beads within the arrays to alternately move toward the top magnet then toward the bottom one. For example, an array can be held in a metal holder that holds 12 arrays around it perimeter. This holder is placed in a 14 cm petri dish with foam surrounding its outer edges. The foam is dampened with sterile water and the petri dish is sealed with parafilm to form a humid chamber. Magnets are placed in holders identical to the one holding the arrays and the magnets are then move toward or away from the petri dish.

Figure 14:
FIG. 14 shows an image of detectable signals from the top and bottom of a capillary array of the invention after 12 hours of incubation.
Figure 14:
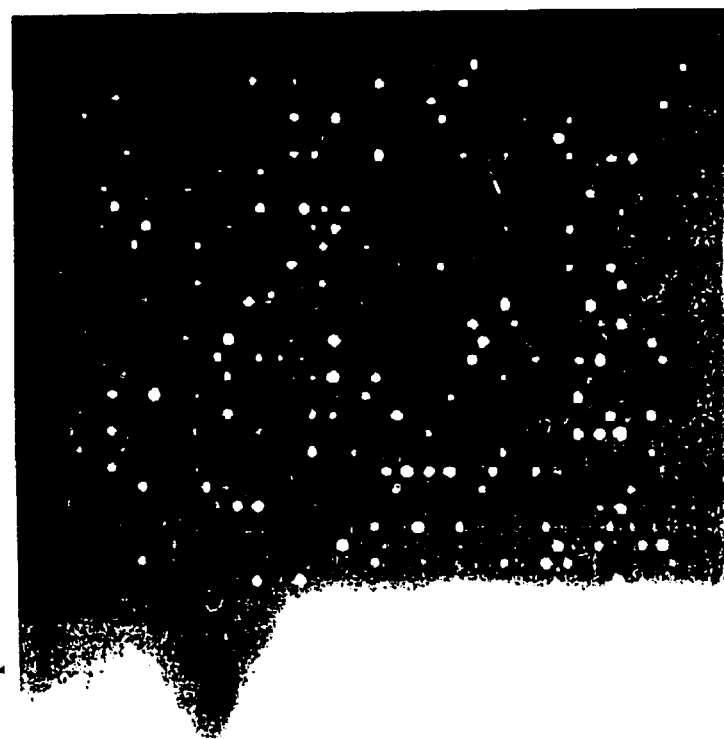
Figure 15:
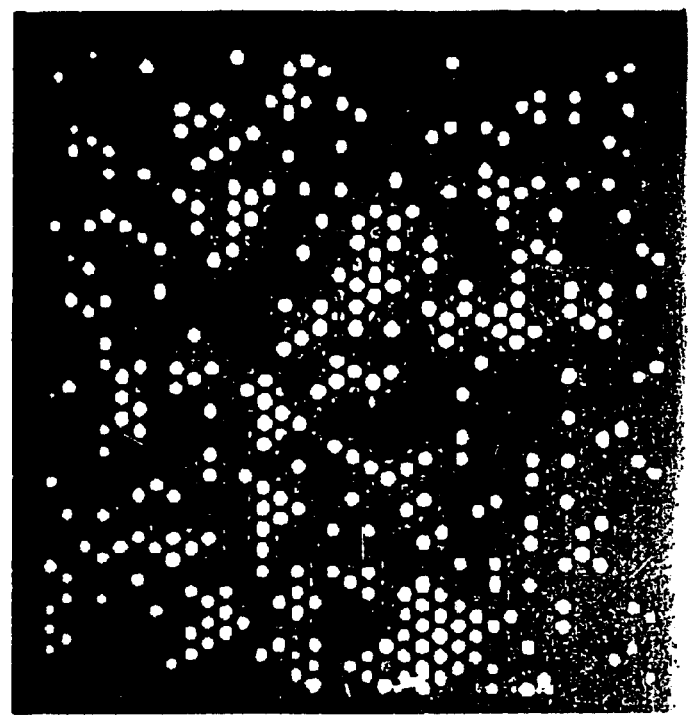
FIG. 15 shows the top and bottom image of the same array as in FIG. 14 following mixing the contents of the capillary tubes with magnetic beads.
Figure 15:
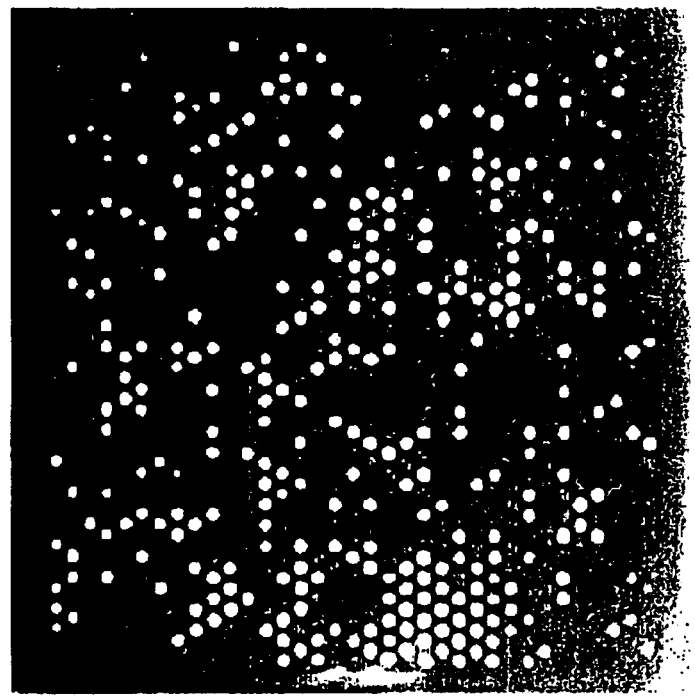

Liquid cultures of β-gal positive 535 GL2 and β-gal negative MD 24.6 were grown overnight in LB/KAN 50. Both cultures were diluted to 1 cell/capillary and mixed in a 95% negative/5% positive cell mixture with 50 uM resorufin β-gal. Paramagnetic beads (Spherotech 32–53 μm diameter) were added to the cell mixture. The cells with beads were wicked into an array. The array was incubated in a pipette tip box with Capillaries oriented horizontally for 12 hours and then imaged on the top and bottom (see FIG. 14). The array was then placed into a 14 cm petri dish having magnets disposed above and below the petri dish and stirred for 6 hours with a 5 second cycle time between magnet movements. The array was then imaged again on the top and bottom (see FIG. 15).

All headings and subheading herein are provided for the convenience of the reader and should not be construed to limit the present invention. While the invention has been described in detail with reference to certain preferred embodiments thereof, it will be understood that modifications and variations are within the spirit and scope of that which is described and claimed.

What is claimed is:

1. An automated capillary array system, comprising:
   a plurality of capillary tubes defining a capillary array, wherein each of the plurality of capillary tubes is separated from each other capillary tube in the array by at least one material having a low refractive index and wherein each capillary tube has openings at each end of the capillary tube;
   a mixing means for mixing the contents of the capillary tube;
   an optical array in optical communication with at least one end of the capillary array that detects an optical signal produced from a sample in at least one capillary tube of the capillary array; and
   a computer system in communication with the mixing means and the optical array, wherein the computer system controls the mixing of the capillary array and processes data detected by the optical array.

2. An automated capillary array system, comprising:
   a plurality of capillary tubes defining a capillary array, wherein each of the plurality of capillary tubes is separated from each other capillary tube in the array by at least one material having a low refractive index and wherein each capillary tube has openings at each end of the capillary tube;
   at least one magnetic field apparatus in magnetic communication with the capillary array to cause movement of paramagnetic beads;
   an optical array in optical communication with at least one end of the capillary array that detects an optical signal produced from a sample in at least one capillary tube of the capillary array; and
   a computer system in communication with the magnetic field apparatus and the optical array, wherein the computer system controls the magnetic field surrounding the capillary array and processes data detected by the optical array.

* * * * *